(12) United States Patent
Takahashi et al.

(10) Patent No.: US 10,782,567 B2
(45) Date of Patent: *Sep. 22, 2020

(54) OPTICAL FILM, POLARIZING PLATE, IMAGE DISPLAY DEVICE, POLYMERIZABLE COMPOUND, AND METHOD FOR MANUFACTURING 1,4-CYCLOHEXANEDICARBOXYLIC ACID MONOARYL ESTER

(71) Applicant: FUJIFILM Corporation, Tokyo (JP)

(72) Inventors: Keita Takahashi, Kanagawa (JP); Hiroshi Matsuyama, Kanagawa (JP); Naozumi Shiraiwa, Kanagawa (JP); Taiji Katsumata, Kanagawa (JP); Yuuta Fujino, Kanagawa (JP); Hiroshi Sato, Kanagawa (JP); Kiyoshi Takeuchi, Kanagawa (JP); Hiroyuki Hagio, Kanagawa (JP); Aiko Yoshida, Kanagawa (JP); Hiroaki Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 207 days.

This patent is subject to a terminal disclaimer.

(21) Appl. No.: 15/984,994

(22) Filed: May 21, 2018

(65) Prior Publication Data

US 2018/0267368 A1 Sep. 20, 2018

Related U.S. Application Data

(63) Continuation of application No. PCT/JP2016/084713, filed on Nov. 24, 2016.

(30) Foreign Application Priority Data

Nov. 26, 2015 (JP) .................................. 2015-230531
Jun. 24, 2016 (JP) .................................. 2016-125104

(51) Int. Cl.
| | | |
|---|---|---|
| G02F 1/1333 | (2006.01) | |
| G02F 1/1337 | (2006.01) | |
| G02F 1/13363 | (2006.01) | |
| C07C 67/14 | (2006.01) | |
| C09K 19/30 | (2006.01) | |
| C07C 67/30 | (2006.01) | |
| G02B 5/30 | (2006.01) | |
| H01L 51/52 | (2006.01) | |
| C09K 19/14 | (2006.01) | |
| F21V 8/00 | (2006.01) | |
| G02F 1/1335 | (2006.01) | |
| C09K 19/04 | (2006.01) | |

(52) U.S. Cl.
CPC ........ *G02F 1/133723* (2013.01); *C07C 67/14* (2013.01); *C07C 67/30* (2013.01); *C09K 19/14* (2013.01); *C09K 19/3068* (2013.01); *G02B 5/3033* (2013.01); *G02B 6/0056* (2013.01); *G02F 1/13363* (2013.01); *G02F 1/133528* (2013.01); *G02F 1/133788* (2013.01); *H01L 51/5281* (2013.01); *C07C 2601/14* (2017.05); *C09K 2019/0448* (2013.01); *C09K 2219/03* (2013.01); *G02F 2001/133637* (2013.01)

(58) Field of Classification Search
CPC ............ G02F 1/1333; G02F 1/133723; G02F 1/133528; G02F 1/13363; G02F 1/133788; G02F 2001/133637; C09K 19/14; C09K 19/3068; C09K 2019/0448; C09K 2219/03; C07C 67/14; C07C 67/30; C07C 2601/14; G02B 5/3033; G02B 6/0056; H01L 51/5281
USPC ...................................................... 252/299.6
See application file for complete search history.

(56) References Cited

U.S. PATENT DOCUMENTS

| | | | |
|---|---|---|---|
| 10,012,868 B2 * | 7/2018 | Nakazawa | ........... C09K 19/586 |
| 2010/0328600 A1 | 12/2010 | Shimada et al. | |
| 2015/0175564 A1 | 6/2015 | Sakamoto et al. | |
| 2017/0349828 A1 * | 12/2017 | Katoh | ................... C08F 222/30 |

(Continued)

FOREIGN PATENT DOCUMENTS

| | | |
|---|---|---|
| JP | 2009-256327 A | 11/2009 |
| JP | 2010-152217 A | 7/2010 |
| JP | 2010-270108 A | 12/2010 |

(Continued)

OTHER PUBLICATIONS

Office Action, issued by the Japanese Patent Office dated Feb. 26, 2019, in connection with Japanese Patent Application No. 2017-552675.

(Continued)

*Primary Examiner* — Geraldina Visconti
(74) *Attorney, Agent, or Firm* — Edwards Neils LLC; Jean C. Edwards, Esq.

(57) ABSTRACT

An object of the present invention is to provide an optical film having an optically-anisotropic layer having excellent durability, a polarizing plate and an image display device in which the optical film is used, a polymerizable compound used in the optical film, and a method for manufacturing a 1,4-cyclohexanedicarboxylic acid monoaryl ester. The optical film of the present invention is an optical film having at least an optically-anisotropic layer, in which the optically-anisotropic layer is a layer obtained by polymerizing a polymerizable liquid crystal composition containing a polymerizable compound which has a specific structure, a liquid crystal compound which has a specific structure, and a polymerization initiator.

19 Claims, 1 Drawing Sheet

(56) References Cited

U.S. PATENT DOCUMENTS

2018/0267368 A1* 9/2018 Takahashi .............. C09K 19/14

FOREIGN PATENT DOCUMENTS

| JP | 2012-077055 A | 4/2012 |
| --- | --- | --- |
| WO | 2009-034867 A1 | 3/2009 |
| WO | 2014/010325 A1 | 1/2014 |
| WO | 2014/132978 A1 | 9/2014 |
| WO | 2015/147243 A1 | 10/2015 |

OTHER PUBLICATIONS

International Search Report issued in PCT/JP2016/084713 dated Jan. 31, 2017.
Written Opinion issued in PCT/JP2016/084713 dated Jan. 31, 2017.
International Preliminary Report on Patentability completed by WIPO dated Jun. 7, 2018, in connection with International Patent Application No. PCT/JP2016/084713.
Office Action, issued by the Korean Intellectual Property Office dated Dec. 18, 2019, in connection with Korean Patent Application No. 10-2018-7014601.

* cited by examiner

OPTICAL FILM, POLARIZING PLATE, IMAGE DISPLAY DEVICE, POLYMERIZABLE COMPOUND, AND METHOD FOR MANUFACTURING 1,4-CYCLOHEXANEDICARBOXYLIC ACID MONOARYL ESTER

CROSS-REFERENCE TO RELATED APPLICATIONS

This application is a Continuation of PCT International Application No. PCT/JP2016/084713 filed on Nov. 24, 2016, which was published under PCT Article 21(2) in Japanese, and which claims priority under 35 U.S.C. § 119(a) to Japanese Patent Application No. 2015-230531 filed on Nov. 26, 2015 and Japanese Patent Application No. 2016-125104 filed on Jun. 24, 2016. The above applications are hereby expressly incorporated by reference, in their entirety, into the present application.

BACKGROUND OF THE INVENTION

1. Field of the Invention

The present invention relates to an optical film, a polarizing plate, an image display device, and a polymerizable compound.

2. Description of the Related Art

In order to solve the coloration of an image or to widen a viewing angle, an optical film such as an optical compensation sheet or a phase difference film is used in various image display devices.

As the optical film, a stretched birefringence film has been used. However, in recent years, instead of the use of the stretched birefringence film, the use of an optical film having an optically-anisotropic layer formed of a liquid crystal compound has been suggested.

As such an optical film, an optical film formed using a composition containing a predetermined polyinerizable compound and a polymerization initiator is known (for example, see JP2010-270108A, JP2012-077055A, and WO2014/010325A).

SUMMARY OF THE INVENTION

The inventors of the present invention examined the optical films described in JP2010-270108A, JP2012-077055A, and WO2014/010325A. As a result, it was revealed that depending on the type of the polymerizable liquid crystal compound or the polymerization initiator to be used and on the polymerization conditions such as a curing temperature, in a case where the formed optically-anisotropic layer is exposed to a high temperature and a high humidity, a problem relating to durability such as a change in a birefringence index occurs.

Therefore, an object of the present invention is to provide an optical film having an optically-anisotropic layer having excellent durability, a polarizing plate and an image display device in which the optical film is used, a polymerizable compound used in the optical film, and a method for manufacturing a 1,4-cyclohexanedicarboxylic acid monoaryl ester.

In order to achieve the aforementioned object, the inventors of the present invention conducted an intensive examination. As a result, the inventors have found that in a case where a predetermined liquid crystal compound having a cyclohexane ring and a specific polymerizable compound having a cyclohexane ring are used in combination, the durability of the formed optically-anisotropic layer becomes excellent, and have accomplished the present invention.

That is, the inventors have found that the aforementioned object can be achieved by the constitutions described below.

An optical film comprising at least an optically-anisotropic layer, in which the optically-anisotropic layer is a layer obtained by polymerizing a polymerizable liquid crystal composition containing a polymerizable compound represented by Formula (I) which will be described later, a liquid crystal compound represented by Formula (II), which will be described later, and does not correspond Formula (I) which will be described later, and a polymerization initiator.

[2] The optical film described in [1], in which the optically-anisotropic layer satisfies Formula (I), $$0.75 < Re(450)/Re(550) < 1.00 \tag{1}$$

In Formula (I), Re (450) represents in-plane retardation of the optically-anisotropic layer at a wavelength of 450 nm, and Re (550) represents in-plane retardation of the optically-anisotropic layer at a wavelength of 550 nm.

[3] The optical film described in [1] or [2], in which the liquid crystal compound is a liquid crystal compound having reciprocal wavelength dispersion properties.

[4] The optical film described in any one of [1] to [3], in which both of m and n Formula (I), which will be described later, represent 1.

[5] The optical film described in any one of [1] to [4], in which both of $Z^1$ and $Z^2$ in Formula (I), which will be described later, represent an arylene group which may have a substituent.

[6] The optical film described in any one of [1] to [5], in which all of $L^1$, $L^2$, $L^3$, and $L^4$ in Formula (I), which will be described later, represent —C(=O)O— or —OC(=O)—.

[7] The optical film described in any one of [1] to [6], in which $Sp^1$ and $Sp^2$ in Formula (I), which will be described later, represent a linking group selected from groups formed in a case where one or more —CH$_2$— groups constituting a linear or branched alkylene group having 5 to 15 carbon atoms are substituted with —O—, —OC(=O)—, or —C(=O)O—.

[8] The optical film described in any one of [1] to [7], in which $R^1$ and $R^2$ in Formula (I), which will be described later, represent an acryloyl group represented by Formula (R-1) or a methacryloyl group represented by Formula (R-1).

[9] The optical film described in any one of [1] to [8], in which $Ar^1$ in Formula (I), which will be described later, represents an aromatic ring represented by Formula (Ar-3).

[10] The optical film described in any one of [1] to [9], in which the polymerization initiator is an oxime-type polymerization initiator.

[11] A polarizing plate comprising the optical film described in any one of [1] to [10] and a polarizer.

[12] An image display device comprising the optical film described in any one of [1] to [11] or the polarizing plate described in [11].

[13] A polymerizable compound represented by Formula (I) which will be described later.

[14] The polymerizable compound described in [13], in which both of m and n in Formula (I), which will be described later, represent 1.

[15] The polymerizable compound described in [13] or [14], in which $Z^1$ and $Z^2$ in Formula (I), which will be described later, represent an arylene group which may have a substituent.

[16] The polymerizable compound described in any one of [13] to [15], in which all of $L^1$, $L^3$, and $L^4$ in Formula (I), which will be described later, represent —C(=O)O— or —OC(=O)—.

[17] The polymerizable compound described in any one of [13] to [16], in which $Sp^1$ and $Sp^2$ in Formula (I), which will be described later, represent a linking group selected from groups formed in a case where one or more —CH$_2$— groups constituting a linear or branched alkylene group having 5 to 15 carbon atoms are substituted with —O—, —OC(=O)—, or —C(=O)O—.

[18] The polymerizable compound described in any one of [13] to [17], in which $R^1$ and $R^2$ in Formula (I), which will be described later, represent an acryloyl group represented by Formula (R-1) or a methacryloyl group represented by Formula (R-1).

[19] The polymerizable compound described in any one of [13] to [18], in which $Ar^1$ in Formula (I), which will be described later, represents an aromatic ring represented by Formula (Ar-3).

[20] A method for manufacturing a 1,4-cyclohexanedicarboxylic acid monoaryl ester, comprising a reaction step of reacting 1,4-cyclohexanedicarboxylic acid dichloride with a phenol-based compound in the presence of a base whose conjugate acid has an acid dissociation constant pKa of equal to or greater than 7 and equal to or smaller than 30, and a hydrolysis step of hydrolyzing a reaction product obtained by the reaction step so as to obtain a 1,4-cyclohexanedicarboxylic acid monoaryl ester represented by Formula (Ia) or (IIa) which will be described later, in which in the reaction step, a ratio of a molar equivalent of the 1,4-cyclohexanedicarboxylic acid dichloride to a molar equivalent of the phenol-based compound is equal to or higher than 1.5 and equal to or lower than 10.

According to the present invention, it is possible to provide an optical film having an optically-anisotropic layer having excellent durability, a polarizing plate and an image display device in which the optical film is used, a polymerizable compound used in the optical film, and a method for manufacturing a 1,4-cyclohexanedicarboxylic acid monoaryl ester.

DESCRIPTION OF THE PREFERRED EMBODIMENTS

Hereinafter, the present invention will be specifically described.

In the following section, constituents will be described based on typical embodiments of the present invention in some cases, but the present invention is not limited to the embodiments.

In the present specification, a range of numerical values described using "to" means a range including the numerical values listed before and after "to" as a lower limit and an upper limit.

[Optical Film]

The optical film of the present invention is an optical film having at least an optically-anisotropic layer. The optically-anisotropic layer is a layer obtained by polymerizing a polymerizable liquid crystal composition containing a polymerizable compound represented by Formula (I) which will be described later (hereinafter, simply described as "polymerizable compound (I)" as well), a liquid crystal compound represented by Formula (II) which will be described later and does not correspond to Formula (I) which will be described later (hereinafter, simply described as "liquid crystal compound (II)" as well), and a polymerization initiator.

In the present invention as described above, by using the liquid crystal compound (II) and the polymerizable compound (I) in combination, the durability of the formed optically-anisotropic layer becomes excellent.

The reason is unclear but is assumed to be as below by the inventors of the present invention.

The ester bond included in the structure of the liquid crystal compound still exists even after polymerization, that is, even after the optically-anisotropic layer is formed. The inventors of the present invention assume that in a case where a hydrolyzable bond such as the ester bond is hydrolyzed in a high-temperature and high-humidity environment, a portion of the liquid crystal compound fixed by a polymerizable group may be liberated and obtain mobility, and hence a birefringence index may change.

Therefore, in the present invention, the polymerizable compound (I) is used so as to make it difficult for moisture to permeate the inside of the optically-anisotropic layer even in a high-temperature and high-humidity environment due to the steric hindrance resulting from two or more substituents of the aromatic ring represented by $Ar^1$ in Formula (I) which will be described later, that is, the aromatic ring represented by any of Formulae (Ar-1) to (Ar-4) which will be described later. Presumably, as a result, hydrolysis may not easily occur, and hence the durability may be improved.

Figure 1A:
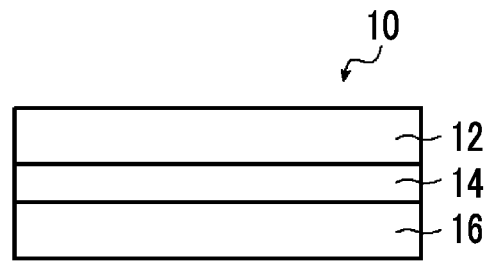
FIG. 1A is a cross-sectional view schematically showing an example of an optical film of the present invention.
Figure 1B:
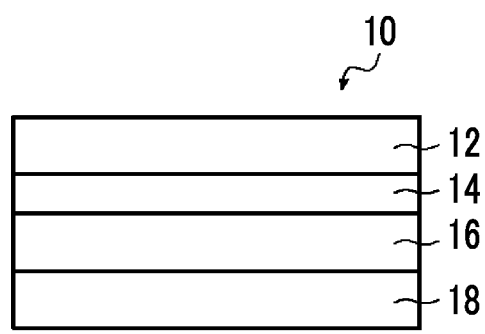
FIG. 1B is a cross-sectional view schematically showing an example of the optical film of the present invention.
Figure 1C:
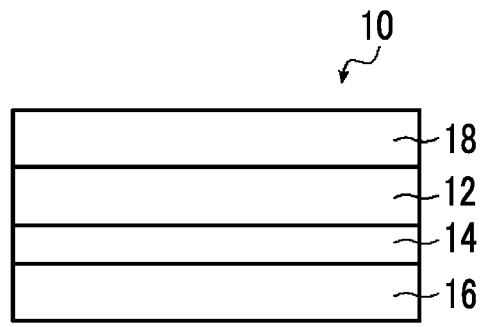
FIG. 1C is a cross-sectional view schematically showing an example of the optical film of the present invention.

FIGS. 1A, 1B, and 1C (hereinafter, in a case where these drawings do not need to be particularly differentiated from each other, these will be simply described as "FIG. 1") are cross-sectional views schematically showing an example of the optical film of the present invention respectively.

FIG. 1 is merely a schematic view. Therefore, the relationship between the layers in terms of the thickness, the position, and the like is not necessarily exactly the same as the real one, and all of the support, the alignment film, and the hardcoat layer shown in FIG. 1 are optional constituent members.

An optical film 10 shown in FIG. 1 has a support 16, an alignment film 14, and an optically-anisotropic layer 12 in this order.

The optical film 10 may have a hardcoat layer 18 on a side, which is opposite to a side provided with the alignment film 14, of the support 16 as shown in FIG. 1B or on a side, which is opposite to a side provided with the alignment film 14, of the optically-anisotropic layer 12 as shown in FIG. 1C.

Hereinafter, various members used in the optical film of the present invention will be specifically described.

[Optically-Anisotropic Layer]

The optically-anisotropic layer included in the optical film of the present invention is a layer obtained by polymerizing a polymerizable liquid crystal composition containing the polymerizable compound (I), the liquid crystal compound (II), and a polymerization initiator.

<Polymerizable Compound (I)>

The polymerizable liquid crystal composition forming the optically-anisotropic layer contains the polymerizable compound (I) represented by Formula (I) shown below.

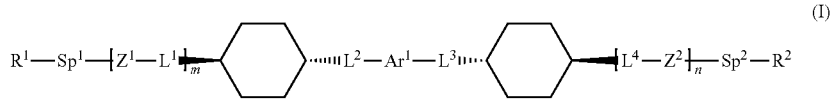

In Formula (I) shown above, although all of the two cyclohexane rings represent a trans-1,4-cyclohexylene group, the bonds in the cyclohexane rings are in opposite directions (trans-isomers).

Therefore, there is no particular limitation on the relationship between the direction of bonding between the cyclohexane ring on the left side in Formula (I) shown above and $L^2$ and the direction of bonding between the cyclohexane ring on the right side and $L^3$. The structure represented by Formula (I) shown above may be any of the structures shown below.

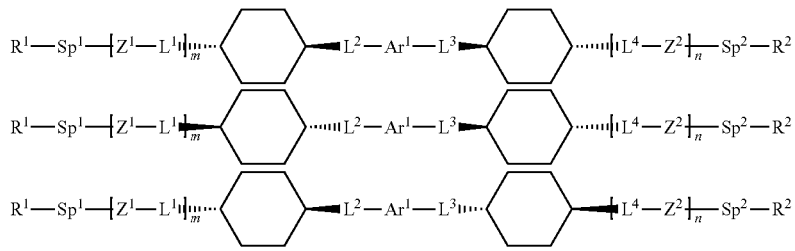

In Formula (I) shown above, m and n each independently represent an integer of 0 to 2, and m+n equals an integer of 2 to 4. All of $Z^1$, $Z^2$, $L^1$, and $L^4$, each of which becomes a plurality of groups depending on the number represented by m or n, may be the same as or different from each other.

In the present invention, it is preferable that both of m and n represent 1, because then the solubility becomes excellent, and the manufacturing suitability is improved.

In Formula (I) shown above, $Z^1$ and $Z^2$ each independently represent a trans-1,4-cyclohexylene group which may have a substituent, an arylene group which may have a substituent, or a heteroarylene group which may have a substituent. At least one of $Z^1$ or $Z^2$ represents an arylene group which may have a substituent or a heteroarylene group which may have a substituent.

The aforementioned arylene group is preferably an arylene group having 6 to 20 carbon atoms, and more preferably an arylene group having 6 to 10 carbon atoms. Specific examples of such an arylene group include a 1,4-phenylene group, a naphthalene-2,6-diyl group, a tetrahydronaphthalene-2,6-diyl group, and the like. Among these, a 1,4-phenylene group is preferable.

The aforementioned heteroarylene group is preferably a heteroarylene group having 2 to 9 carbon atoms. Specific examples of the heteroarylene group include a pyridine ring, a quinoline ring, an isoquinoline ring, a pyrimidine ring, a pyrazine ring, a thiophene ring, a furan ring, an oxazole ring, a thiazole ring, an imidazole ring, a pyrazole ring, an oxadiazole ring, a thiadiazole ring, a triazole ring, a group obtained by removing one hydrogen atom from each of two carbon atoms constituting any of ring structures selected from the group consisting of condensed rings formed by the condensation of the above rings, and the like.

Examples of the substituent that the trans-1,4-cyclohexylene group, the arylene group, or the heteroarylene group represented by $Z^1$ and $Z^2$ may have include an alkyl group, an alkoxy group, a halogen atom, and the like.

The alkyl group is, for example, preferably a linear, branched, or cyclic alkyl group having 1 to 18 carbon atoms, more preferably an alkyl group having 1 to 8 carbon atoms (for example, a methyl group, an ethyl group, a propyl group, an isopropyl group, a n-butyl group, an isobutyl group, a sec-butyl group, a t-butyl group, a cyclohexyl group, and the like), and even more preferably a methyl group or an ethyl group.

The alkoxy group is, for example, preferably an alkoxy group having 1 to 18 carbon atoms, more preferably an alkoxy group having 1 to 8 carbon atoms (for example, a methoxy group, an ethoxy group, a n-butoxy group, a methoxyethoxy group, and the like), and even more preferably a methoxy group or an ethoxy group.

Examples of the halogen atom include a fluorine atom, a chlorine atom, a bromine atom, an iodine atom, and the like. Among these, a fluorine atom and a chlorine atom are preferable.

In the present invention, for expressing liquid crystallinity, both of $Z^1$ and $Z^2$ in Formula (I) shown above preferably represent an arylene group which may have a substituent and more preferably represent a 1,4-phenylene group which may have a substituent.

In Formula (I) shown above, $L^1$, $L^2$, $L^3$, and $L^4$ each independently represent any linking group selected from the group consisting of a single bond, —O—, —CH$_2$O—, —OCH$_2$—, —(CH$_2$)$_2$OC(=O)—, —C(=O)O(CH$_2$)$_2$—, —NH—, —N(CH$_3$)—, —S—, —C(=O)O—, —OC(=O)—, —OC(=O)O—, —C(=O)N(R$^3$)—, —N(R$^3$)C(=O)—, —C(=O)S—, —SC(=O)—, —CH$_2$C(=O)O—, —OC(=O)CH$_2$—, —CH=CH—C(=O)O—, —OC(=O)—CH=CH—, —CH=N—, —N=CH—, and —N=N—, and R$^3$ represents a hydrogen atom, an alkyl group having 1 to 20 carbon atoms, or an aryl group having 6 to 20 carbon atoms.

Specific examples of the alkyl group represented by R$^3$ include a methyl group, an ethyl group, an isopropyl group, a tert-butyl group, a n-octyl group, a n-decyl group, a n-hexadecyl group, a cyclopropyl group, a cyclopentyl group, a cyclohexyl group, and the like. Among these, an alkyl group having 1 to 12 carbon atoms is preferable, and an alkyl group having 1 to 8 carbon atoms is more preferable.

Specific examples of the aryl group represented by $R^3$ include a phenyl group, a 2,6-diethylphenyl group, a naphthyl group, a biphenyl group, and the like. Among these, an aryl group having 6 to 12 carbon atoms is preferable.

In the present invention, it is preferable that all of $L^1$, $L^2$, $L^3$, and $L^4$ in Formula (I) shown above represent —C(=O)O— or —OC(=O)—, because then the solubility becomes excellent, and the manufacturing suitability is improved.

In the present invention, $L^2$ in Formula (I) shown above is preferably —C(=O)O— from the direction of $R^1$ and much preferably —OC(=O)— from the direction of $R^1$.

In Formula (I) shown above, $Sp^1$ and $Sp^2$ each independently represent any linking group selected from the group consisting of a single bond, a linear or branched alkylene group having 1 to 20 carbon atoms, and a group obtained in a case where one or more —$CH_2$— groups constituting a linear or branched alkylene group having 1 to 20 carbon atoms are substituted with —O—, —S—, —NH—, —N($CH_3$)—, —C(=O)—, —OC(=O)—, or —C(=O)O—.

The linear or branched alkylene group (including an unsubstituted alkylene group) having 1 to 20 carbon atoms represented by $Sp^1$ and $Sp^2$ is preferably a linear or branched alkylene group having 5 to 15 carbon atoms. Specific examples thereof include a pentylene group, a hexylene group, an octylene group, a decylene group, and the like.

In the present invention, for expressing liquid crystallinity, $Sp^1$ and $Sp^2$ in Formula (I) shown above preferably represent a group (linking group) obtained in a case where one or more groups constituting a linear or branched alkylene group having 1 to 20 carbon atoms are substituted with —O—, —S—, —NH—, —N($CH_3$)—, —C(=O)—, —OC(=O)— or —C(=O)O—, more preferably represent a group (linking group) obtained in a case where one or more —$CH_2$— groups constituting a linear or branched alkylene group having 5 to 15 carbon atoms are substituted with —O—, —OC(=O)—, or —C(=O)O—, and even more preferably represent a group (linking group) obtained in a case where one or two —$CH_2$— groups constituting a linear or branched alkylene group having 5 to 15 carbon atoms are substituted with —OC(=O)— or —C(=O)O— and one —$CH_2$— group constituting a linear or branched alkylene group having 5 to 15 carbon atoms is substituted with —O—.

In Formula (I) shown above, $R^1$ and $R^2$ each independently represent any polymerizable group selected from the group consisting of groups represented by Formulae (R-1) to (R-5) shown below. In Formulae (R-1) to (R-5) shown below, * represents a position bonded to $Sp^1$ or $Sp^2$.

From the viewpoint polymerization suitability, $R^1$ and $R^2$ in Formula (I) shown above preferably represent, among the aforementioned groups, an acryloyl group represented by Formula (R-1) shown below or a methacryloyl group represented by Formula (R-1) shown below.

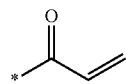
(R-1)

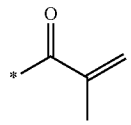
(R-2)

(R-3)

(R-4)

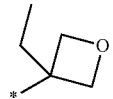
(R-5)

In Formula (I) shown above, $Ar^1$ represents any aromatic ring selected from the group consisting of groups represented by Formulae (Ar-1) to (Ar-4) shown below. In Formulae (Ar-1) to (Ar-4) shown below, *1 represents a position bonded to $L^2$, and *2 represents a position bonded to $L^3$.

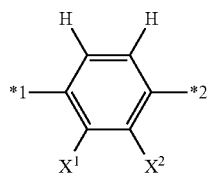
(Ar-1)

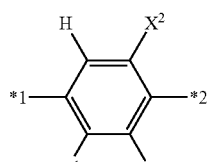
(Ar-2)

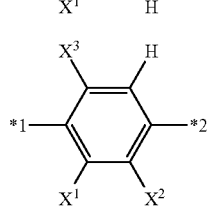
(Ar-3)

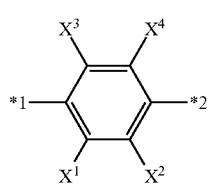
(Ar-4)

In Formulae (Ar-1) to (Ar-4) shown above, $X^1$, $X^2$, $X^3$, and $X^4$ each independently represent a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$CO_2R^4$, —$NR^5R^6$, or $SR^5$, and $R^4$, $R^5$, and $R^6$ each independently represent a hydrogen atom or an alkyl group having 1 to 6 carbon atoms.

The monovalent aliphatic hydrocarbon group having 1 to 20 carbon atoms is preferably an alkyl group having 1 to 15 carbon atoms, and more preferably an alkyl group having 1 to 8 carbon atoms. Specifically, a methyl group, an ethyl group, an isopropyl group, a tert-pentyl group (1,1-dimethylpropyl group), a tert-butyl group, and a 1,1-dimethyl-3,3-dimethyl-butyl group are even more preferable, and a methyl group, an ethyl group, and a tert-butyl group are particularly preferable.

Examples of the monovalent alicyclic hydrocarbon group having 3 to 20 carbon atoms include monocyclic saturated hydrocarbon group such as a cyclopropyl group, a cyclobutyl group, a cyclopentyl group, a cyclohexyl group, a cycloheptyl group, a cyclooctyl group, a cyclodecyl group, a methylcyclohexyl group, or an ethylcyclohexyl group; a monocyclic unsaturated hydrocarbon group such as a cyclobutenyl group, a cyclopentenyl group, a cyclohexenyl group, a cycloheptenyl group, a cyclooctenyl group, a cyclo- Specific examples of the alkyl group represented by $R^4$, $R^5$, and $R^6$ include a methyl group, an ethyl group, an isopropyl group, a tert-butyl group, and the like.

In the present invention, from the viewpoint of the availability of raw materials, it is preferable that $Ar^1$ in Formula (I) shown above represents an aromatic ring represented by Formula (Ar-3) shown above.

In the present invention, from the viewpoint of the solubility, the manufacturing suitability, the expression of liquid crystallinity, the polymerization suitability, and the like, the polymerizable compound (I) represented by Formula (I) shown above is preferably a polymerizable compound represented by any of Formulae (IA) to (ID) shown below, and more preferably a polymerizable compound represented by Formula (IA) shown below.

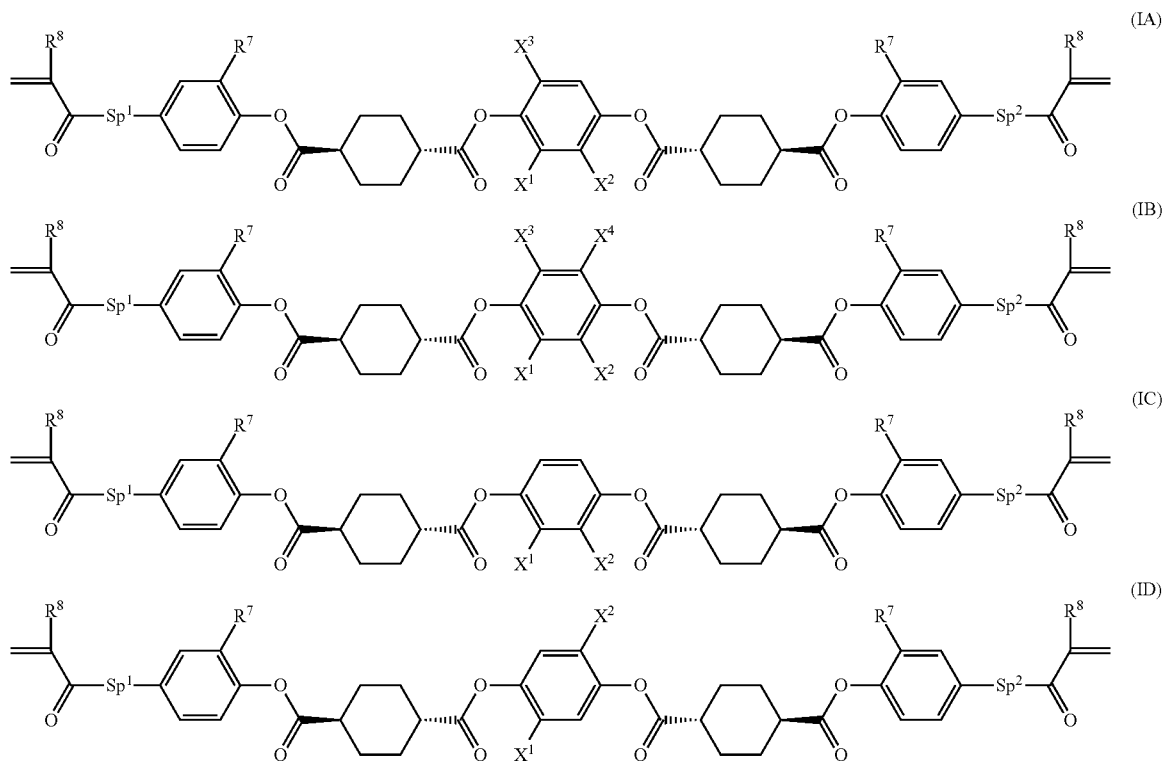

decenyl group, a cyclopentadienyl group, a cyclohexadienyl group, a cyclooctadienyl group, or cyclodecadienyl group; a polycyclic saturated hydrocarbon group such as a bicyclo[2.2.1]heptyl group, a bicyclo[2.2.2]octyl group, a tricyclo[5.2.1.0$^{2,6}$]decyl group, a tricyclo[3.3.1.1$^{3,7}$]decyl group, a tetracyclo[6.2.1.1$^{3,6}$.0$^{2,7}$]dodecyl group, or an adamantyl group; and the like.

Specific examples of the monovalent aromatic hydrocarbon group having 6 to 20 carbon atoms include a phenyl group, a 2,6-diethylphenyl group, a naphthyl group, a biphenyl group, and the like. Among these, an aryl group (particularly a phenyl group) having 6 to 12 carbon atoms is preferable.

Examples of the halogen atom include a fluorine atom, a chlorine atom, a bromine atom, an iodine atom, and the like. Among these, a fluorine atom, a chlorine atom, and a bromine atom are preferable.

In Formulae (IA) to (ID) shown above, $Sp^1$, $Sp^2$, $X^1$, $X^2$, $X^3$, and $X^4$ have the same definitions as those in Formula (I) described above.

In Formulae (LA) to (ID) shown above, $R^7$ represents a hydrogen atom, an alkyl group, an alkoxy group, or a halogen atom. Examples of the alkyl group, the alkoxy group, and the halogen atom are the same as the examples of the substituent that $Z^1$ and $Z^2$ in Formula (I) described above may have. A plurality of $R^7$'s may be the same as or different from each other.

Furthermore, $R^8$ represents a hydrogen atom or a methyl group.

Examples of the polymerizable compound (I) represented by Formula (I) shown above include compounds represented by Formulae (I-1) to (I-18) shown below, and the like.

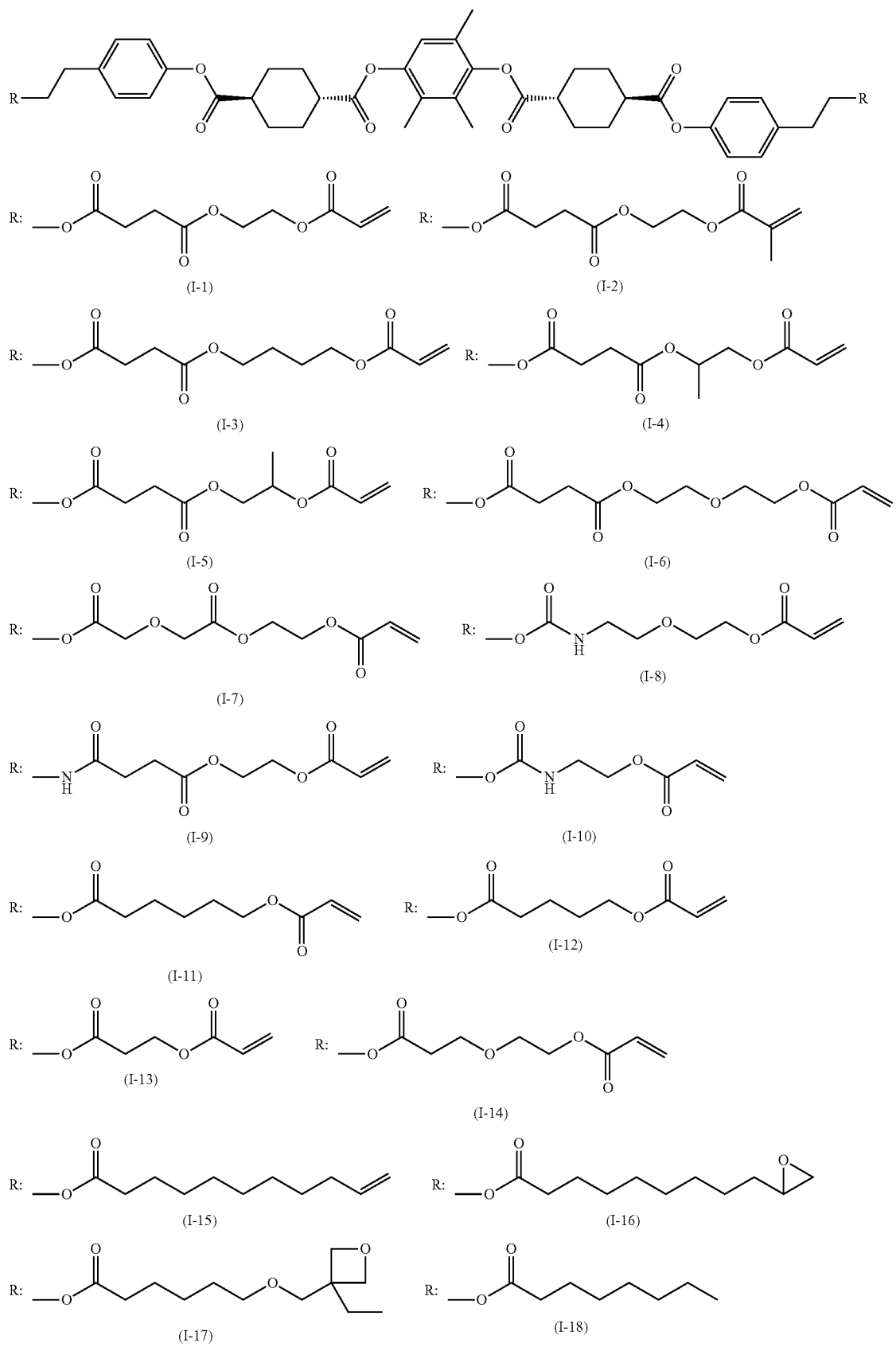

R in Formulae (I-1) to (I-18) shown above includes bonds with carbon atoms adjacent to R. Therefore, for example, the structure of the compound represented by Formula (I-1) shown above is as below.
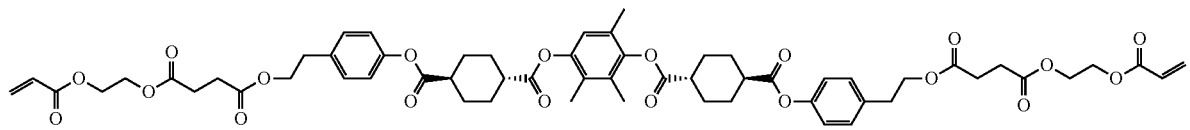 [SMILES: C=CC(=O)OCCOC(=O)CCC(=O)OCCc1ccc(OC(=O)[C@H]2CC[C@H](C(=O)Oc3cc(C)c(OC(=O)[C@H]4CC[C@H](C(=O)Oc5ccc(CCOC(=O)CCC(=O)OCCOC(=O)C=C)cc5)CC4)c(C)c3C)CC2)cc1]
Specific examples of the polymerizable compound (I) represented by Formula (I) shown above also include compounds represented by Formulae (I-19) to (I-28) shown below, and the like.
(I-19)
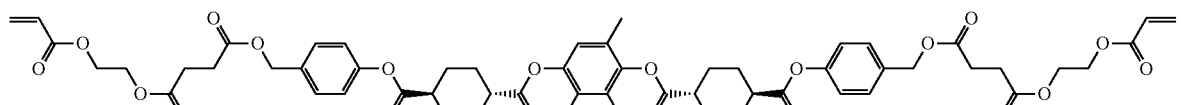
(I-20)
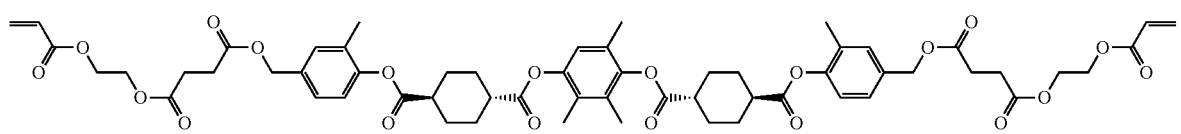
(I-21)
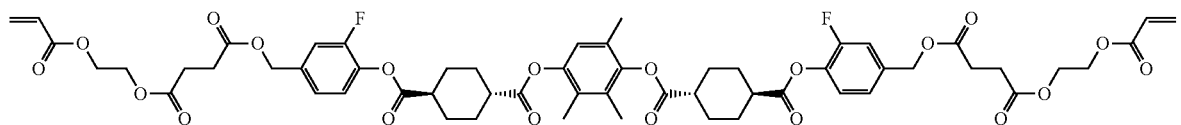
(I-22)
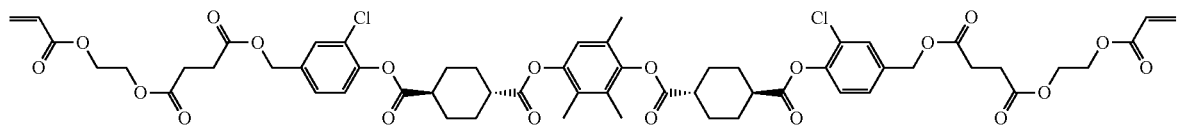
(I-23)
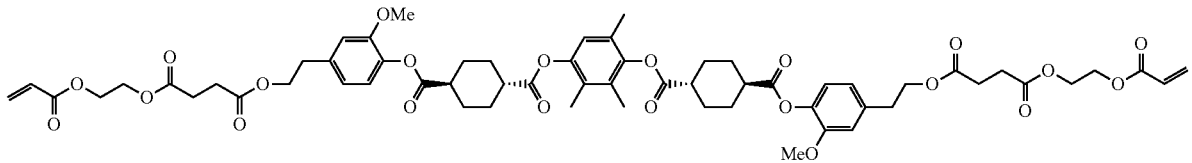
(I-24)
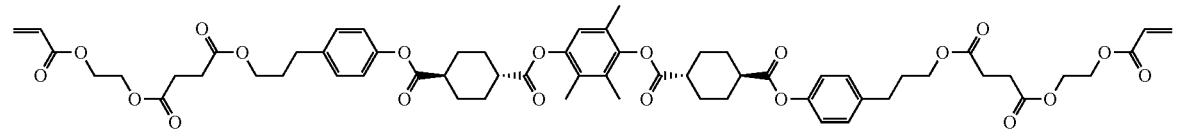
(I-25)
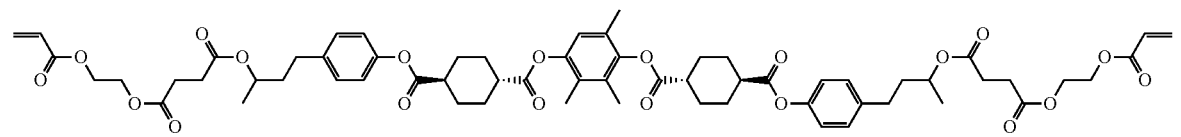

(I-26)
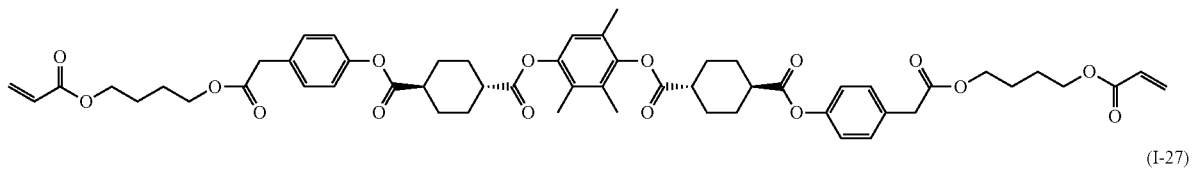

(I-27)
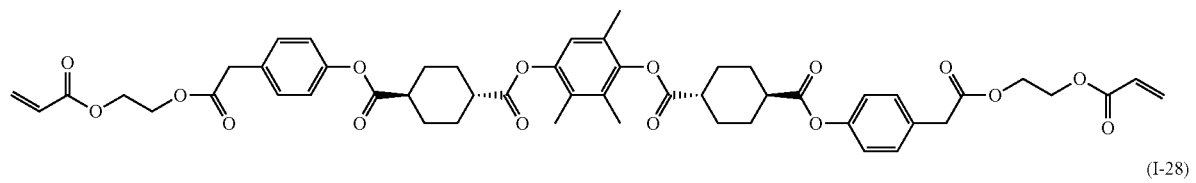

(I-28)
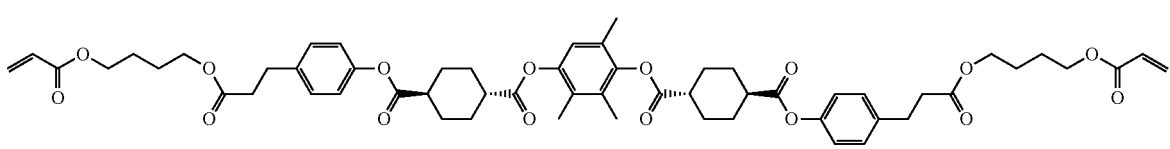

Specific examples of the polymerizable compound (I) represented by Formula (I) shown above also include compounds represented by Formulae (I-29) to (I-40) shown below and the like. In the formulae shown below, "tBu" represents a tert-butyl group, "Me" represents a methyl group, "Et" represents an ethyl group, "OMe" represents a methoxy group, "OEt" represents an ethoxy group, and * represents a position bonded to a benzene ring. The same shall be applied to the example compounds which will be described later.

| $Z_1$ | $Z_2$ | $Z_3$ | $Z_4$ | |
|---|---|---|---|---|
| $CH_3$ | $CH_3$ | H | H | (I-29) |
| $CH_3$ | H | H | $CH_3$ | (I-30) |
| $CH_3$ | $CH_3$ | $CH_3$ | $CH_3$ | (I-31) |
| F | F | F | F | (I-32) |
| Cl | Cl | Cl | Cl | (I-33) |
| Br | Br | Br | Br | (I-34) |
| $^tBu$ | H | H | $^tBu$ | (I-35) |
| *—C(Me)(Me)—Et | H | H | *—C(Me)(Me)—Et | (I-36) |
| *—C(Me)(Me)—CH$_2$—C(Me)(Me)—Me | H | H | | (I-37) |
| CN | CN | H | H | (I-38) |
| *—C(=O)—OMe | H | H | *—C(=O)—OMe | (I-39) |
| *—C(=O)—OEt | H | H | *—C(=O)—OEt | (I-40) |

Specific examples of the polymerizable compound (I) represented by Formula (I) shown above also include compounds represented by Formulae (I-41) to (I-53) shown below, and the like. In the formulae shown below, the group adjacent to an acryloyloxy group is a propylene group (a group obtained in a case where a methyl group is substituted with an ethylene group) and represents a mixture of position isomers having a methyl group in different positions.

| $Z_1$ | $Z_2$ | $Z_3$ | $Z_4$ | |
|---|---|---|---|---|
| $CH_3$ | $CH_3$ | H | H | (I-41) |
| $CH_3$ | H | H | $CH_3$ | (I-42) |
| $CH_3$ | $CH_3$ | $CH_3$ | $CH_3$ | (I-43) |
| F | F | F | F | (I-44) |
| Cl | Cl | Cl | Cl | (I-45) |
| Br | Br | Br | Br | (I-46) |
| $^tBu$ | H | H | $^tBu$ | (I-47) |
| *—C(Me)(Et)—Me | H | H | *—C(Me)(Et)—Me | (I-48) |
| *—C(Me)(Me)—CH$_2$—C(Me)(Me)—Me | H | H | *—C(Me)(Me)—CH$_2$—C(Me)(Me)—Me | (I-49) |
| CN | CN | H | H | (I-50) |
| *—C(=O)—OMe | H | H | *—C(=O)—OMe | (I-51) |
| *—C(=O)—OEt | H | H | *—C(=O)—OEt | (I-52) |
| $CH_3$ | $CH_3$ | $CH_3$ | H | (I-53) |

Specific examples of the polymerizable compound (I) represented by Formula (I) shown above also include compounds represented by Formulae (I-54) to (I-66) shown below, and the like.

| $Z_1$ | $Z_2$ | $Z_3$ | $Z_4$ | |
|---|---|---|---|---|
| $CH_3$ | $CH_3$ | H | H | (I-54) |
| $CH_3$ | H | H | $CH_3$ | (I-55) |
| $CH_3$ | $CH_3$ | $CH_3$ | $CH_3$ | (I-56) |
| F | F | F | F | (I-57) |
| Cl | Cl | Cl | Cl | (I-58) |
| Br | Br | Br | Br | (I-59) |
| $^tBu$ | H | H | $^tBu$ | (I-60) |
| Me | H | H | Me | (I-61) |
| *—C(Et)(Me)— | | | *—C(Et)(Me)— | |

-continued

| | | | | |
|---|---|---|---|---|
| *—C(Me)(Me)—CH₂—C(Me)(Me)—Me | H | H | *—C(Me)(Me)—CH₂—C(Me)(Me)—Me | (I-62) |
| CN | CN | H | H | (I-63) |
| *—C(=O)—OMe | H | H | *—C(=O)—OMe | (I-64) |
| *—C(=O)—OEt | H | H | *—C(=O)—OEt | (I-65) |
| CH₃ | CH₃ | CH₃ | H | (I-66) |

Specific examples of the polymerizable compound (I) represented by Formula (I) shown above also include compounds represented by Formulae (I-67) to (I-86) shown below, and the like

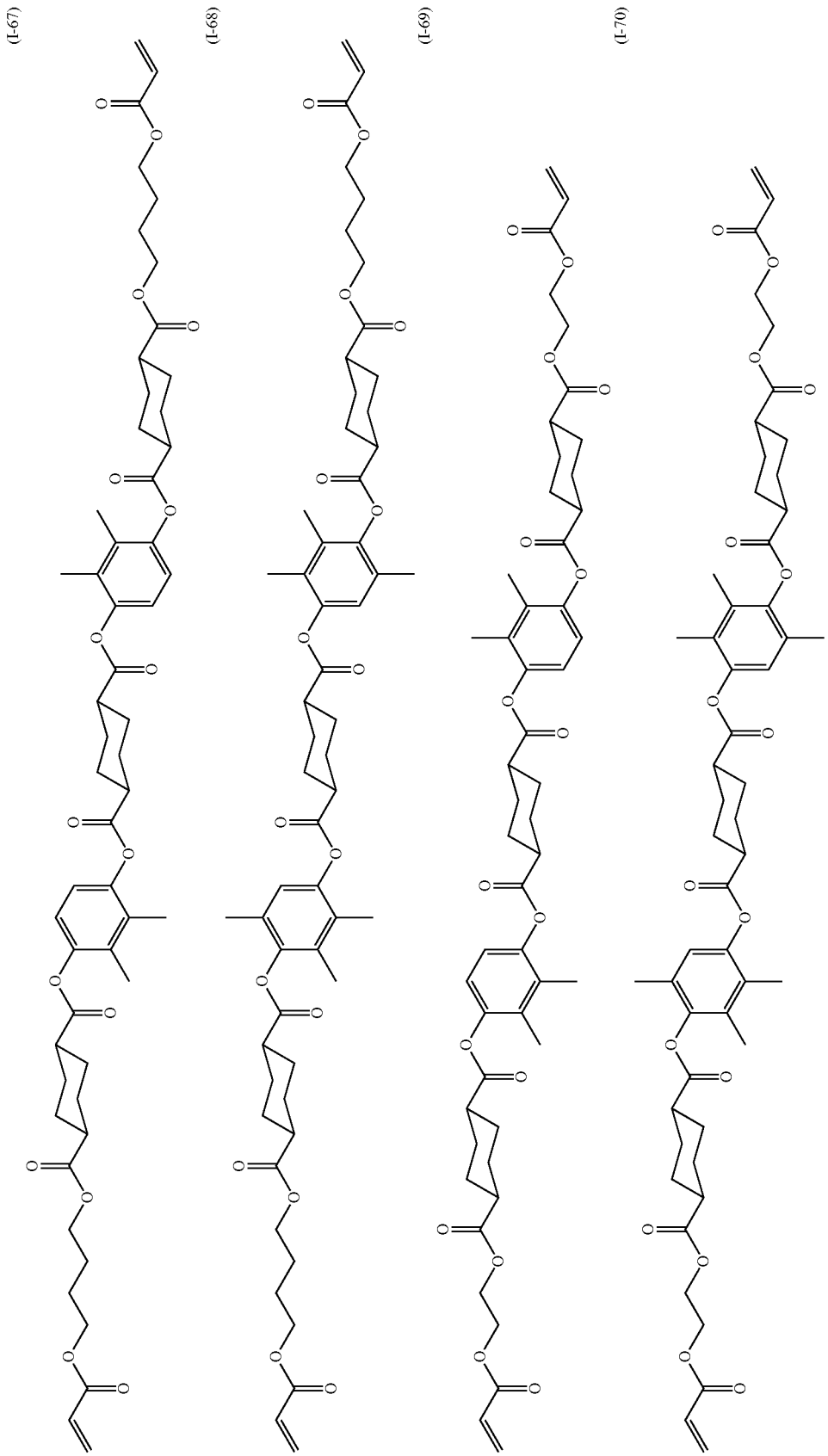

-continued
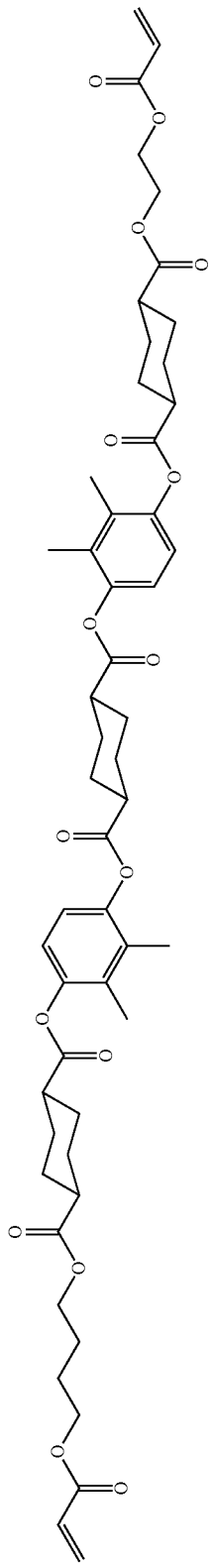
(I-71)
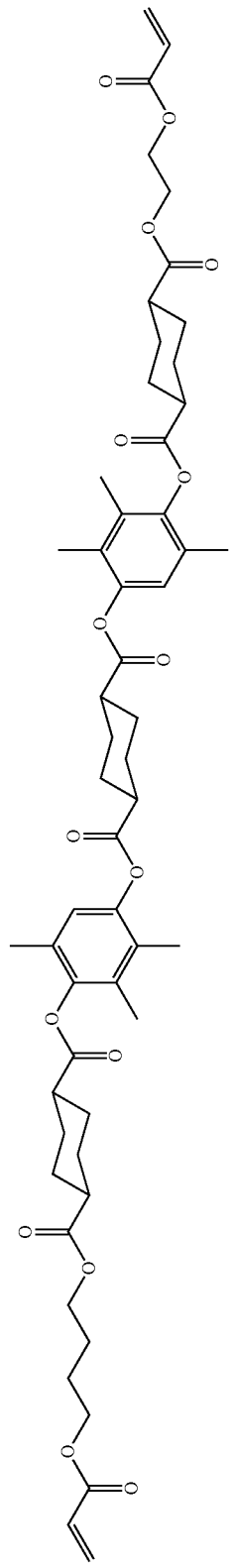
(I-72)
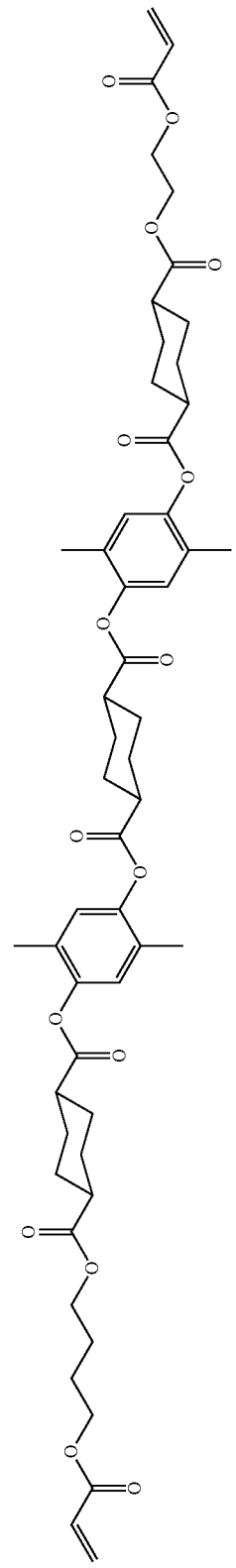
(I-73)
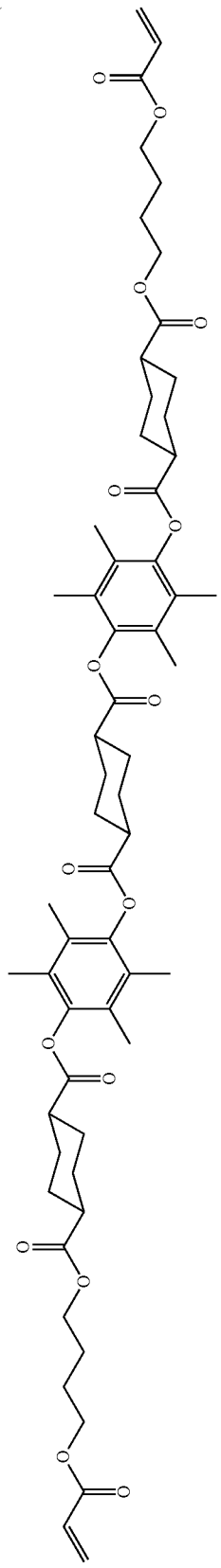
(I-74)

-continued
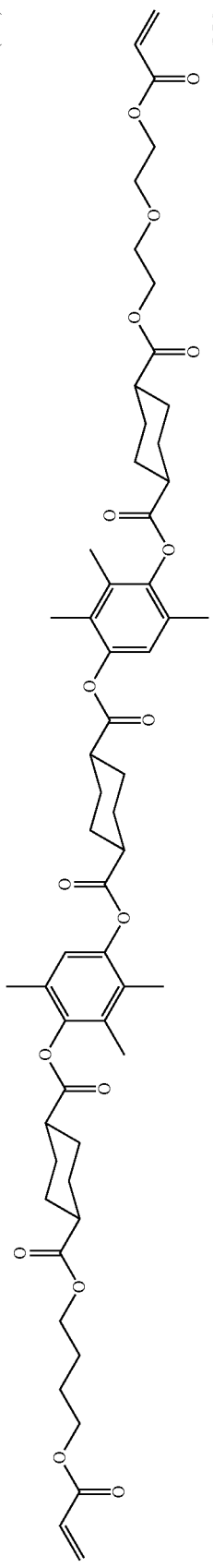
(I-75)
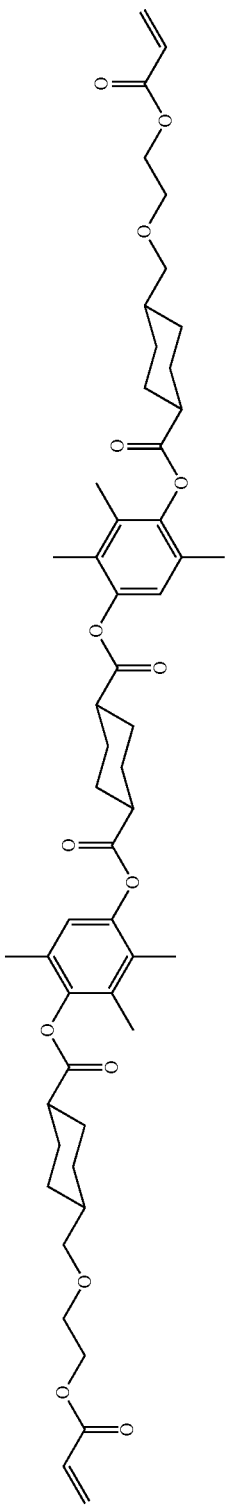
(I-76)
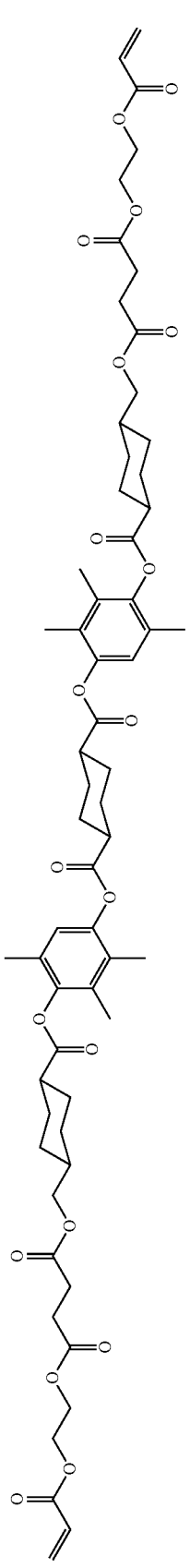
(I-77)
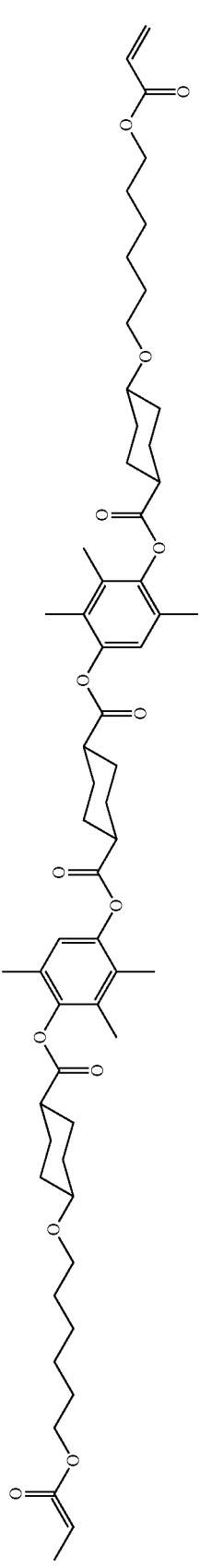
(I-78)

-continued
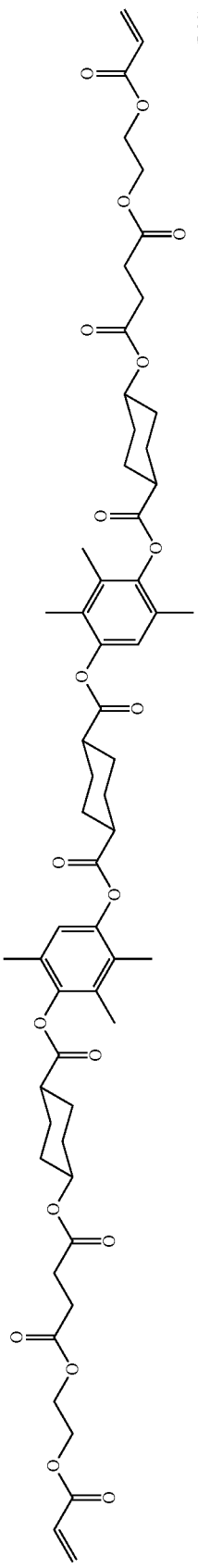
(I-79)
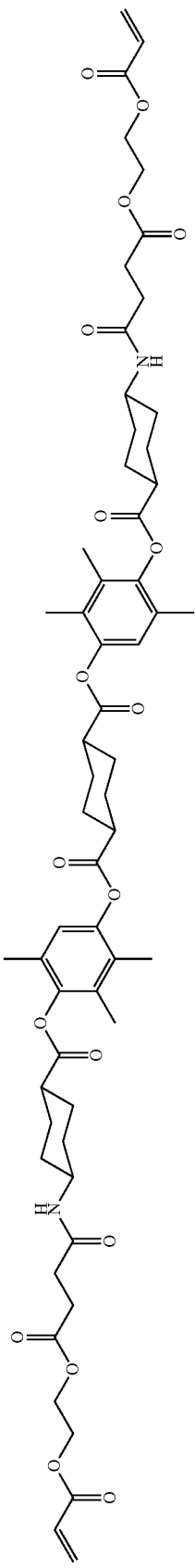
(I-80)
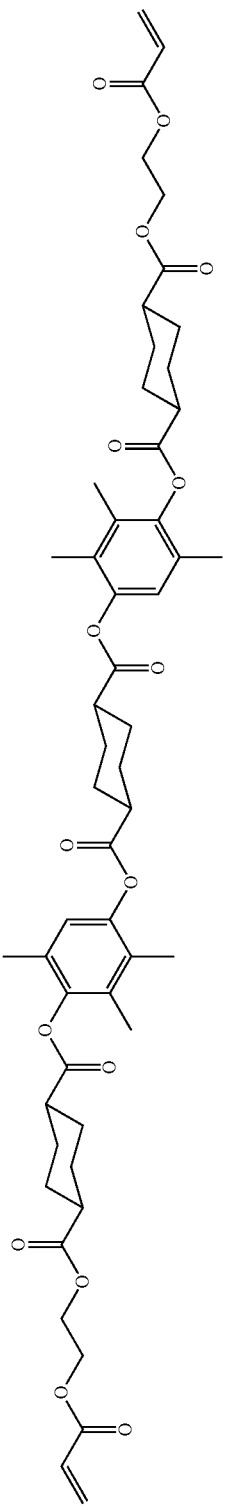
(I-81)
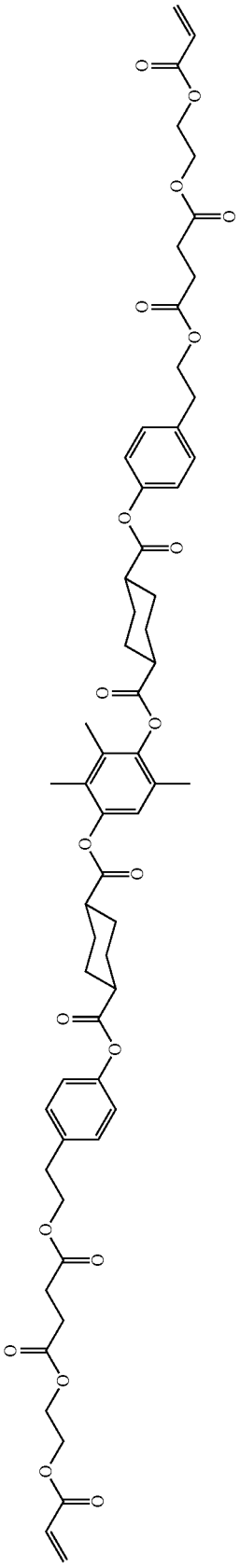
(I-82)

-continued
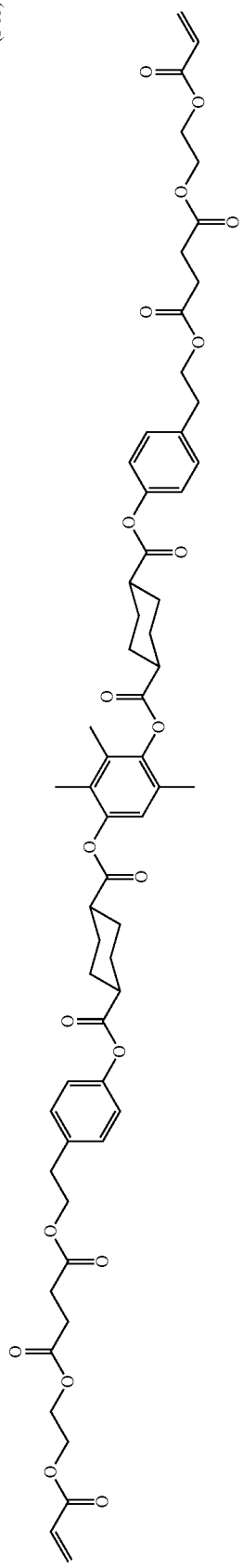
(I-83)
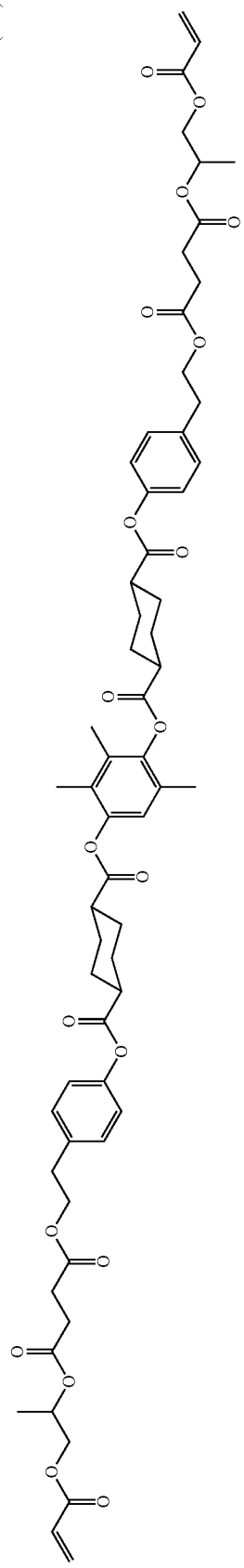
(I-84)
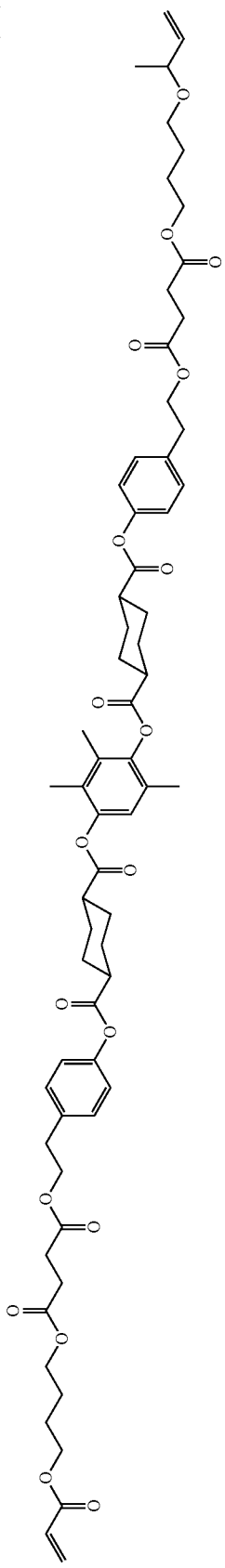
(I-85)
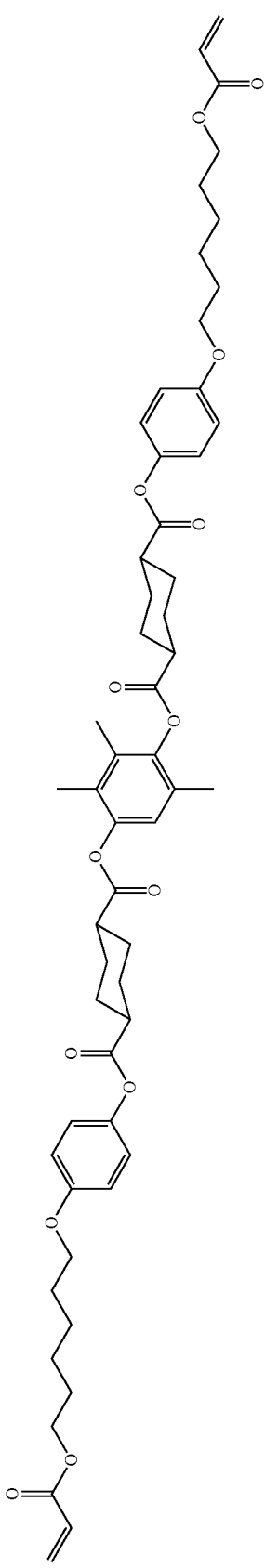
(I-86)

<Liquid Crystal Compound (II)>

The polymerizable liquid crystal composition forming the optically-anisotropic layer contains the liquid crystal compound (II) which is represented by Formula (II) shown below and does not correspond to Formula (I) described above. In the present invention, a compound which is represented by Formula (II) shown below and corresponds to Formula described above is regarded as corresponding to the polymerizable compound

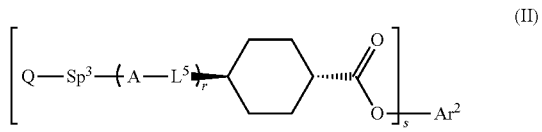

In Formula (II) shown above, $Ar^2$ represents an s-valent aromatic group.

$L^5$ represents a single bond, —COO—, or —OCO—, and A represents an aromatic ring having 6 or more carbon atoms or a cycloalkylene ring having 6 or more carbon atoms.

$Sp^3$ represents a single bond, a linear or branched alkylene group having 1 to 12 carbon atoms, or a divalent linking group obtained in a case where one or more —$CH_2$— groups constituting a linear or branched alkylene group having 1 to 12 carbon atoms are substituted with —O—, —S—, —NH—, —N(Q)-, or —CO—, and Q represents a polymerizable group.

r represents an integer of 0 to 2, s represents an integer of 1 or 2, and all of $L^5$, A, $Sp^3$, and Q, each of which become a plurality of groups depending on the number represented by r or s, may be the same as or different from each other.

In Formula (II) shown above, the aromatic group represented by $Ar^2$ is a group including a ring having aromaticity, and examples thereof include an s-valent group having at least one aromatic ring selected from the group consisting of an aromatic hydrocarbon ring and an aromatic heterocyclic ring, and the like. Examples of the aromatic hydrocarbon ring include a benzene ring, a naphthalene ring, an anthracene ring, a phenanthroline ring, and the like. Examples of the aromatic heterocyclic ring include a furan ring, a pyrrole ring, a thiophene ring, a pyridine ring, a thiazole ring, a benzothiazole ring, and the like. Among these, a benzene ring, a thiazole ring, and a benzothiazole ring are preferable.

Examples of the aromatic ring having 6 or more carbon atoms represented by A in Formula (II) shown above include the aromatic rings included in $Ar^2$ described above, and among these, a benzene ring (for example, a 1,4-phenyl group or the like) is preferable. Examples of the cycloalkylene ring having 6 or more carbon atoms represented by A in Formula (II) shown above include a cyclohexane ring, a cyclohexene ring, and the like. Among these, a cyclohexane ring (for example, a cyclohexane-1,4-diyl group or the like) is preferable.

Examples of the linear or branched alkylene group having 1 to 12 carbon atoms represented by $Sp^1$ in Formula (II) shown above suitably include a methylene group, an ethylene group, a propylene group, a butylene group, and the like.

Examples of the polymerizable group represented by Q in Formula (II) shown above include a (meth)acryloyl group, a vinyl group, a styryl group, an allyl group, and the like, "(Meth)acryloyl group" is a description representing an acryloyl group or a methacryloyl group.

In the present invention, as the liquid crystal compound represented by Formula (II) shown above, a compound is preferable which has at least three ring structures selected from the group consisting of a benzene ring and a cyclohexane ring, because such a compound easily expresses smectic properties by the quasi-phase separation between a rigid mesogen and a flexible side chain and exhibits sufficient rigidity.

In the present invention, as the liquid crystal compound represented by Formula (II) shown above, a compound having two or more polymerizable groups (for example, a (meth)acryloyl group, a vinyl group, a styryl group, an allyl group, and the like) is preferable, because such a compound further improves the durability of the optically-anisotropic layer.

In the present invention, the liquid crystal compound represented by Formula (II) shown above is preferably a liquid crystal compound exhibiting reciprocal wavelength dispersion properties.

In the present specification, the liquid crystal compound exhibiting "reciprocal wavelength dispersion properties" means that in a case where a value of in-plane retardation (Re) of a phase difference film prepared using the liquid crystal compound is measured at a specific wavelength (visible light region), the value of Re remains the same or increases as the measurement wavelength increases.

As the liquid crystal compound exhibiting reciprocal wavelength dispersion properties, a compound represented by Formula (II) shown above is preferable in which $Ar^2$ represents a divalent aromatic ring group represented by Formula (II-1), (II-2), (II-3), or (II-4) shown below.

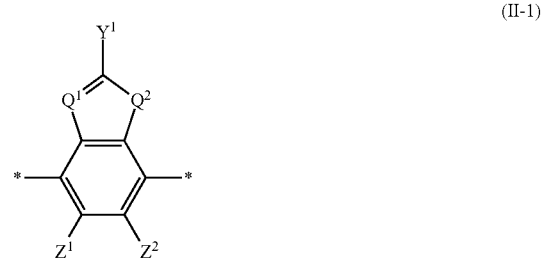

(II-1)

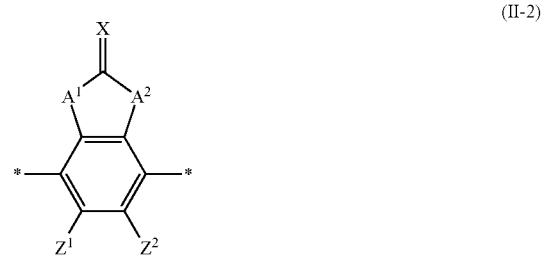

(II-2)

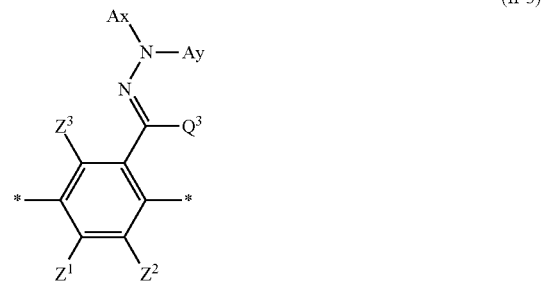

(II-3)

-continued

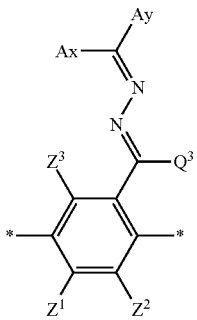

(II-4)

In Formulae (II-1) to (II-4) shown above, $Q^1$ represents N or CH, $Q^2$ represents —S—, —O—, or —$NR^{11}$—, $R^{11}$ represents a hydrogen atom or an alkyl group having 1 to 6 carbon atoms, and $Y^1$ represents an aromatic hydrocarbon group having 6 to 12 carbon atoms or an aromatic heterocyclic group having 3 to 12 carbon atoms that may have a substituent.

Specific examples of the alkyl group having 1 to 6 carbon atoms represented by $R^{11}$ include a methyl group, an ethyl group, a propyl group, an isopropyl group, a n-butyl group, an isobutyl group, a sec-butyl group, a tert-butyl group, a n-pentyl group, a n-hexyl group, and the like.

Examples of the aromatic hydrocarbon group having 6 to 12 carbon atoms represented by $Y^1$ include an aryl group such as a phenyl group, a 2,6-diethylphenyl group, or a naphthyl group.

Examples of the aromatic heterocyclic group having 3 to 12 carbon atoms represented by $Y^1$ include a heteroaryl group such as a thienyl group, a thiazolyl group, a furyl group, or a pyridyl group.

Examples of the substituent that $Y^1$ may have include a halogen atom, an alkyl group, a halogenated alkyl group, an alkenyl group, an aryl group, a cyano group, an amino group, a nitro group, a nitroso group, a carboxy group, an alkyl sulfinyl group having 1 to 6 carbon atoms, an alkyl sulfonyl group having 1 to 6 carbon atoms, a fluoroalkyl group having 1 to 6 carbon atoms, an alkoxy group having 1 to 6 carbon atoms, an alkyl sulfanyl group having 1 to 6 carbon atoms, a N-alkylamino group having 1 to 6 carbon atoms, a N,N-dialkylamino group having 2 to 12 carbon atoms, a N-alkylsulfamoyl group having 1 to 6 carbon atoms, a N,N-dialkylsulfamoyl group having 2 to 12 carbon atoms, a group obtained by combining these, and the like.

In Formulae (II-1) to (II-4) shown above, $Z^1$, $Z^2$, and $Z^3$ each independently represent a hydrogen atom, a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$NR^{12}R^{13}$, or —$SR^{14}$. $R^{12}$ to $R^{14}$ each independently represent a hydrogen atom or an alkyl group having 1 to 6 carbon atoms, and $Z^1$ and $Z^2$ may form an aromatic ring by being bonded to each other.

The monovalent aliphatic hydrocarbon group having 1 to 20 carbon atoms is preferably an alkyl group having 1 to 15 carbon atoms, and more preferably an alkyl group having 1 to 8 carbon atoms. Specifically, a methyl group, an ethyl group, an isopropyl group, a tert-pentyl group (1,1-dimethylpropyl group), a tort-butyl group, and a 1,1-dimethyl-3,3-dimethyl-butyl group are even more preferable, and a methyl group, an ethyl group, and a tert-butyl group are particularly preferable.

Examples of the monovalent alicyclic hydrocarbon group having 3 to 20 carbon atoms include a monocyclic saturated hydrocarbon group such as a cyclopropyl group, a cyclobutyl group, a cyclopentyl group, a cyclohexyl group, a cycloheptyl group, a cyclooctyl group, a cyclodecyl group, a methylcyclohexyl group, or an ethylcyclohexyl group; a monocyclic unsaturated hydrocarbon group such as a cyclobutenyl group, a cyclopentenyl group, a cyclodecenyl group, a cycloheptenyl group, a cyclooctenyl group, a cyclodecenyl group, a cyclopentadienyl group, a cyclohexadienyl group, a cyclooctadienyl group, or cyclodecadienyl group; a polycyclic saturated hydrocarbon group such as a bicyclo[2.2.1]heptyl group, a bicyclo[2.2.2]octyl group, a tricyclo[5.2.1.0$^{2,6}$]decyl group, a tricyclo[3.3.1.1$^{3,7}$]decyl group, a tetracyclo[6.2.1.1$^{3,6}$.0$^{2,7}$]dodecyl group, or an adamantyl group; and the like.

Specific examples of the monovalent aromatic hydrocarbon group having 6 to 20 carbon atoms include a phenyl group, a 2,6-diethylphenyl group, a naphthyl group, a biphenyl group, and the like. Among these, an aryl group (particularly a phenyl group) having 6 to 12 carbon atoms is preferable.

Examples of the halogen atom include a fluorine atom, a chlorine atom, a bromine atom, an iodine atom, and the like. Among these, a fluorine atom, a chlorine atom, and a bromine atom are preferable.

Specific examples of the alkyl group having 1 to 6 carbon atoms represented by $R^5$ to $R^7$ include a methyl group, an ethyl group, a propyl group, an isopropyl group, a n-butyl group, an isobutyl group, a sec-butyl group, a tea-butyl group, a n-pentyl group, a n-hexyl group, and the like.

In Formula (II-2) shown above, $A^1$ and $A^2$ each independently represent a group selected from the group consisting of —O—, —N($R^{15}$), —S—, and —CO—, and $R^{15}$ represents a hydrogen atom or a substituent.

Examples of the substituent represented by $R^{15}$ are the same as the examples of the substituent that $Y^1$ in Formula (II-1) shown above may have.

In Formula (II-2) shown above, X represents a hydrogen atom or a nonmetal atom in Group 14 to 16 which may be bonded to a substituent.

Examples of the nonmetal atom in Group 14 to 16 represented by X include an oxygen atom, a sulfur atom, a nitrogen atom having a substituent, and a carbon atom having a substituent. Examples of the substituent are the same as the examples of the substituent that $Y^1$ in Formula (II-1) shown above may have.

In Formulae (II-3) and (II-4) shown above, Ax represents an organic group having 2 to 30 carbon atoms that has at least one aromatic ring selected from the group consisting of an aromatic hydrocarbon ring and an aromatic heterocyclic ring.

In Formulae (Ar-3) to (Ar-4) shown above, Ay represents a hydrogen atom, an alkyl group having 1 to 6 carbon atoms that may have a substituent, or an organic group having 2 to 30 carbon atoms that has at least one aromatic ring selected from the group consisting of an aromatic hydrocarbon ring and an aromatic heterocyclic ring.

The aromatic ring represented by Ax and Ay may have a substituent, and Ax and Ay may form a ring by being bonded to each other.

$Q^3$ represents a hydrogen atom or an alkyl group having 1 to 6 carbon atoms that may have a substituent.

Examples of Ax and Ay include those described in paragraphs "0039" to "0095" in WO2014/010325A.

Specific examples of the alkyl group having 1 to 6 carbon atoms represented by $Q^3$ include a methyl group, an ethyl group, a propyl group, an isopropyl group, a n-butyl group, an isobutyl group, a sec-butyl group, a tort-butyl group, a n-pentyl group, a n-hexyl group, and the like. Examples of the substituent are the same as the examples of the substituent that $Y^1$ in Formula (II-1) shown above may have.

Preferred examples of the liquid crystal compound represented by Formulae (II-1) to (II-4) shown above will be shown below, but the liquid crystal compound is not limited to these compounds. All of 1,4-cyclohexylene groups in the following formulae are a trans-1,4-cyclohexylene group.

| No | Y1 | n | No | Y1 | n |
|---|---|---|---|---|---|
| II-1-1 | phenyl | 6 | II-1-9 | 2-thienyl | 6 |
| II-1-2 | 4-cyanophenyl (CN) | 6 | II-1-10 | 2-methyl-4-nitrophenyl (NO₂) | 6 |
| II-1-3 | 4-nitrophenyl (NO₂) | 6 | II-1-11 | 4,6-dimethylbenzofuran-2-yl | 6 |
| II-1-4 | 4-pyridyl | 6 | II-1-12 | 2-furyl | 6 |
| II-1-5 | 4-(styryl)phenyl | 6 | II-1-13 | 5-chloro-2-thienyl | 6 |
| II-1-6 | 4-nitrophenyl (NO₂) | 11 | II-1-14 | 1,3-thiazol-5-yl | 6 |

| | | | | | |
|---|---|---|---|---|---|
| II-1-7 | 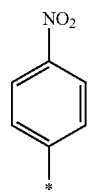 [SMILES: *c1ccc([N+](=O)[O-])cc1] | 8 | II-1-15 | 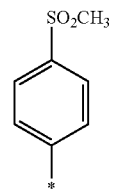 | 6 |
| II-1-8 | 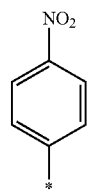 [SMILES: *c1ccc([N+](=O)[O-])cc1] | 4 | | | |
II-1-16
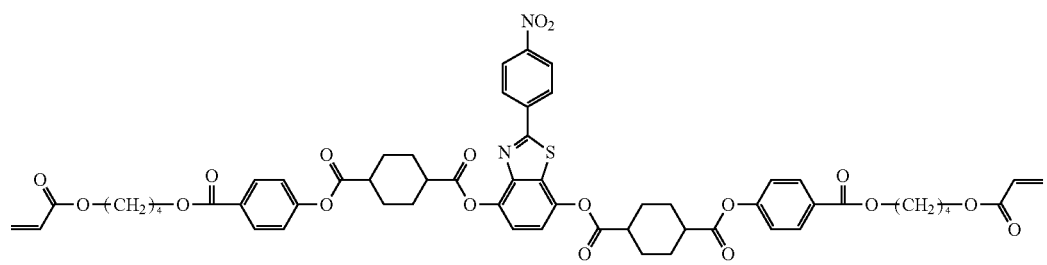
II-1-17
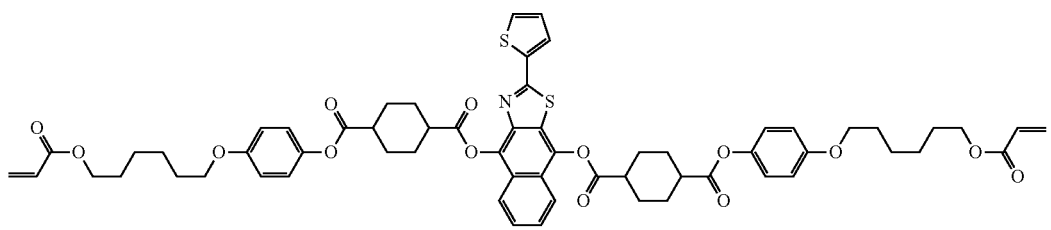 [SMILES: C=CC(=O)OCCCCCCOc1ccc(OC(=O)C2CCC(C(=O)Oc3c4ccccc4c(OC(=O)C4CCC(C(=O)Oc5ccc(OCCCCCCOC(=O)C=C)cc5)CC4)c4sc(-c5cccs5)nc34)CC2)cc1]
II-1-18
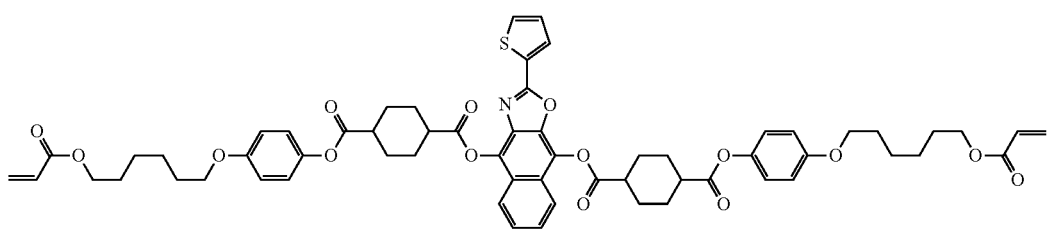
| No | X | R1 | No | X | R1 |
|---|---|---|---|---|---|
| II-2-1 | 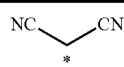 | H | II-2-5 | 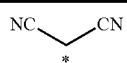 | H |
| II-2-2 | 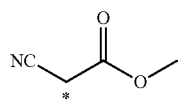 | H | II-26 | 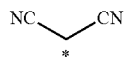 | H |

-continued

| No | (structure) | |
|---|---|---|
| II-2-3 | NC-CH₂-C(=O)-O-butyl (* on CH₂) | H |
| II-2-4 | NC-CH₂-C(=O)-O-CH₂CH₂-O-C(CH₃)₂-OH (* on CH₂) | H |
| II-2-7 | S | H |

In the above formulae, "*" represents a binding position.

(Structure: acrylate-O-(CH₂)₅-O-phenyl-O-C(=O)-cyclohexyl-C(=O)-O-phenyl[with C(=N-N(Ax)(Ay))-Q2 substituent]-O-C(=O)-cyclohexyl-C(=O)-O-phenyl-O-(CH₂)₅-O-acrylate)

| No | Ax | Ay | Q2 |
|---|---|---|---|
| II-3-1 | benzothiazol-2-yl | H | H |
| II-3-2 | benzoxazol-2-yl | H | H |
| II-3-3 | naphthalen-1-yl | H | H |
| II-3-4 | Ph | Ph | H |
| II-3-5 | quinolin-2-yl | H | H |
| II-3-6 | phthalazin-1-yl | H | H |
| II-3-7 | benzothiazol-2-yl | $CH_3$ | H |
| II-3-8 | benzothiazol-2-yl | $C_4H_9$ | H |
| II-3-9 | benzothiazol-2-yl | $C_6H_{13}$ | H |

-continued
| | | | |
|---|---|---|---|
| II-3-10 | 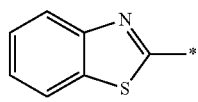 [SMILES: *c1nc2ccccc2s1] | 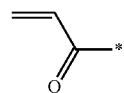 [SMILES: *C(=O)C=C] | H |
| II-3-11 | 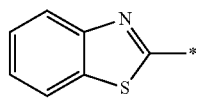 [SMILES: *c1nc2ccccc2s1] | 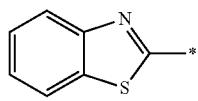 [SMILES: *c1nc2ccccc2s1] | H |
| II-3-12 | 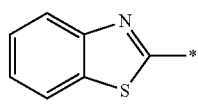 | CH$_2$CN | H |
| II-3-13 | 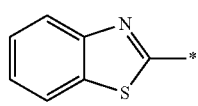 | 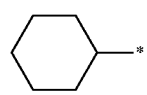 [SMILES: *C1CCCCC1] | H |
| II-3-14 | 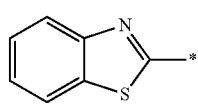 [SMILES: *c1nc2ccccc2s1] | 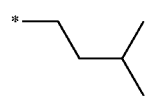 | H |
| II-3-15 | 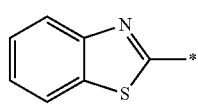 [SMILES: *c1nc2ccccc2s1] | CH$_2$CH$_2$OH | H |
| II-3-16 | 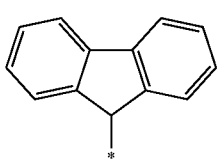 [SMILES: *C1c2ccccc2-c2ccccc21] | H | H |
| II-3-17 | 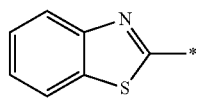 | CH$_2$CF$_3$ | H |
| II-3-18 | 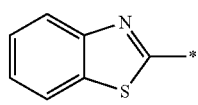 [SMILES: *c1nc2ccccc2s1] | H | CH$_3$ |
| II-3-19 | 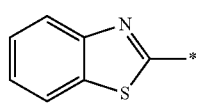 [SMILES: *c1nc2ccccc2s1] | 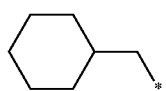 | H |
| II-3-20 | 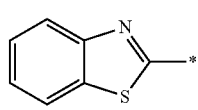 | 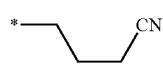 | H |
| II-3-21 | 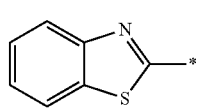 [SMILES: *c1nc2ccccc2s1] | 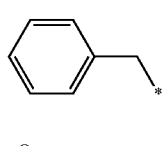 | H |
| II-3-22 | 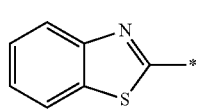 | 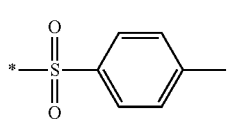 | H |

| | | | |
|---|---|---|---|
| II-3-23 | 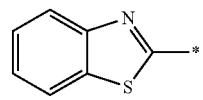 | 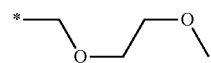 | H |
| II-3-24 | 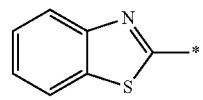 | 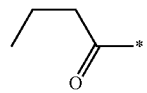 [SMILES: *C(=O)CCC] | H |
| II-3-25 | 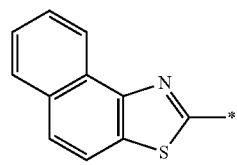 [SMILES: *c1nc2c(ccc3ccccc32)s1] | $C_6H_{13}$ | H |
| II-3-26 | 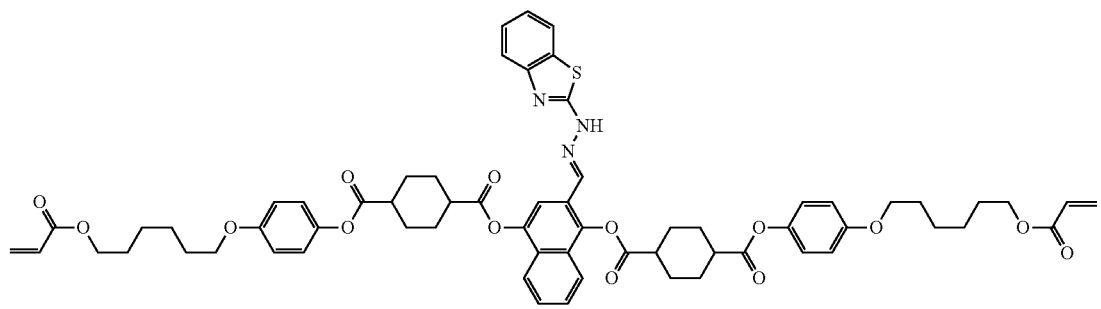 [SMILES: C=CC(=O)OCCCCCCOc1ccc(OC(=O)C2CCC(C(=O)Oc3cc(/C=N/Nc4nc5ccccc5s4)c(OC(=O)C4CCC(C(=O)Oc5ccc(OCCCCCCOC(=O)C=C)cc5)CC4)c4ccccc34)CC2)cc1] | | |
| II-3-27 | 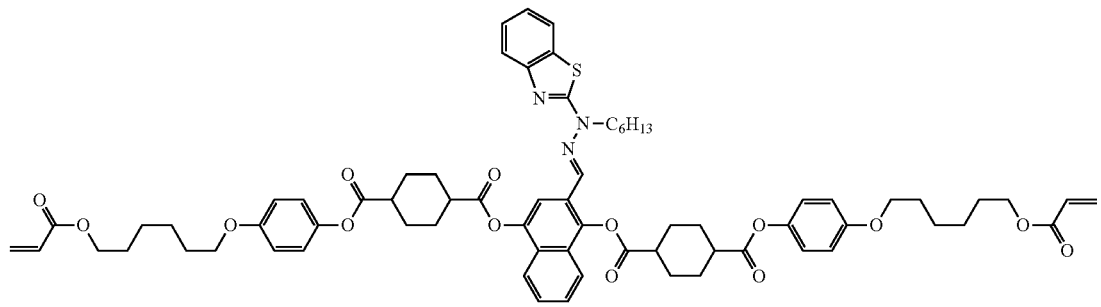 | | |
| II-3-28 | 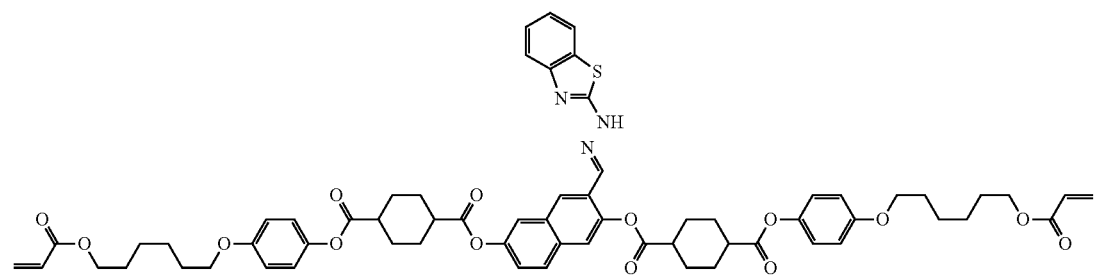 | | |
| II-3-29 | 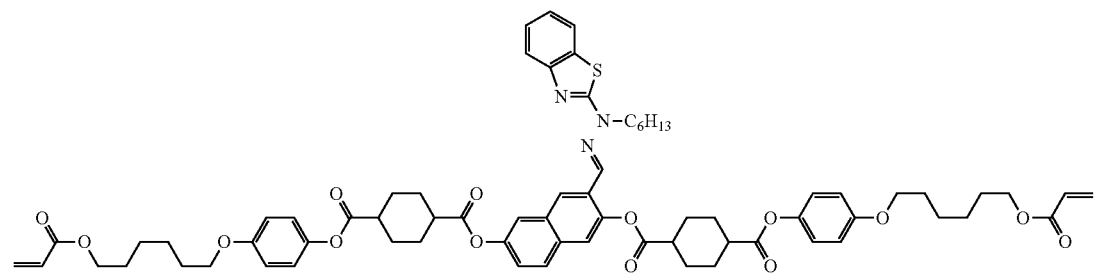 | | |

-continued
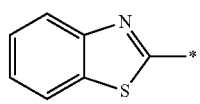
| No | Ax | Ay | Q2 |
|---|---|---|---|
| II-3-30 | 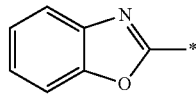 | H | H |
| II-3-31 | 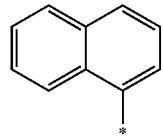 | H | H |
| II-3-32 | 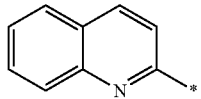 [SMILES: *c1ccc2ccccc2n1] | H | H |
| II-3-33 | Ph | Ph | H |
| II-3-34 | 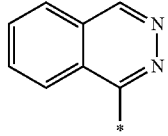 [SMILES: *c1nncc2ccccc12] | H | H |
| II-3-35 | 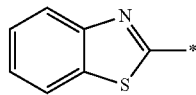 [SMILES: *c1nc2ccccc2s1] | H | H |
| II-3-36 | 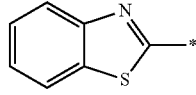 [SMILES: *c1nc2ccccc2s1] | CH$_3$ | H |
| II-3-37 | 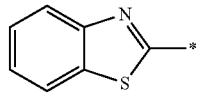 | C$_4$H$_9$ | H |
| II-3-38 | 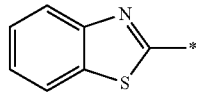 | C$_6$H$_{13}$ | H |
| II-3-39 | 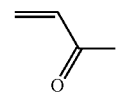 | 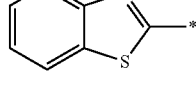 | H |
| II-3-40 | 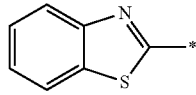 |  | H |

-continued

| | | | |
|---|---|---|---|
| II-3-41 | benzothiazol-2-yl | CH₂CN | H |
| II-3-42 | benzothiazol-2-yl | cyclohexyl | H |
| II-3-43 | benzothiazol-2-yl | isopentyl | H |
| II-3-44 | benzothiazol-2-yl | CH₂CH₂OH | H |
| II-3-45 | fluoren-9-yl | H | H |
| II-3-46 | benzothiazol-2-yl | CH₂CF₃ | H |
| II-3-47 | benzothiazol-2-yl | H | CH₃ |
| II-3-47 | benzothiazol-2-yl | cyclohexylmethyl | H |
| II-3-49 | benzothiazol-2-yl | -(CH₂)₃CN | H |
| II-3-50 | benzothiazol-2-yl | benzyl | H |
| II-3-51 | benzothiazol-2-yl | p-tolylsulfonyl | H |
| II-3-52 | benzothiazol-2-yl | -CH₂CH₂OCH₂CH₂OCH₃ | H |
| II-3-53 | benzothiazol-2-yl | butanoyl | H |

| | | | |
|---|---|---|---|
| II-3-54 | 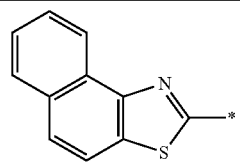 | C$_6$H$_{13}$ | H |
II-3-55
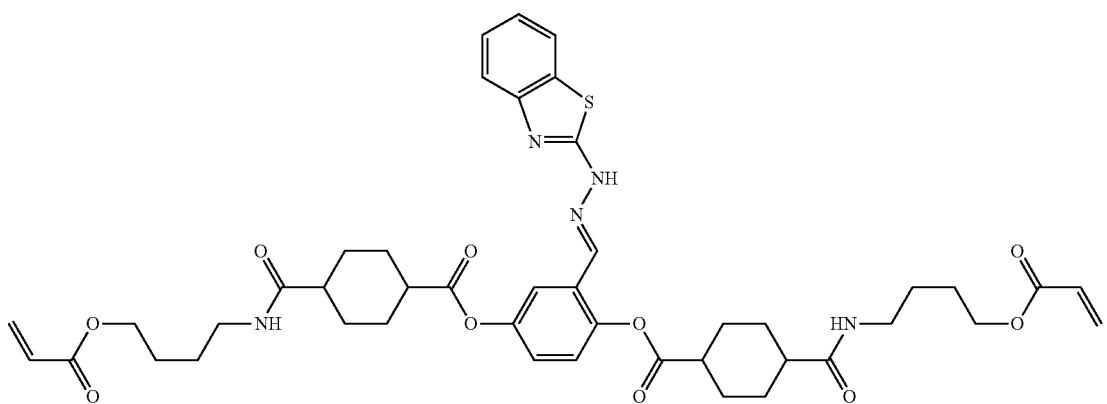 [SMILES: C=CC(=O)OCCCCNC(=O)C1CCC(C(=O)Oc2ccc(OC(=O)C3CCC(C(=O)NCCCCOC(=O)C=C)CC3)c(/C=N/Nc3nc4ccccc4s3)c2)CC1]
II-4-1
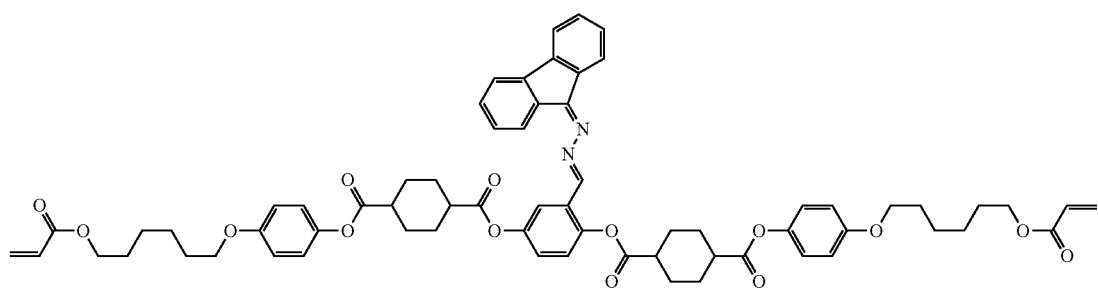 [SMILES: C=CC(=O)OCCCCCCOc1ccc(OC(=O)C2CCC(C(=O)Oc3ccc(OC(=O)C4CCC(C(=O)Oc5ccc(OCCCCCCOC(=O)C=C)cc5)CC4)c(/C=N/N=C4c5ccccc5-c5ccccc54)c3)CC2)cc1]
II-4-2
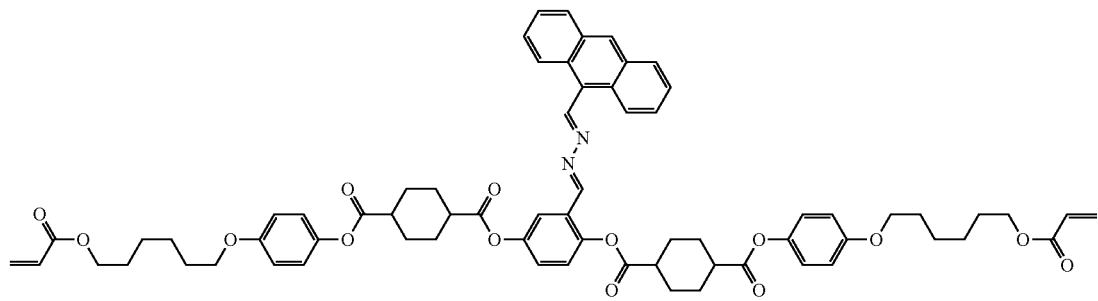 [SMILES: C=CC(=O)OCCCCCCOc1ccc(OC(=O)C2CCC(C(=O)Oc3ccc(OC(=O)C4CCC(C(=O)Oc5ccc(OCCCCCCOC(=O)C=C)cc5)CC4)c(/C=N/N=C/c4c5ccccc5cc5ccccc45)c3)CC2)cc1]
II-4-3
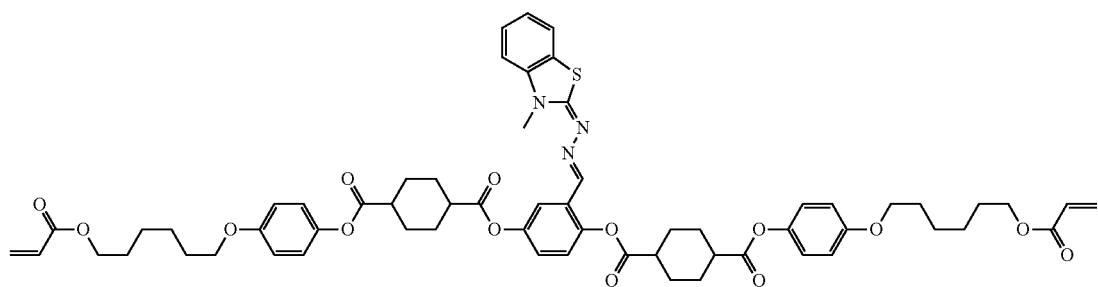 [SMILES: C=CC(=O)OCCCCCCOc1ccc(OC(=O)C2CCC(C(=O)Oc3ccc(OC(=O)C4CCC(C(=O)Oc5ccc(OCCCCCCOC(=O)C=C)cc5)CC4)c(/C=N/N=c4/sc5ccccc5n4C)c3)CC2)cc1]

In the present invention, the liquid crystal compound represented by Formula (II) shown above is preferably a compound represented by Formula (II) shown above in which $Ar^2$ is represented by General Formula (II-2) described above, and specifically more preferably a compound represented by Formula (II) shown above in which n is 2 and $Ar^2$ is represented by. Formula (2a) shown below, because such a compound further improves the durability of the optically-anisotropic layer by causing electronic interaction between liquid crystal molecules.

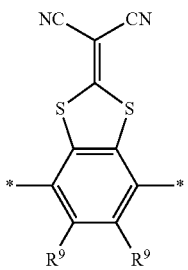

(2a)

In Formula (2a) shown above, represents a binding position, and $R^9$ each independently represents a hydrogen atom or an alkyl group having 1 to 6 carbon atoms.

Examples of the compound represented by Formula (II) shown above, in which n is 2 and $Ar^2$ is represented by Formula (2a) shown above, include a compound represented by Formula L-1 shown below, a compound represented by Formula L-2 shown below, and the like. Examples thereof include a compound represented by Formula L-1 shown below (liquid crystal compound L-1), a compound represented by Formula L-2 shown below (liquid crystal compound L-2), a compound represented by Formula L-3 shown below (liquid crystal compound L-3), a compound represented by Formula L-4 shown below (liquid crystal compound L-4), a compound represented by Formula L-5 shown below (liquid crystal compound L-5), and the like. The group adjacent to an acryloyloxy group in Formulae L-1 and L-2 shown below is a propylene group (group obtained in a case where a methyl group is substituted with an ethylene group), and the liquid crystal compounds L-1 and L-2 represent a mixture of position isomers having a methyl group in different positions. In Formulae L-1 to L-5 shown below, all of the 1,4-cyclohexylene groups are a trans-1,4-cyclohexylene group.

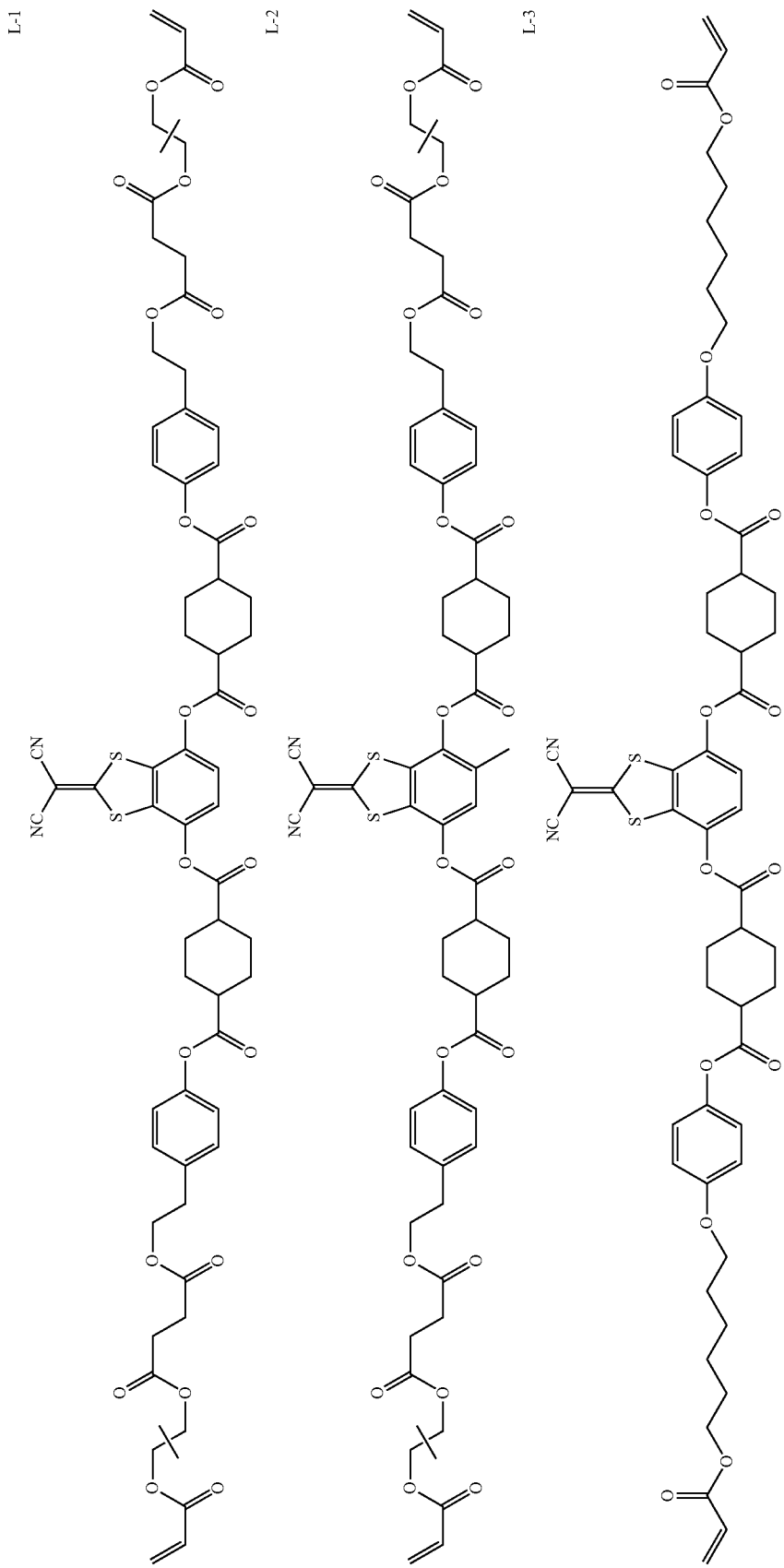

-continued
L-4
L-5
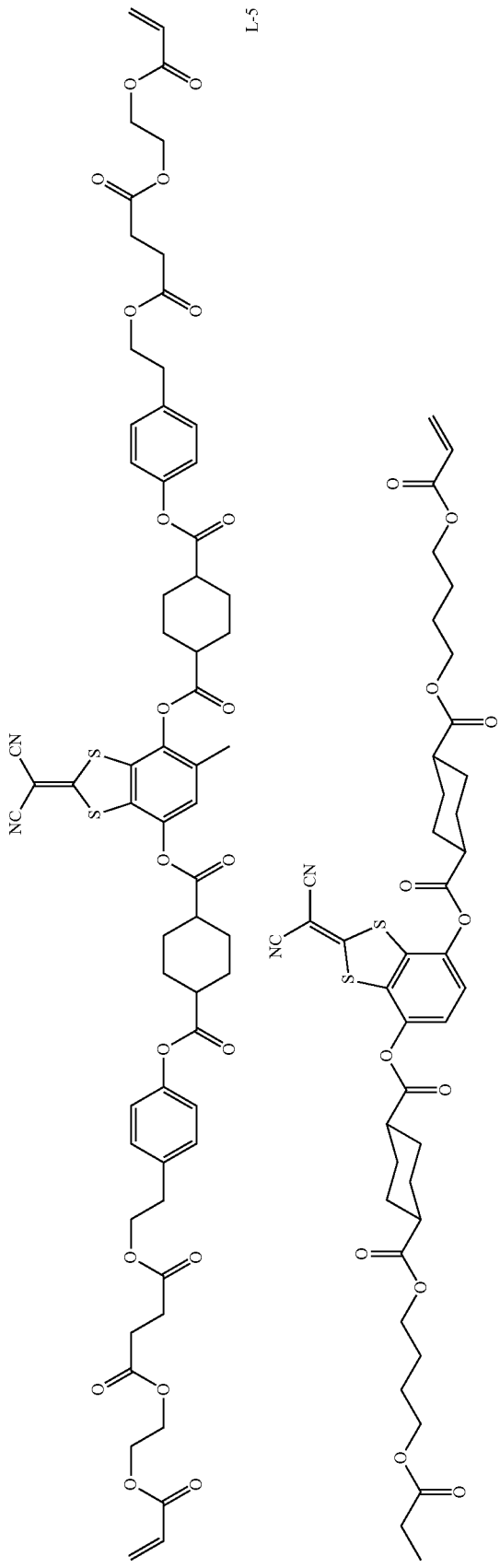

<Polymerization Initiator>

The polymerizable liquid crystal composition forming the optically-anisotropic layer contains a polymerization initiator.

The polymerization initiator to be used is preferably a photopolymerization initiator which can initiate a polymerization reaction by being irradiated with ultraviolet rays.

Examples of the photopolymerization initiator include α-carbonyl compounds (described in the specifications of U.S. Pat. Nos. 2,367,661B and 2,367,670B), acyloin ethers (described in the specification of U.S. Pat. No. 2,448,828B), α-hydrocarbon-substituted aromatic acyloin compounds (described in the specification of U.S. Pat. No. 2,722,512B), polynuclear quinone compounds (described in the specifications of U.S. Pat. Nos. 3,046,127B and 2,951,758B), a combination of a triaryl imidazole dimer and p-aminophenylketone (described in the specification of U.S. Pat. No. 3,549,367B), acridine and phenazine compounds (described in the specifications of JP1985-105667A (JP-S60-105667A) and U.S. Pat. No. 4,239,850B), oxadiazole compounds (described in the specification of U.S. Pat. No. 4,212,970B), acylphosphine oxide compounds (described in the specifications of JP1988-40799B (JP-S63-40799B), JP1993-29234B (JP-H05-29234B), JP1998-95788A (JP-H10-95788A), and JP1998-29997 A (JP-H10-29997A)), and the like.

In the present invention, the polymerization initiator is preferably an oxime-type polymerization initiator and specifically more preferably a polymerization initiator represented by Formula (III) shown below, because such a polymerization initiator further improves the durability of the optically-anisotropic layer.

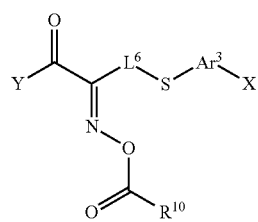

(III)

In Formula alp shown above, X represents a hydrogen atom or a halogen atom, and Y represents a monovalent organic group.

$Ar^3$ represents a divalent aromatic group, $L^6$ represents a divalent organic group having 1 to 12 carbon atoms, and $R^{10}$ represents an alkyl group having 1 to 12 carbon atoms.

Examples of the halogen atom represented by X in Formula (III) shown above include a fluorine atom, a chlorine atom, a bromine atom, an iodine atom, and the like. Among these, a chlorine atom is preferable.

Examples of the divalent aromatic group represented by $Ar^3$ in Formula (III) shown above include a divalent group having at least one aromatic ring selected from the group consisting of the aromatic hydrocarbon ring and the aromatic heterocyclic ring exemplified as $Ar^2$ in Formula (II) shown above, and the like.

Examples of the divalent organic group having 1 to 12 carbon atoms represented by in Formula (III) shown above include a linear or branched alkylene group having 1 to 12 carbon atoms. Specific examples thereof suitably include a methylene group, an ethylene group, a propylene group, and the like.

Specific examples of the alkyl group having 1 to 12 carbon atoms represented by $R^{10}$ in Formula (III) shown above suitably include a methyl group, an ethyl group, a propyl group, and the like.

Examples of the monovalent organic group represented by Y in Formula (III) shown above include a functional group having a benzophenone skeleton (($C_6H_5$)$_2$CO). Specifically, functional groups having a benzophenone skeleton, such as the groups represented by Formulae (3a) and (3b) shown below, are preferable in which the terminal benzene ring is unsubstituted or substituted with one substituent.

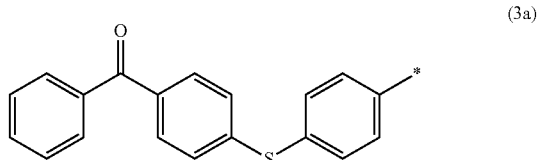

(3a)

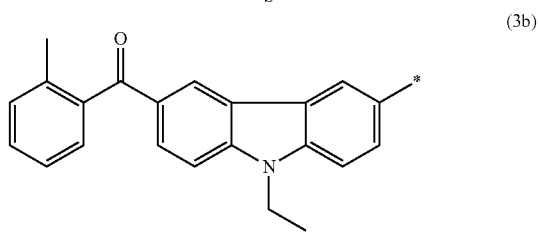

(3b)

In Formulae (3a) and (3b) shown above, * represents a binding position, that is, a position bonded to a carbon atom of the carbonyl group in Formula (III) shown above.

Examples of the oxime-type polymerization initiator represented by Formula (III) shown above include a compound represented by Formula S-1 shown below, a compound represented by Formula S-2 shown below, and the like.

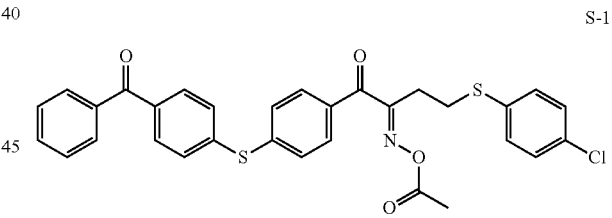

S-1

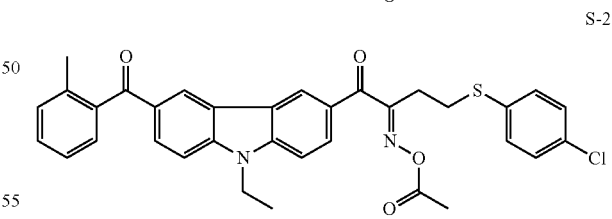

S-2

In the present invention, the content of the aforementioned polymerization initiator is not particularly limited, but is preferably 0.01% to 20% by mass and more preferably 0.5% to 5% by mass with respect to the solid content of the polymerizable liquid crystal composition.

<Other Polymerizable Compounds>

The polymerizable liquid crystal composition forming the optically-anisotropic layer may contain other polymerizable compounds in addition to the polymerizable compound (I) represented by Formula (I) described above.

The polymerizable group that the aforementioned other polymerizable compounds have is not particularly limited, and examples thereof include a (meth)acryloyl group, a vinyl group, a styryl group, an allyl group, and the like. Among these, a (meth)acryloyl group is preferable.

In the present invention, the aforementioned other polymerizable compounds are preferably polymerizable compounds having 2 to 4 polymerizable groups and more preferably polymerizable compounds having 2 polymerizable groups, because such polymerizable compounds further improve the durability of the optically-anisotropic layer.

Examples of the aforementioned other polymerizable compounds include the compounds represented by Formulae (M1), (M2), and (M3) described in paragraphs "0030" to "0033" in JP2014-077068A. More specifically, examples thereof include specific examples described in paragraphs "0046" to "0055" in JP2014-077068A.

<Organic Solvent>

From the viewpoint of workability for forming the optically-anisotropic layer, it is preferable that the polymerizable liquid crystal composition forming the optically-anisotropic layer contains an organic solvent.

Specific examples of the organic solvent include ketones (for example, acetone, 2-butanone, methyl isobutyl ketone, cyclohexanone, and the like), ethers (for example, dioxane, tetrahydrofuran, and the like), aliphatic hydrocarbons (for example, hexane and the like), alicyclic hydrocarbons (for example, cyclohexane and the like), aromatic hydrocarbons (for example, toluene, xylene, trimethyl benzene, and the like), halogenated hydrocarbons (for example, dichloromethane, dichloroethane, dichlorobenzene, chlorotoluene, and the like), esters (for example, methyl acetate, ethyl acetate, butyl acetate, and the like), water, alcohols (for example, ethanol, isopropanol, butanol, cyclohexanol, and the like), cellosolves (for example, methyl cellosolve, ethyl cellosolve, and the like), cellosolve acetates, sulfoxides (for example, dimethyl sulfoxide and the like), amides (for example, dimethylformamide, dimethylacetamide, and the like), and the like. One kind of these may be used singly, or two or more kinds of these may be used in combination.

In the present invention, the optically-anisotropic layer can be formed, for example, by a method in which a desired alignment state is created using the polymerizable liquid crystal composition, which contains the polymerizable compound (I), the liquid crystal compound (II), and the polymerization initiator described above as well as other polymerizable compounds optionally used, an organic solvent, and the like, and fixing the alignment state by polymerization.

The polymerization conditions are not particularly limited. However, in a case where polymerization is performed by light irradiation, it is preferable to use ultraviolet rays. The irradiation amount is preferably 10 mJ/cm$^2$ to 50 mJ/cm$^2$, more preferably 20 mJ/cm$^2$ to 5 mJ/cm$^2$, even more preferably 30 mJ/cm$^2$ to 3 J/cm$^2$, and particularly preferably 50 mJ/cm$^2$ to 1,000 J/cm$^2$. Furthermore, in order to accelerate the polymerization reaction, polymerization may be performed under heating conditions.

In the present invention, the optically-anisotropic layer can be formed on any support which will be described later or on a polarizer in the polarizing plate of the present invention that will be described later.

In the present invention, the optically-anisotropic layer is preferably a layer obtained by aligning the aforementioned polymerizable liquid crystal composition in a smectic phase and then polymerizing the composition (fixing the alignment), because then the durability of the optically-anisotropic layer is further improved. Presumably, because the gravity centers of liquid crystal molecules are more regularly arranged in a smectic phase than in a nematic phase, the hydrolysis described above may not easily occur due to the structure around the ester bond, and hence the durability of the optically-anisotropic layer may be further improved.

From the viewpoint of imparting excellent viewing angle characteristics, it is preferable that the optically-anisotropic layer included in the optical film of the present invention satisfies Expression (1) shown below.

$$0.75 < Re(450)/Re(550) < 1.00 \quad (1)$$

In Expression (1), Re (450) represents in-plane retardation of the optically-anisotropic layer at a wavelength of 450 nm, and Re (550) represents in-plane retardation of the optically-anisotropic layer at a wavelength of 550 nm.

The value of in-plane retardation refers to a value measured using Axo Scan (0PMF-1, manufactured by Axometrics, Inc.), the attached software, and the light of a measurement wavelength.

In the present invention, the thickness of the optically-anisotropic layer is not particularly limited, but is preferably 0.1 to 10 μm and more preferably 0.5 to 5 μm.

[Support]

As described above, the optical film of the present invention may have a support as a base material for forming the optically-anisotropic layer.

The support is preferably a transparent support and specifically more preferably a support having a light transmittance equal to or higher than 80%.

Examples of the support include glass plates or polymer films. Examples of materials of the polymer films include a cellulose-based polymer; an acrylic polymer having an acrylic acid ester polymer such as polymethyl methacrylate or a lactone ring-containing polymer; a thermoplastic norbornene-based polymer; a polycarbonate-based polymer; a polyester-based polymer such as polyethylene terephthalate or polyethylene naphthalate; a styrene-based polymer such as polystyrene or an acrylonitrile-styrene copolymer (AS resin); a polyolefin-based polymer such as polyethylene, polypropylene, or an ethylene-propylene copolymer; a vinyl chloride-based polymer; an amide-based polymer such as nylon or aromatic polyamide; an imide-based polymer; a sulfone-based polymer; a polyether sulfone-based polymer; a polyether ether ketone-based polymer; a polyphenylene sulfide-based polymer; a vinylidene chloride-based polymer; a vinyl alcohol-based polymer; a vinyl butyral-based polymer; an arylate-based polymer; a polyoxymethylene-based polymer; an epoxy-based polymer; and a polymer obtained by mixing these polymers together.

In addition, an aspect may be adopted in which the polarizer which will be described later also functions as the aforementioned support.

In the present invention, the thickness of the aforementioned support is not particularly limited, but is preferably 5 to 60 μm and more preferably 5 to 30 μm.

[Alignment Film]

In a case where the optical film of the present invention has any support described above, it is preferable that an alignment film is provided between the support and the optically-anisotropic layer. Herein, an aspect may be adopted in which the aforementioned support also functions as an alignment film.

Generally, an alignment film contains a polymer as a main component. The polymer material for the alignment film is described in a number of documents, and a number of commercial polymer materials are available.

As the polymer material used in the present invention, polyvinyl alcohol or polyimide and derivatives thereof are preferable. Particularly, modified or unmodified polyvinyl alcohol is preferable.

Regarding the alignment film usable in the present invention, it is possible to refer to the alignment film described in line 24 on page 43 to line 8 on page 49 in WO01/88574A; modified polyvinyl alcohol described in paragraphs "0071" to "0095" in JP3907735B; the liquid crystal alignment film formed using a liquid crystal alignment agent described in JP2012-155308A; and the like.

In the present invention, it is also preferable to use a photo-alignment film as the alignment film, because then the surface of the alignment film is not touched at the time of forming the alignment film and hence the deterioration of the surface conditions can be prevented.

The photo-alignment film is not particularly limited, and it is possible to use the polymer material such as a polyamide compound or a polyimide compound described in paragraphs "0024" to "0043" in WO2005/096041A; the liquid crystal alignment film formed using a liquid crystal alignment agent having a photo-alignable group described in JP2012-155308A; the material having a trade name of LPP-JP265CP manufactured by Rolic Technologies Ltd.; and the like.

In the present invention, the thickness of the aforementioned alignment film is not particularly limited. However, from the viewpoint of mitigating the surface asperity, which may be found in the support, and forming an optically-anisotropic layer having a uniform thickness, the thickness of the alignment film is preferably 0.01 to 10 µm, more preferably 0.01 to 1 µm, and even more preferably 0.01 to 0.5 µm.

[Hardcoat Layer]

In order to impart physical strength to the film, it is preferable that the optical film of the present invention has a hardcoat layer. Specifically, the hardcoat layer may be provided on a side, which is opposite to a side provided with the alignment film, of the support (see FIG. 1B) or on a side, which is opposite to a side provided with the alignment film, of the optically-anisotropic layer (see FIG. 1C).

As the hardcoat layer, those described in paragraphs "0190" to "0196" in JP2009-98658A can also be used.

[Other Optically-Anisotropic Layers]

The optical film of the present invention may have other optically-anisotropic layers, in addition to the layer obtained by polymerizing the polymerizable liquid crystal composition containing the polymerizable compound (I), the liquid crystal compound (II), and the polymerization initiator described above as well as other optional polymerizable compounds, an organic solvent, and the like (in this paragraph, this layer will be formally referred to as "optically-anisotropic layer of the present invention").

That is, the optical film of the present invention may have a laminated structure including the optically-anisotropic, layer of the present invention and other optically-anisotropic layers.

The aforementioned other optically-anisotropic layers are not particularly limited as long as they are optically-anisotropic layers containing a liquid crystal compound other than the aforementioned liquid crystal compound (II).

Generally, according to their shape, the liquid crystal compounds can be classified into rod-like types and discotic types, and each of these is further classified into low-molecular weight types and polymer types. Usually, a polymer refers to a compound having a degree of polymerization of 100 or higher (Polymer physics-Phase Transition Dynamics, Masao DOI, p. 2, Iwanami Shoten, Publishers, 1992). In the present invention, any of the liquid crystal compounds can be used. However, it is preferable to use rod-like liquid crystal compounds or discotic liquid crystalline compounds (disk-like liquid crystal compounds). Moreover, two or more kinds of rod-like liquid crystal compounds, two or more kinds of discotic liquid crystal compounds, or a mixture of a rod-like liquid crystal compound and a discotic liquid crystal compound may be used. For the fixation of the aforementioned liquid crystal compounds, the optically-anisotropic layer is more preferably formed using the rod-like liquid crystal compound or the discotic liquid crystal compound having a polymerizable group. Even more preferably, the liquid crystal compound has two or more polymerizable groups in one molecule. In a case where the liquid crystal compound is in the form of a mixture of two or more kinds of compounds, it is preferable that at least one kind of liquid crystal compound has two or more polymerizable groups in one molecule.

As the rod-like liquid crystal compound, for example, those described in claim 1 in JP1999-513019A (JP-H11-513019A) or described in paragraphs "0026" to "0098" in JP2005-289980A can be preferably used. As the discotic liquid crystal compound, for example, those described in paragraphs "0020" to "0067" in JP2007-108732 A or paragraphs "0013" to "0108" in JP2010-24403A can be preferably used. However, the present invention is not limited to these.

[Ultraviolet Absorber]

Considering the influence of external light (particularly ultraviolet rays), the optical film of the present invention preferably contains an ultraviolet (UV) absorber and more preferably contains an ultraviolet absorber in the support.

As the ultraviolet absorber, any of known compounds that can exhibit ultraviolet absorptivity can be used. Among such ultraviolet absorbers, benzotriazole-based or hydroxyphenyl triazine-based ultraviolet absorbers are preferable, since these exhibit a high degree of ultraviolet absorptivity and make it possible to obtain an ultraviolet absorbing ability (ultraviolet cut-off ability) used in electronic image display devices. Furthermore, in order to make the optical film absorb a wider range of ultraviolet rays, two or more kinds of ultraviolet absorbers having different maximum absorption wavelengths can be used in combination.

[Polarizing Plate]

The polarizing plate of the present invention includes the aforementioned optical film of the present invention and a polarizer.

[Polarizer]

The polarizer included in the polarizing plate of the present invention is not particularly limited as long as it is a member that functions to convert light into specific linearly polarized light, and an absorptive polarizer and a reflective polarizer known in the related art can be used.

As the absorptive polarizer, an iodine-based polarizer, a dye-based polarizer in which a dichroic dye is used, a polyene-based polarizer, and the like are used. The iodine-based polarizer and the dye-based polarizer include a coating-type polarizer and a stretching-type polarizer, and all of these can be used. However, it is preferable to use a polarizer which is prepared by causing iodine or a dichroic dye to be adsorbed onto polyvinyl alcohol and stretching the resultant.

As a method for obtaining a polarizer by stretching or staining a laminated film obtained by forming a polyvinyl alcohol layer on a base material, those described in JP5048120B, JP5143918B, JP4691205B, JP4751481B, and JP4751486B can be exemplified. The known techniques relating to the polarizers obtained by these methods can also be preferably used.

As the reflective polarizer, a polarizer obtained by laminating thin films having different birefringence properties, a wire grid-type polarizer, a polarizer obtained by combining cholesteric liquid crystals having a selective reflection range and a ¼ wavelength plate, and the like are used.

Among these, a polarizer containing a polyvinyl alcohol-based resin (a polymer having —$CH_2$—CHOH— as a repeating unit, particularly, at least one polymer selected from the group consisting of polyvinyl alcohol and an ethylene-vinyl alcohol copolymer) is preferable, because this polarizer exhibits stronger adhesiveness with respect to a resin layer which will be described later.

In the present invention, the thickness of the polarizer is not particularly limited, but is preferably 3 µm to 60 µm, more preferably 5 µm to 30 µm, and even more preferably 5 µm to 15 µm.

[Pressure Sensitive Adhesive Layer]

In the polarizing plate of the present invention, a pressure sensitive adhesive layer may be disposed between the optically-anisotropic layer in the optical film of the present invention and the polarizer.

The pressure sensitive adhesive layer used for laminating the optically-anisotropic layer and the polarizer is, for example, a substance in which a ratio between a storage elastic modulus G' and a loss elastic modulus G" (tan δ=G"/G') measured using a dynamic viscoelasticity measuring device is 0.001 to 1.5, and includes a so-called pressure sensitive adhesive, an easily creeping substance, and the like. Examples of the pressure sensitive adhesive usable in the present invention include a polyvinyl alcohol-based pressure sensitive adhesive, but the present invention is not limited to this.

[Image Display Device]

The image display device of the present invention is an image display device having the optical film of the present invention or the polarizing plate of the present invention.

The display element used in the image display device of the present invention is not particularly limited, and examples thereof include a liquid crystal cell, an organic electroluminescence (hereinafter, abbreviated to "EL") display panel, a plasma display panel, and the like.

Among these, a liquid crystal cell and an organic EL display panel are preferable, and a liquid crystal cell is more preferable. That is, the image display device of the present invention is preferably a liquid crystal display device in which a liquid crystal cell is used as a display element or an organic EL display device in which an organic EL display panel is used as a display element, and more preferably a liquid crystal display device.

[Liquid Crystal Display Device]

The liquid crystal display device as an example of the image display device of the present invention is a liquid crystal display device having the polarizing plate of the present invention described above and a liquid crystal cell.

In the present invention, among the polarizing plates provided on both sides of a liquid crystal cell, the polarizing plate of the present invention is preferably used as a polarizing plate on the front side and more preferably used as a polarizing plate on the front and rear sides.

Hereinafter, the liquid crystal cell constituting the liquid crystal display device will be specifically described.

<Liquid Crystal Cell>

The liquid crystal cell used in the liquid crystal display device is preferably a Vertical. Alignment (VA)-mode liquid crystal cell, an Optically Compensated Bend (OCPs)-mode liquid crystal cell, an In-Plane-Switching (IPS)-mode liquid crystal cell, or a Twisted Nematic (TN)-mode liquid crystal cell, but is not limited to these.

In the TN-mode liquid crystal cell, rod-like liquid crystal molecules are substantially horizontally aligned when voltage is not applied thereto, and aligned in a state where the molecules are twisted at an angle of 60° to 120°. The TN-mode liquid crystal cell is most frequently used in a color TFT liquid crystal display device and described in a number of documents.

In the VA-mode liquid crystal cell, rod-like liquid crystal molecules are substantially vertically aligned when voltage is not applied thereto. The VA-mode liquid crystal cell include (1) VA-mode liquid crystal cell (described in JP1990-176625A (JP-H02-176625A) in a narrow sense, in which rod-like liquid crystal molecules are substantially vertically aligned when voltage is not applied thereto and substantially horizontally aligned when voltage is applied thereto, (2) liquid crystal cell (MVA mode) (described in SID 97, Digest of tech. Papers (proceeding) 28 (1997), 845) obtained by making the VA mode into a multi-domain mode so as to widen the viewing angle, (3) liquid crystal cell (n-ASM mode) (described in proceeding of Japanese Liquid Crystal Conference, 58~59 (1998)) adopting a mode in which rod-like liquid crystal molecules are substantially vertically aligned when voltage is not applied thereto and aligned in multi-domain mode in a twisted manner when voltage is applied thereto, and (4) liquid crystal cell of a SURVIVAL mode (presented in LCD International 98'). Furthermore, the liquid crystal cell may be any of a Patterned Vertical Alignment (PVA) type, an optical alignment type, and a Polymer-Sustained Alignment (PSA) type. Details of these modes are specifically described in JP2006-215326A and JP2008-538819A.

In the IPS-mode liquid crystal cell, rod-like liquid crystal molecules are substantially aligned in parallel to a substrate, and in a case where an electric field parallel to the substrate surface is applied thereto, the liquid crystal molecules respond in a planar manner. In the IPS mode, black display is performed in a state where the electric field is not being applied to the liquid crystal cell, and absorption axes of a pair of polarizing plates, an upper polarizing plate and a lower polarizing plate, are orthogonal to each other. JP1998-54982A (JP-H10-54982A), JP1999-202323A (JP-H11-202323A), JP1997-292522A (JP-1409-292522A), JP1999-133408A (JP-H11-133408A), JP1999-305217A (JP-H11-305217A), JP1998-307291A (JP-H10-307291A), and the like disclose a method for reducing light leakage at the time of black display in an oblique direction by using an optical compensation sheet so as to improve a viewing angle.

[Organic EL Display Device]

As the organic EL display device, which is an example of the image display device of the present invention, an aspect can be suitably exemplified in which the polarizing plate of the present invention, a plate having a λ/4 function. (hereinafter, referred to as "λ/4 plate" as well), and an organic EL display panel are laminated in this order from the viewer's side.

"Plate having λ/4 function" refers to a plate that functions to convert linearly polarized light having a specific wavelength into circularly polarized light (or functions to convert circularly polarized light into linearly polarized light). For example, the aspect in which the λ/4 plate has a single layer structure specifically includes a stretched polymer film, a phase difference film in which an optically-anisotropic layer having the λ/4 function is provided on a support, and the like. Furthermore, the aspect in which the λ/4 plate has a multilayer structure specifically include, for example, a broadband λ/4 plate obtained by laminating a λ/4 plate and a λ/2, plate.

The organic EL display panel is a display panel constituted with an organic EL element including of electrodes (an anode and a cathode) and an organic light-emitting layer (organic electroluminescence layer) interposed between the electrodes. The constitution of the organic EL display panel is not particularly limited, and known constitutions can be adopted.

[Polymerizable Compound]

The polymerizable compound of the present invention is a polymerizable compound represented by Formula (I) described above, and has the same definition as the polymerizable compound (I) described above regarding the optically-anisotropic layer included in the optical film of the present invention described above.

[Method for Manufacturing Monoaryl Ester]

The method for manufacturing a 1,4-cyclohexanedicarboxylic acid monoaryl ester (hereinafter, simply described as "monoaryl ester" as well) of the present invention is a manufacturing method including a reaction step of reacting 1,4-cyclohexanedicarboxylic acid dichloride with a phenol-based compound in the presence of a base whose conjugate acid has an acid dissociation constant pKa of equal to or greater than 7 and equal to or smaller than 30, and a hydrolysis step of hydrolyzing a reaction product obtained by the reaction step so as to obtain a 1,4-cyclohexanedicarboxylic acid monoaryl ester represented by Formula (Ia) or (II) which will be described later, in which in the reaction step, a ratio of a molar equivalent of the 1,4-cyclohexanedicarboxylic acid dichloride to a molar equivalent of the phenol-based compound is equal to or higher than 1.5 and equal to or lower than 10.

"1,4-cyclohexanedicarboxylic acid monoaryl ester" obtained by the method for manufacturing a monoaryl ester of the present invention is a compound useful as an intermediate product used for synthesizing the polymerizable compound represented by Formula (I) described above or the liquid crystal compound represented by Formula (II) described above.

[Reaction Step]

The reaction step included in the method for manufacturing a monoaryl ester of the present invention is a step of reacting 1,4-cyclohexanedicarboxylic acid dichloride with a phenol-based compound.

In the present invention, the reaction step is performed by setting a ratio of a molar equivalent of the 1,4-cyclohexanedicarboxylic acid dichloride to a molar equivalent of the phenol-based compound to be equal to or higher than 1.5 and equal to or lower than 10, in the presence of a base whose conjugate acid has an acid dissociation constant pKa of equal to or greater than 7 and equal to or smaller than 30.

<Starting Material>

As the 1,4-cyclohexanedicarboxylic acid dichloride used in the reaction step, from the viewpoint of synthesizing a monoaryl ester represented by Formula (Ia) or (IIa) which will be described later, trans-1,4-cyclohexanedicarboxylic acid dichloride is used.

As the phenol-based compound used in the reaction step, from the viewpoint of synthesizing a monoaryl ester represented by Formula (Ia) or (IIa) which will be described later, a compound represented by Formula (Ib) or (IIb) shown below is used.

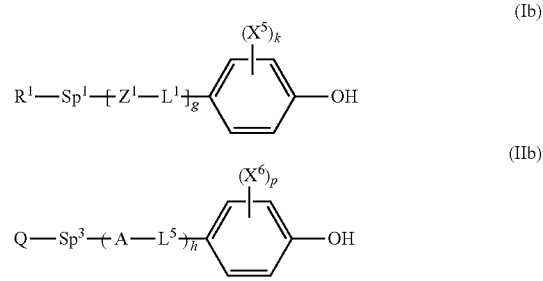

In Formula (Ib), g represents an integer of 0 or 1.

In the present invention, g is preferably 0, because then the solubility becomes excellent, and the manufacturing suitability is improved.

In Formula (Ib) shown above, $X^5$ represents a substituent, and k represents an integer of 0 to 4. In a case where k is an integer of 2 to 4, a plurality of $X^5$'s may be the same as or different from each other.

Examples of the substituent include an alkyl group, an alkoxy group, a halogen atom, and the like that are substituents of $Z^1$ in Formula (I) described above.

In Formula (Ib) shown above, $Z^1$ represents a trans-1,4-cyclohexylene group which may have a substituent, an arylene group which may have a substituent, or a heteroarylene group which may have a substituent.

In the present invention, the arylene group and the heteroarylene group as well as the substituents that the trans-1,4-cyclohexylene group, the arylene group, or the heteroarylene group may have are the same as those explained above regarding $Z^1$ in Formula (I) described above.

For expressing liquid crystallinity, $Z^1$ in Formula (Ib) shown above is preferably an arylene group which may have a substituent, and more preferably a 1,4-phenylene group which may have a substituent.

In Formula (Ib) shown above, $L^1$ represents any linking group selected from the group consisting of a single bond, —O—, —CH$_2$O—, —OCH$_2$—, —(CH$_2$)$_2$OC(=O)—, —C(=O)O(CH$_2$)$_2$—, —NH—, —N(CH$_3$)—, —S—, —C(=O)O—, —OC(=O)—, —OC(=O)O—, —C(=O)N(R$^3$)—, —N(R$^3$)C(=O)—, —C(=O)S—, —SC(=O)—, —CH$_2$C(=O)O—, —OC(=O)CH$_2$—, —CH=CH—C (=O)O—, —OC(=O)—CH=CH—, —CH=N—, —N=CH—, and —N=N—, and $R^3$ represents a hydrogen atom, an alkyl group having 1 to 20 carbon atoms, or an aryl group having 6 to 20 carbon atoms.

In the present invention, the alkyl group and the aryl group represented by $R^3$ are the same as those explained above regarding $L^1$ in Formula (I) described above.

$L^1$ in Formula (Ib) shown above is preferably —C(=O)O— or —OC(=O)—, because then the solubility becomes excellent, and the manufacturing suitability is improved.

In Formula (Ib) shown above, $Sp^1$ represents any linking group selected from the group consisting of a single bond, a linear or branched alkylene group having 1 to 20 carbon atoms, and a group obtained in a case where one or more —CH$_2$— groups constituting a linear or branched alkylene group having 1 to 20 carbon atoms are substituted with —O—, —S—, —NH—, —N(CH$_3$)—, —C(=O)—, —OC(=O)—, or —C(=O)O—.

In the present invention, the linear or branched alkylene group (including an unsubstituted alkylene group) having 1 to 20 carbon atoms represented by $Sp^1$ are the same as that explained above regarding $Sp^1$ in Formula (I) described above.

For expressing liquid crystallinity, $Sp^1$ in Formula (Ib) shown above preferably represent a group (linking group) obtained in a case where one or more groups constituting a linear or branched alkylene group having 1 to 20 carbon atoms are substituted with —O—, —S—, —NH—, —N(CH$_3$)—, —C(=O)—, —OC(=O)—, or —C(=O)O—, more preferably represent a group (linking group) obtained in a case where one or more —CH$_2$— groups constituting a linear or branched alkylene group having 5 to 15 carbon atoms are substituted with —O—, —OC(=O)—, or —C(=O)O—, and even more preferably represent a group (linking group) obtained in a case where one or two —CH$_2$— groups constituting a linear or branched alkylene group having 5 to 15 carbon atoms are substituted with —OC(=O)— or —C(=O)O— and one —CH$_2$— group constituting a linear or branched alkylene group having 5 to 15 carbon atoms is substituted with —O—.

In Formula (Ib) shown above, $R^1$ represents any polymerizable group selected from the group consisting of groups represented by Formulae (R-1) to (R-5) shown below. In Formulae (R-1) to (R-5) shown below, * represents a position bonded to $Sp^1$.

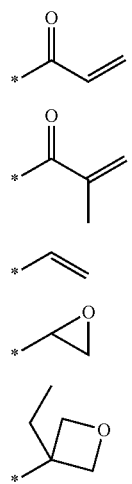

(R-1)
(R-2)
(R-3)
(R-4)
(R-5)

In Formula (IIb) shown above, h represents an integer of 0 or 1.

In the present invention, h is preferably 0, because then the solubility becomes excellent, and the manufacturing suitability is improved.

In Formula (IIb) shown above. $X^6$ represents a substituent, and p represents an integer of 0 to 4. In a case where p is an integer of 2 to 4, a plurality of $X^6$'s may be the same as or different from each other.

Examples of the substituent include an alkyl group, an alkoxy group, a halogen atom, and the like that are substituents of $Z^1$ in Formula (I) described above.

In Formula (IIb) shown above, $L^5$ represents a single bond, —COO—, or —OCO—, and A represents an aromatic ring having 6 or more carbon atoms or a cycloalkylene ring having 6 or more carbon atoms.

In the present invention, the aromatic ring having 6 or more carbon atoms and the cycloalkylene ring having 6 or more carbon atoms represented by A are the same as those represented by A in Formula (If) described above.

In Formula (IIb), $Sp^3$ represents a single bond, a linear or branched alkylene group having 1 to 12 carbon atoms, or a divalent linking group obtained in a case where one or more —CH$_2$— groups constituting a linear or branched alkylene group having 1 to 12 carbon atoms are substituted with —O—, —S—, —NH—, —N(Q)-, or —CO—, and Q represents a polymerizable group.

In the present invention, the linear or branched alkylene group having 1 to 12 carbon atoms represented by $Sp^3$ is the same as that represented by $Sp^3$ in Formula (II) described above.

<Reaction Condition>

As described above, the reaction step is performed by setting a ratio of a molar equivalent of the 1,4-cyclohexanedicarboxylic acid dichloride to a molar equivalent of the phenol-based compound to be equal to or higher than 1.5 and equal to or lower than 10, in the presence of a base whose conjugate acid has an acid dissociation constant pKa of equal to or greater than 7 and equal to or smaller than 30.

The acid dissociation constant pKa means pKa in an aqueous solution and is described in, for example, Chemistry Guide (II) (4$^{th}$ revised edition, 1993, edited by The Chemical Society of Japan, Maruzen Publishing Co., Ltd). The higher the value of pKa, the stronger the acid. Specifically, the acid dissociation constant pKa in an aqueous solution can be obtained by measuring an acid dissociation constant at 25° C. by using an infinitely diluted aqueous solution. Furthermore, by using a software package 1 shown below, a value based on the Hammett substituent constant and the database of values in known documents can be determined by calculation. All of the values of pKa described in the present specification are values determined by calculation by using the software package.

<Software Package>

Advanced Chemistry Development (ACD/Labs) Software V8.14 for Solaris (1994-2007 ACD/Labs)

in the method for manufacturing a monoaryl ester of the present invention, the aforementioned reaction step is performed. Accordingly, a monoaryl ester compound is generated first, and the generation of a diaryl ester compound is inhibited. Therefore, through the hydrolysis step which will be described later, a desired 1,4-cyclohexanedicarboxylic acid monoaryl ester can be efficiently obtained.

In the present invention, during the aforementioned reaction step, the ratio of a molar equivalent of the 1,4-cyclohexanedicarboxylic acid dichloride to a molar equivalent of the phenol-based compound is preferably 1.6 to 3.0 and more preferably 1.7 to 2.5.

The aforementioned reaction step is preferably performed in the presence of a base whose conjugate acid has an acid dissociation constant pKa of equal to or greater than 8 and equal to or smaller than 20, and more preferably performed in the presence of a base whose conjugate acid has an acid dissociation constant pKa of equal to or greater than 9 and equal to or smaller than 13.

Specific examples of such a base include triethylamine, N-ethyldiisopropylamine, N-methylmorpholine, tributylamine, N-methylpiperidine, N-butyldimethylamine, and the like.

[Hydrolysis Step]

The hydrolysis step included in the method for manufacturing a monoaryl ester of the present invention is a step of hydrolyzing a reaction product obtained by the reaction step so as to obtain a 1,4-cyclohexanedicarboxylic acid monoaryl ester represented by Formula (Ia) or (II) shown below.

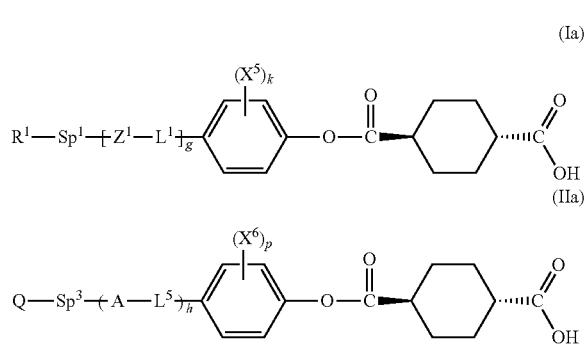

All of $R^1$, $Sp^1$, $Z^1$, $L^1$, g, $X^5$, and k in Formula shown above are the same as those in Formula (Ib) described above.

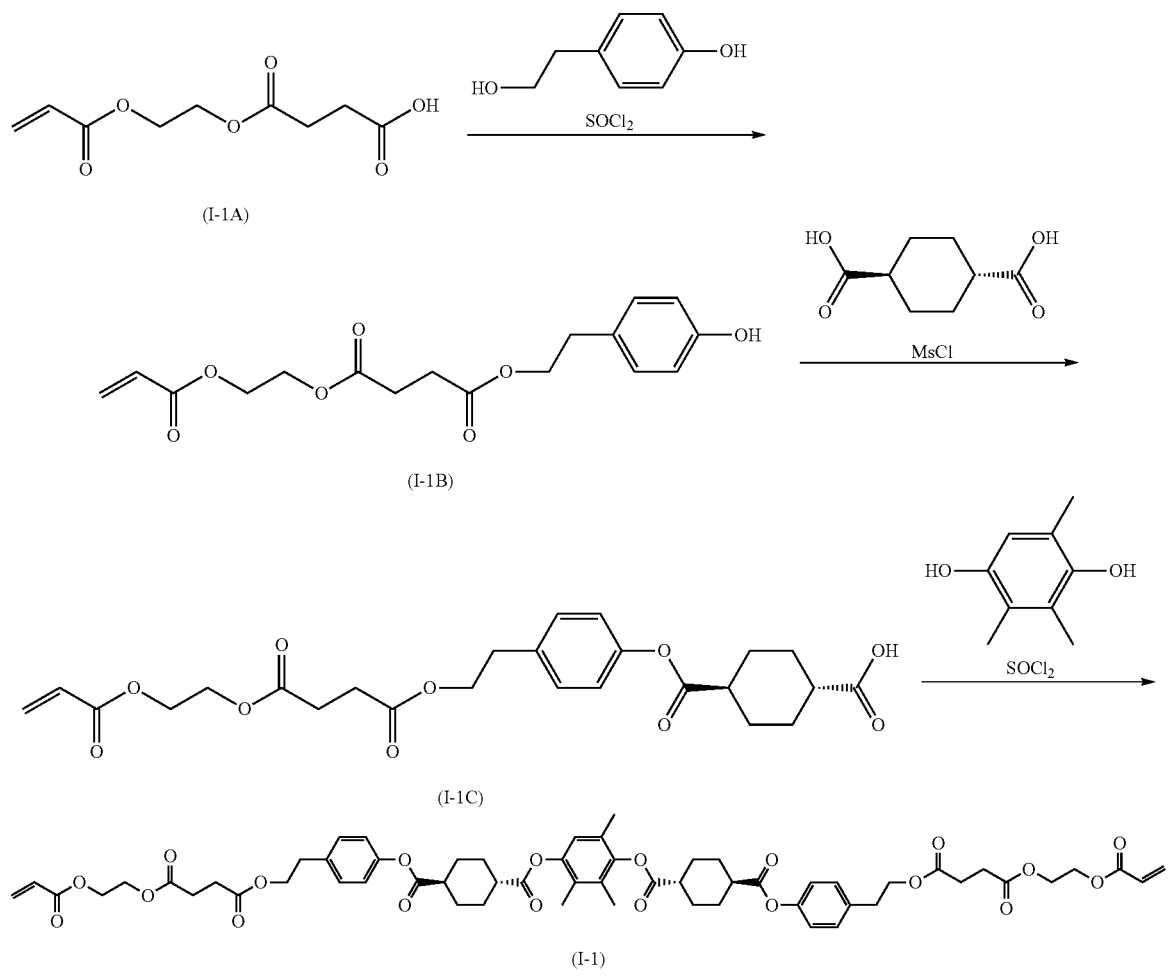

Furthermore, all of Q, $Sp^3$, A, $L^5$, h, $X^6$, and p in Formula (IIa) shown above are the same as those in Formula (IIb) described above.

EXAMPLES

Hereinafter, the present invention will be more specifically described based on examples. The materials, the amount of the materials used, the proportion of the materials, the treatment content, the treatment sequence, and the like shown in the following examples can be appropriately modified as long as the gist of the present invention is maintained. Accordingly, the scope of the present invention should not be limitedly interpreted by the examples described below.

[Synthesis of Polymerizable Compound (I-1)]

According to the following scheme, a compound (I-1) was synthesized. The compound (I-1) is the same compound as the compound represented by Formula (I-1) described above.

<Synthesis of Compound (I-1B)>

182 g (839 mmol) of mono(2-acryloyloxyethyl) succinate (I-1A), 600 mL of ethyl acetate, 150 mL of N,N-dimethylacetamide, and 680 mg of 2,6-di-t-butyl-4-methylphenol were mixed together and cooled such that the internal temperature decreased to 5° C. 642 mL (879 mmol) of thionyl chloride was added dropwise to the mixture such that the internal temperature did not increase to 10° C. or a higher temperature. The mixture was stirred for 1 hour at 5° C., and then 220 mL of a N,N-dimethylacetamide solution containing 111 g (800 mmol) of 2-(4-hydroxyphenyl)ethanol was added thereto. Thereafter, the mixture was stirred for 12 hours at room temperature, 400 mL of water was then added thereto, and liquid separation was performed. The collected organic layer was washed with 1 N aqueous hydrochloric acid, saturated aqueous sodium bicarbonate, and saturated saline and then dried over anhydrous sodium sulfate. The sodium sulfate was separated by filtration, and the solvent was removed using a rotary evaporator, thereby obtaining 255 g (758 nymol) of a compound (I-1B) as transparent oil (yield: 95%).

The nuclear magnetic resonance ($^1$H-NMR) of the obtained compound (I-1B) is shown below.

$^1$H-NMR. (solvent: CDCl$_3$) δ (ppm): 2.63 (s, 4H), 2.85 (t, 2H), 4.25 (t, 2H), 4.28-4.40 (m, 4H), 5.75 (br s, 1H), 5.86 (dd, 1H), 6.14 (dd, 1H), 6.45 (dd, 1H), 6.78-6.80 (m, 2H), 7.02-7.10 (m, 2H)

<Synthesis of Compound (I-1C)>

305 g (1.77 mmol) of 1,4-trans-cyclohexanedicarboxylic acid, 74.2 g (648 mmol) of methanesulfonic acid chloride, 576 mL of tetrahydrofuran, and 576 mL of N,N-dimethylacetamide were mixed together at room temperature. 72 g (708 mmol) of triethylamine was added dropwise to the obtained mixture such that the internal temperature did not increase to 30° C. or a higher temperature, and then the mixture was stirred for 2 hours at room temperature. 198 g (589 mmol) of the compound (I-1B) and 50 mL of a tetrahydrofuran solution containing 12 mg of 2,6-di-t-butyl-4-methylphenol were added to the reaction solution. Thereafter, 1.4 g (11 mmol) of N,N-dimethylaminopyridine was added thereto, and then 72 g (708 mmol) of triethylamine was added dropwise thereto such that the internal temperature did not increase to 30° C. or a higher temperature. Subsequently, the reaction solution was stirred for 12 hours at room temperature, and 57 mL of water was added thereto so as to stop the reaction. The obtained reaction solution was added dropwise to 5.7 L of 1.8 wt % aqueous sodium bicarbonate, and the precipitated solid content was collected by filtration. The obtained solid content was mixed with 1.6 L of methanol, 1.9 L of water was then added thereto, and the solid content precipitated again was collected by filtration. The obtained solid content was dried and then dissolved in 1.6 L of ethyl acetate. 1.9 L of hexane was slowly added to the obtained solution such that recrystallization occurred, and the precipitated crystal was collected by filtration, thereby obtaining 202 g of a white solid (I-1C) (yield: 70%). $^1$H-NMR of the obtained white solid (I-1C) is shown below.

At this time, although a diester compound of cyclohexanedicarboxylic acid remained as an impurity, the compound (I-1C) in the formed of a mixture was used for the next step as it was because the impurity was removed in the next step.

$^1$H-NMR (solvent: CDCl$_3$) δ (ppm): 1.40-1.73 (m, 4H), 2.08-2.31 (m, 4H), 2.31-2.45 (m, 1H), 2.45-2.70 (m, 1H), 2.63 (m, 4H), 2.93 (t, 2H), 4.29 (t, 2H), 4.29-4.40 (m, 4H), 5.86 (dd, 1H), 6.15 (dd, 1H), 6.44 (dd, 1H), 6.95-7.05 (m, 2H), 7.17-7.25 (m, 2H)

<Synthesis of Compound (I-1)>

67.44 g of the compound (I-1C) (purity: 74.15%), 280 ml of ethyl acetate, 75 ml of N,N-dimethylacetamide, and 300 mg of 2,6-di-t-butyl-4-methylphenol were mixed together and cooled such that the internal temperature decreased to 0° C. 12.04 g of thionyl chloride was added dropwise to the mixture at an internal temperature of 0° C. to 5° C. The mixture was stirred for 60 minutes at 5° C., and then 6.38 g of a compound trimethyl hydroquinone and 10 ml of an ethyl acetate solution were added dropwise thereto at an internal temperature of 0° C. to 8° C. Thereafter, 1.54 g of N,N-dimethylaminopyridine was added thereto, and 26.14 g of N,N-diisopropylethylamine was added dropwise thereto at an internal temperature of 0° C. to 10° C. The mixture was stirred for 4 hours at an internal temperature of 15° C. to 20° C., and then 200 ml of acetonitrile, 200 ml of water, and 21 ml of concentrated hydrochloric acid were added thereto for washing. The organic layer was washed with 200 ml of saturated saline, and liquid separation was performed. Subsequently, the organic layer was washed with 100 ml of saturated saline and 10 ml of 7.5 wt % aqueous sodium bicarbonate, and liquid separation was performed. The organic layer was dried over anhydrous magnesium sulfate, 19 g of silica gel (WAKOGEL, C-200) was added thereto, and the mixture was stirred for 60 minutes. The magnesium sulfate and the silica gel were separated by filtration, the solvent was distilled away under reduced pressure, and then recrystallization was performed using methanol, thereby obtaining 37.8 g of a compound (I-1) (yield: 80%).

$^1$H-NMR of the obtained compound (I-1) is shown below.

$^1$H-NMR (solvent: CDCl$_3$) σ (ppm): 1.25-1.32 (m, 8H), 1.62-1.76 (m, 8H), 2.05 (s, 3H), 2.06 (s, 3H), 2.10 (s, 3H), 2.21-2.37 (m, 8H), 2.54-2.68 (m, 12H), 2.94 (t, 4H), 4.10-4.24 (m, 4sH), 4.29 (t, 4H), 5.15-5.25 (m, 2H), 5.82-5.88 (m, 2H), 6.07-6.18 (m, 2H), 6.38-6.46 (m, 2H), 6.73 (s, 1H), 7.01 (d, 4H), 7.23 (d, 4H)

<Synthesis of Compound (I-1C)>

According to the following scheme, the aforementioned compound (I-1C) used for synthesizing the aforementioned compound (I-1) was synthesized. As a result, it was found that the generation of a diester compound of cyclohexanedicarboxylic acid, which is an impurity, was further inhibited compared to the scheme described above.

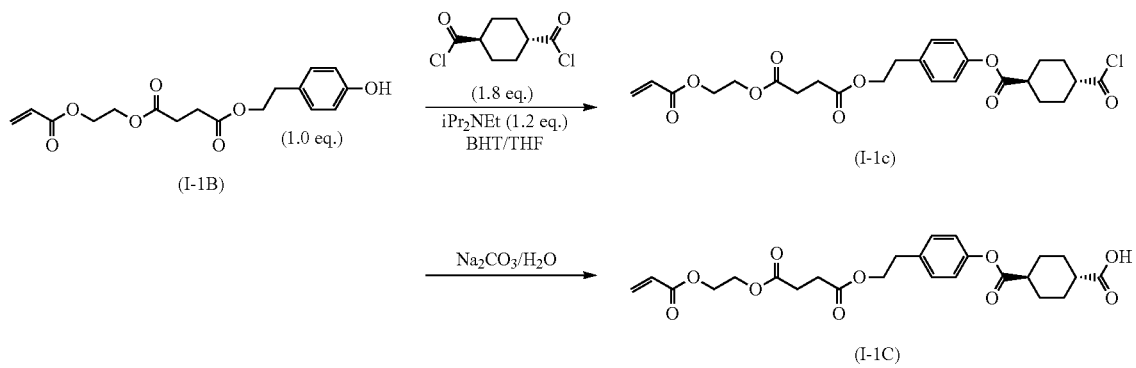

Specifically, 8.41 g (25.0 mmol) of the compound (I-1B), 60 mg of 2,6-di-t-butyl-4-methylphenol, 9.41 g (45.0 mmol) of trans-1,4-cyclohexanedicarboxylic acid dichloride, and 40 ml of tetrahydrofuran (THF) were mixed together, and then 3.88 g (30.0 mmol) of N-ethyldiisopropylamine (iPr-NEt) [pKa value: 11] was added dropwise thereto for 30 minutes at a temperature of 5° C. to 10° C.

Thereafter, the mixture was stirred for 1 hour at a temperature of 5° C. to 10° C., 20 ml of aqueous sodium compound I-1C was determined. As a result, the purity of the compound was 81.6%, and the yield thereof was 72.5%. Furthermore, through HPLC, it was revealed that a ratio of compound I-1C/diester compound is 91/9.

[Synthesis of Polymerizable Compound (I-2)]

According to the following scheme, a compound (I-2) was synthesized. The compound (I-2) is the same compound as the compound represented by Formula (I-2) described above.

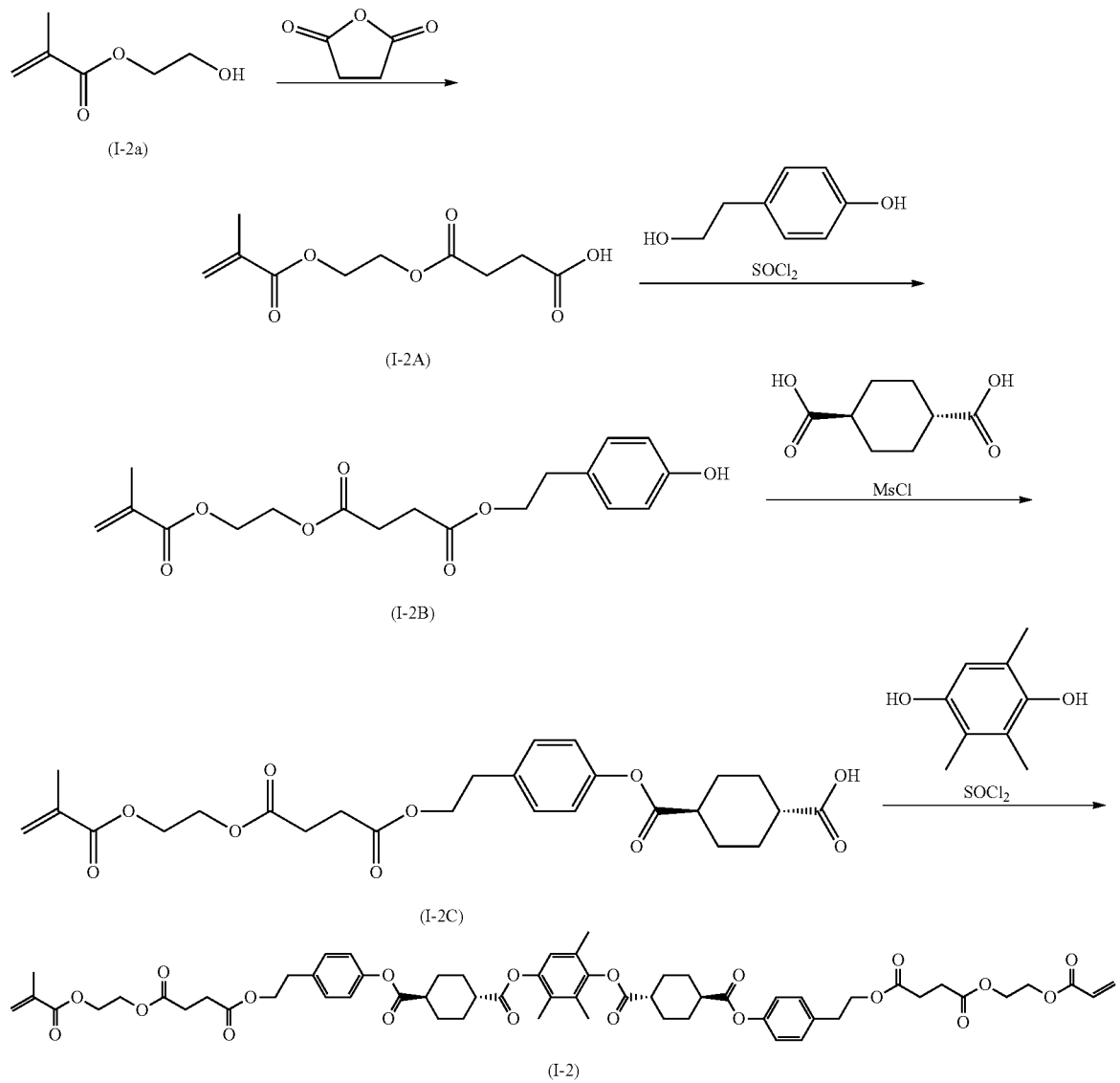

carbonate was then added dropwise thereto for 30 minutes, and the mixture was stirred for 30 minutes.

Subsequently, liquid separation was performed, 18 ml of ethyl acetate was then added to the organic layer, and the organic layer was washed twice with aqueous sodium carbonate and once with aqueous dilute hydrochloric acid. The solvent was distilled away under reduced pressure, and then recrystallization was performed using an ethanol/heptane mixed solvent, thereby obtaining 10.89 g of the compound (I-1C) (rough yield: 88.8%). Through high performance liquid chromatography (HPLC), the quantity of the purified <Synthesis of Compound (I-2A)>

40 g (307 mmol) of 2-hydroxyethyl methacrylate (I-2a), 300 mL of dichloromethane, 3.8 g (30.7 mmol) of INN-dimethylaminopyridine, 33.8 g (338 mmol) of succinic anhydride, and 200 mg of 2,6-di-t-butyl-4-methylphenol were mixed together and heated such that the internal temperature increased to 40° C. The mixture was stirred for 12 hours, and then cooled to room temperature. Then, 300 mL of water was added thereto, the mixture was stirred for 1 hour, and liquid separation was performed. The collected organic layer was washed with 1 N aqueous hydrochloric acid and saturated saline and then dried over anhydrous sodium sulfate. The sodium sulfate was separated by filtration, and the solvent was removed using a rotary evaporator, thereby obtaining 64 g (278 mmol) of a compound (I-2A) as a transparent oil (yield: 91%).

<Synthesis of Compound (I-2B)>

30 g (130 mmol) of the compound (I-2A), 50 mL of ethyl acetate, 15 mL of N,N-dimethylacetamide, and 100 mg of 2,6-di-t-butyl-4-methylphenol were mixed together and cooled such that the internal temperature decreased to 5° C. 10.0 mL (137 mmol) of thionyl chloride was added dropwise to the mixture such that the internal temperature did not increase to 10° C. or a higher temperature. The mixture was stirred for 1 hour at 5° C., and 100 mL of a N,N-dimethylacetamide solution containing 18.0 g (130 mmol) of 2-(4-hydroxyphenyl)ethanol was added thereto. Thereafter, the mixture was stirred for 12 hours at room temperature, 100 mL of water was then added thereto, and liquid separation was performed. The collected organic layer was washed with 1 N aqueous hydrochloric acid, aqueous saturated sodium bicarbonate, and saturated saline and then dried over anhydrous sodium sulfate. The sodium sulfate was separated by filtration, and the solvent was removed using a rotary evaporator, thereby obtaining 44.1 g (126 mmol) of a compound (I-2B) as transparent oil (yield: 97%).

<Synthesis of Compound (I-2C)>

14.7 g (85.6 mol) of 1,4-trans-cyclohexanedicarboxylic acid, 3.60 g (31.4 mmol) of methanesulfonic acid chloride, 28 mL of tetrahydrofuran, and 28 mL of N,N-dimethylacetamide were mixed together at room temperature. 3.2 g (31.6 mmol) of triethylamine was added dropwise to the obtained mixture such that the internal temperature did not increase to 30° C. or a higher temperature, and then the mixture was stirred for 2 hours at room temperature. 10 g (28.5 mmol) of the compound (I-2B) and 10 mL of a tetrahydrofuran solution containing 50 mg of 2,6-di-t-butyl-4-methylphenol were added to the reaction solution. Thereafter, 171 mg (1.4 mmol) of N,N-dimethylaminopyridine was added thereto, and then 3.2 g (31.6 mmol) of triethylamine was added dropwise thereto such that the internal temperature did not increase to 30° C. or a higher temperature. Subsequently, the reaction solution was stirred for 12 hours at room temperature, and then 7 mL of water was added thereto so as to stop the reaction. The obtained reaction solution was added dropwise to 275 mL of 1.8 wt % aqueous sodium bicarbonate, and the precipitated solid content was collected by filtration. The obtained solid content was mixed with 80 mL of methanol, 92 mL of water was then added thereto, and the solid content precipitated again was collected by filtration. The obtained solid content was dried and then dissolved in 80 mL of ethyl acetate. 92 mL of hexane was slowly added to the obtained solution such that recrystallization occurred, and the precipitated crystal was collected by filtration, thereby obtaining 9.8 g (19.4 mmol) g of a white solid (I-2C) (yield: 68%). At this time, although a diester compound of cyclohexanedicarboxylic acid remained as an impurity, the compound (I-2C) in the formed of a mixture was used for the next step as it was because the impurity was removed in the next step.

<Synthesis of Compound (I-2)>

A compound (I-2) was synthesized (yield: 80%) by the same method as that used for synthesizing the compound (I-1), except that in the synthesis method of the compound (I-1), the compound (I-1C) was changed to the compound (I-2C).

¹H-NMR of the obtained compound (I-2) is shown below.

¹H-NMR (solvent: CDCl₃) σ (ppm): 1.25-1.32 (m, 8H), 1.62-1.76 (m, 8H), 1.95 (s, 6H), 2.05 (s, 3H), 2.06 (s, 3H), 2.10 (s, 3H), 2.21-2.37 (m, 8H), 2.54-2.68 (m, 12H), 2.94 (t, 4H), 4.10-4.24 (m, 4H), 4.29 (t, 4H), 5.15-5.25 (m, 2H), 5.59 (s, 2H), 6.12 (s, 2H), 6.73 (s, 1H), 7.01 (d, 4H), 7.23 (d, 4H)

[Synthesis of Polymerizable Compound (I-3)]

According to the following scheme, a compound (I-3) was synthesized. The compound (I-3) is the same compound as the compound represented by Formula (I-3) described above.

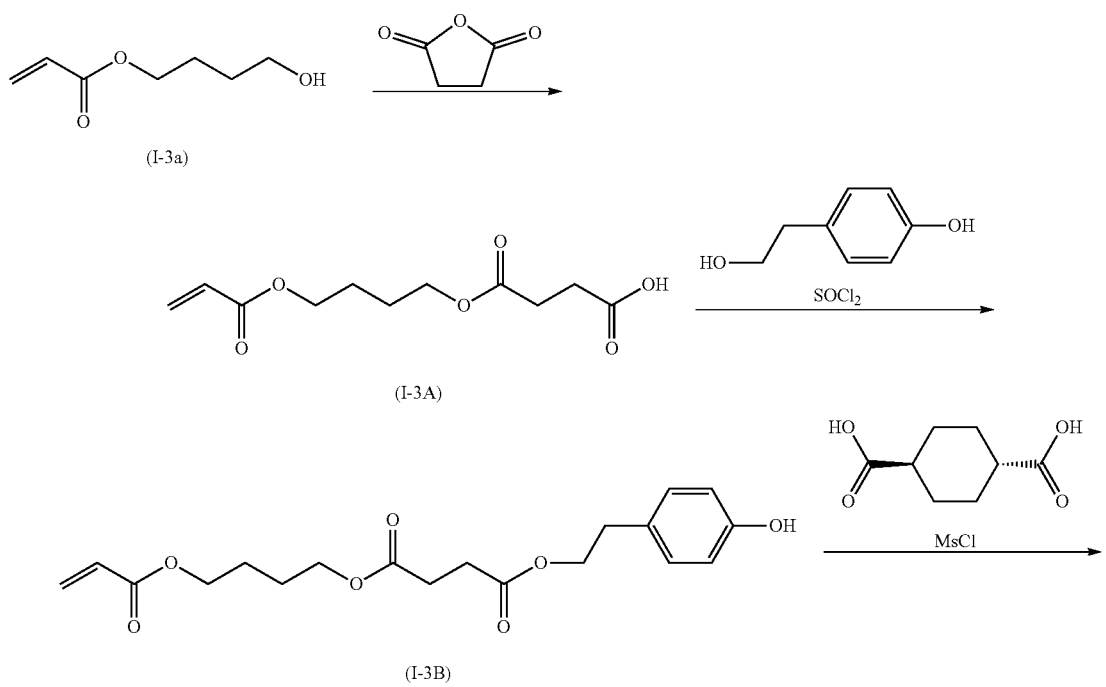

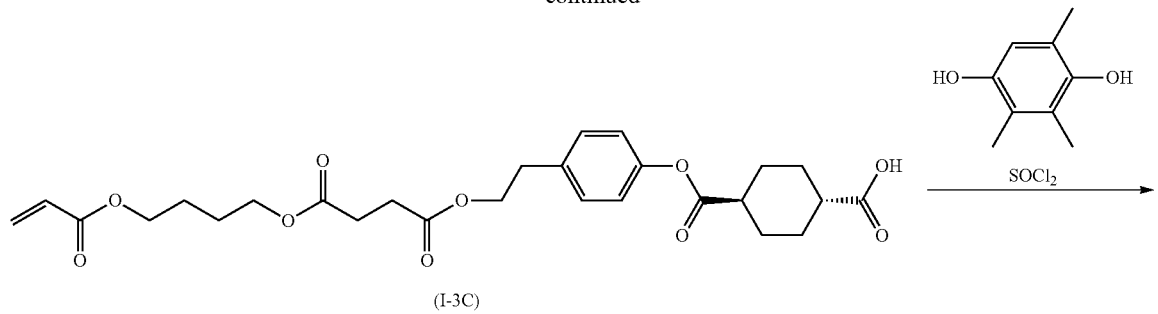

(I-3C)

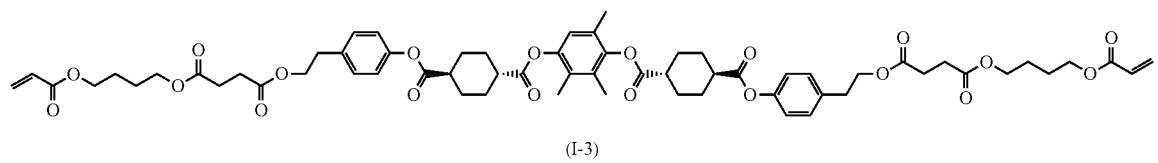

(I-3)

<Synthesis of Compound (I-3A)>

A compound (I-3A) was synthesized (yield: 92%) by the same method as that used for synthesizing the compound (I-2A), except that in the synthesis method of the compound (I-2A), the compound (I-2a) was changed to a compound (I-3a).

<Synthesis of Compound (I-3B)>

A compound (I-3B) was synthesized (yield: 94%) by the same method as that used for synthesizing the compound (I-1B), except that in the synthesis method of the compound (I-1B), the compound (I-1A) was changed to the compound (I-3A).

<Synthesis of Compound (I-3C)>

A compound (I-3C) was synthesized (yield: 70%) by the same method as that used for synthesizing the compound (I-1C), except that in the synthesis method of the compound (I-1C), the compound (I-1B) was changed to the compound (I-3B).

<Synthesis of Compound (I-3)>

A compound (I-3) was synthesized (yield: 88%) by the same method as that used for synthesizing the compound (I-1), except that in the synthesis method of the compound (I-1), the compound (I-1C) was changed to the compound (I-3C).

$^1$H-NMR of the obtained compound (I-3) is shown below.

$^1$H-NMR. (solvent: CDCl$_3$) δ (ppm): 1.45-1.72 (m, 8H), 1.72-1.80 (m, 8H), 2.05 (s, 3H), 2.06 (s, 3H), 2.10 (s, 3H), 2.10-2.30 (m, 8H), 2.33-2.45 (m, 2H), 2.47-2.65 (m, 2H), 2.62 (s, 8H), 2.93 (t, 4H), 4.10-4.22 (m, 8H), 4.30 (t, 4H), 5.83 (dd, 2H), 6.12 (dd, 2H), 6.41 (dd, 2H), 6.73 (s, 1H), 7.01 (d, 4H), 7.23 (d, 4H)

[Synthesis of Polymerizable Compound (I-4)]

According to the following scheme, a compound (I-4) was synthesized. The compound (I-4) is a compound obtained as a mixture of the compound represented by Formula (I-4) described above and the compound represented by Formula (I-5) described above.

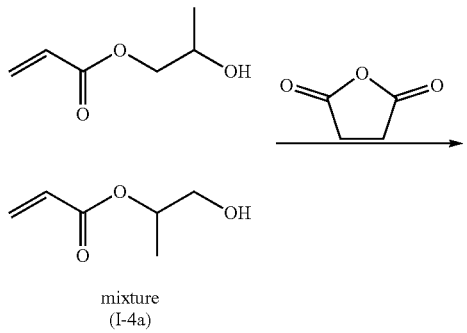

mixture
(I-4a)

-continued
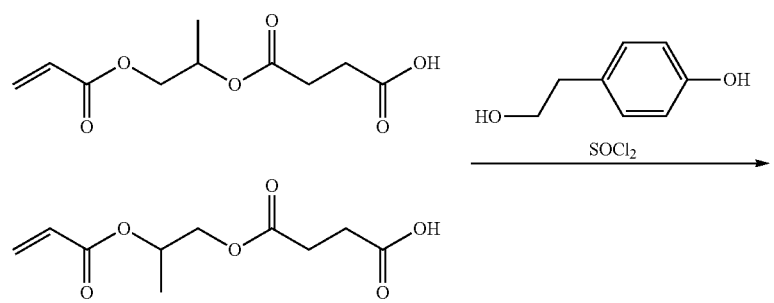
mixture
(I-4A)
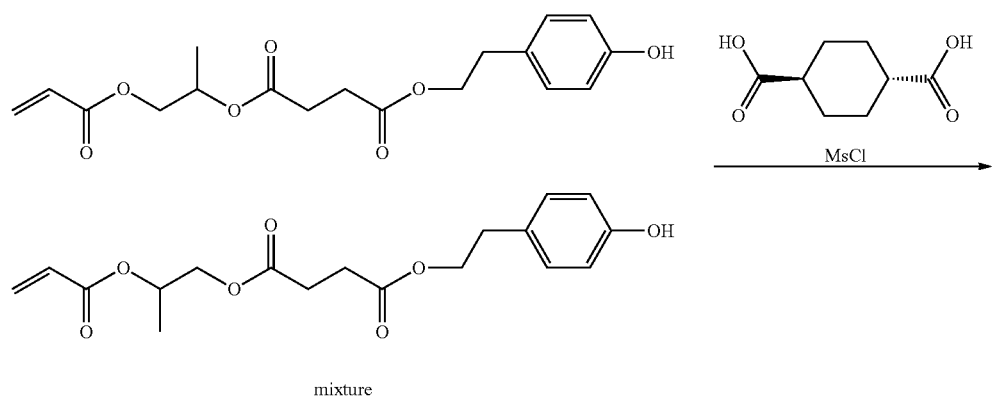
mixture
(I-4B)
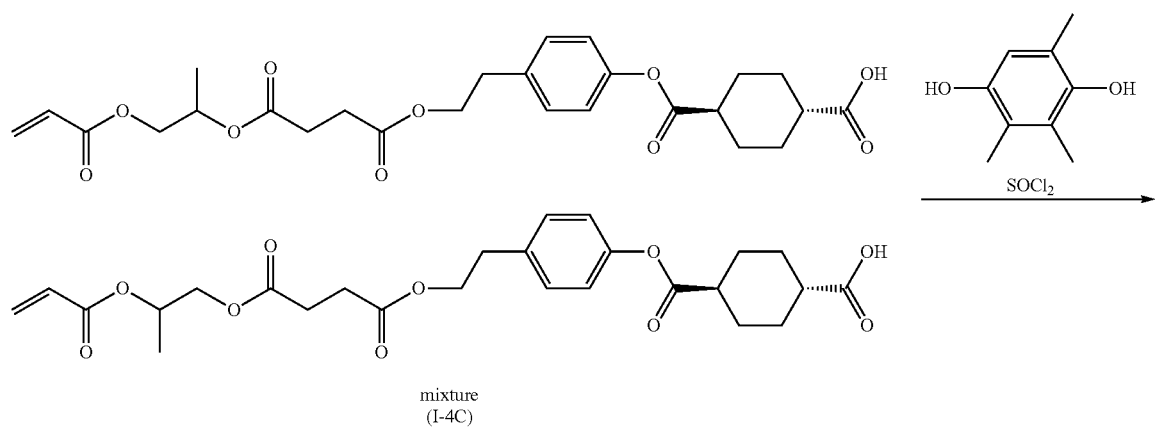
mixture
(I-4C)

-continued

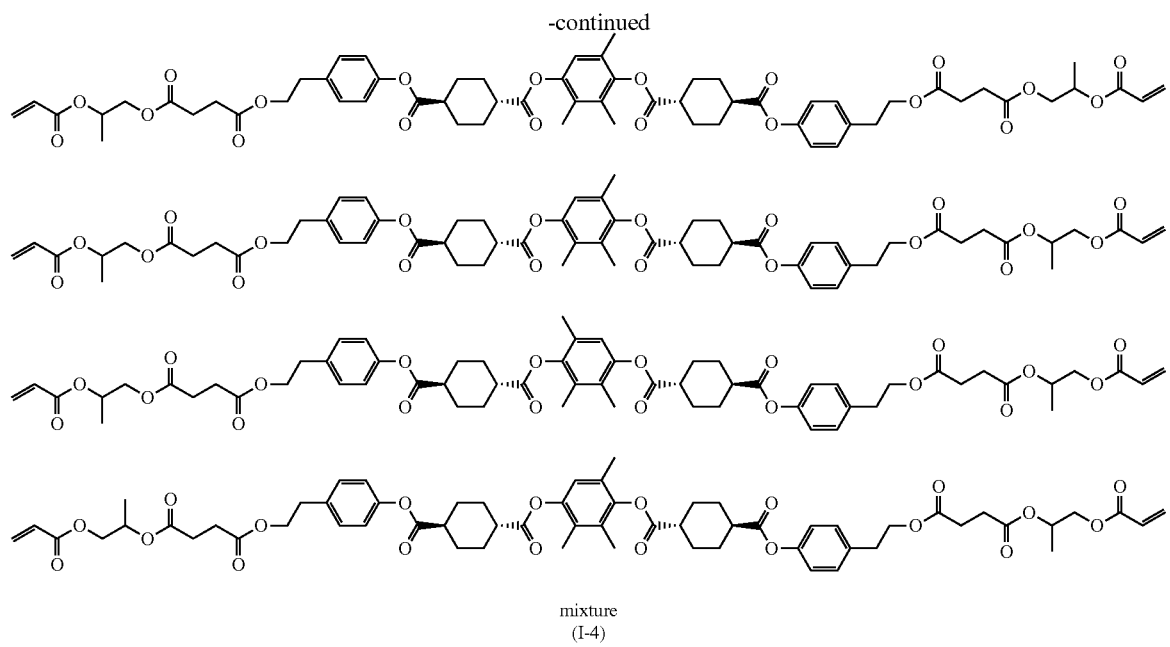

mixture
(I-4)

<Synthesis of Compound (I-4A)>
A compound (I-4A) was synthesized (yield: 99%) by the same method as that used for synthesizing the compound (I-2A), except that in the synthesis method of the compound (I-2A), the compound (I-2a) was changed to a compound (I-4a).

<Synthesis of Compound (I-4B)>
A compound (I-4B) was synthesized (yield: 91%) by the same method as that used for synthesizing the compound (I-1B), except that in the synthesis method of the compound (I-1B), the compound (I-1A) was changed to the compound (I-4A).

<Synthesis of Compound (I-4C)>
A compound (I-4C) was synthesized (yield: 67%) by the same method as that used for synthesizing the compound (I-1C), except that in the synthesis method of the compound (I-1C), the compound (I-1B) was changed to the compound (I-4B).

<Synthesis of Compound (I-4)>
A compound (I-4) was synthesized (yield: 80%) by the same method as that used for synthesizing the compound (I-1), except that in the synthesis method of the compound (I-1), the compound (I-1C) was changed to the compound (I-4C).

$^1$H-NMR of the obtained compound (I-4) is shown below.
$^1$H-NMR (solvent: CDCl$_3$) σ (ppm): 1.25-1.32 (m, 6H), 1.62-1.76 (m, 8H), 2.05 (s, 3H), 2.06 (s, 3H), 2.10 (s, 3H), 2.21-2.37 (m, 8H), 2.54-2.68 (m, 12H), 2.94 (t, 4H), 4.10-4.24 (m, 4H), 4.29 (t, 4H), 5.15-5.25 (m, 2H), 5.82-5.88 (m, 2H), 6.07-6.18 (m, 2H), 6.38-6.46 (m, 2H), 6.73 (s, 1H), 7.01 (d, 4H), 7.23 (d, 4H)

<Synthesis of Polymerizable Compound (I-5)>
According to the following scheme, a compound (I-5) was synthesized.

In the following scheme, the compound (I-5A) is a mixture just like the compound (I-4A) used for synthesizing the polymerizable compound (I-4) described above.

Furthermore, the compound (I-5) is the same compound as the compound represented by Formula (I-41) described above.

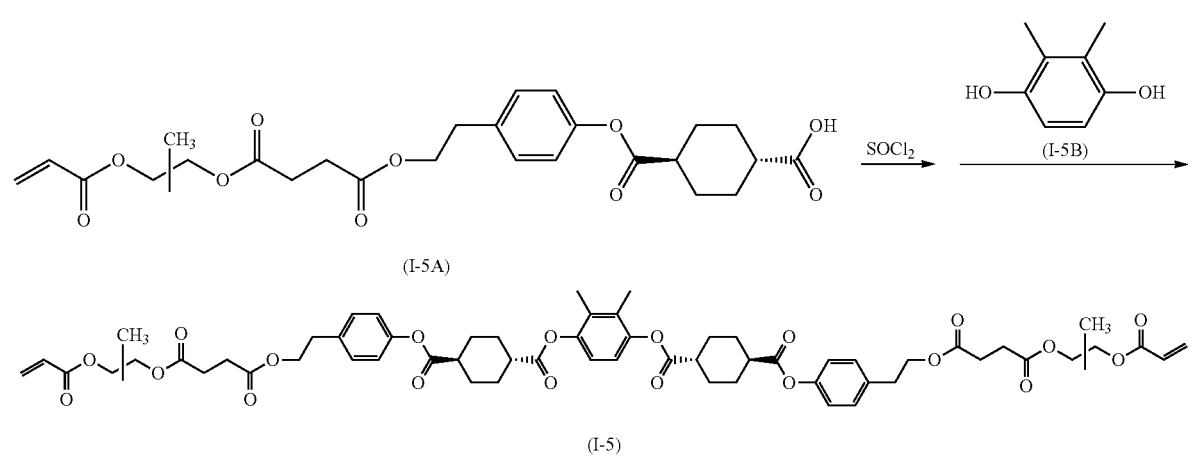

‹Synthesis of Compound (I-5)›

5.10 g (7.5 mmol) of the compound (I-5A) (74.54%), 21 ml of ethyl acetate, 5 ml of N,N-dimethylacetamide, and 10.6 mg of 2,6-di-t-butyl-4-methylphenol were mixed together and cooled such that the internal temperature decreased to 0° C. 0.94 g (7.9 mol) of thionyl chloride was

[Synthesis of Polymerizable Compound (I-6)]

According to the following scheme, a compound (I-6) was synthesized.

In the following scheme, the compound (I-6A) is a mixture just like the compound (I-4A) used for synthesizing the polymerizable compound (I-4) described above.

Furthermore, the compound (I-6) is the same compound as the compound represented by Formula (I-43) described above.

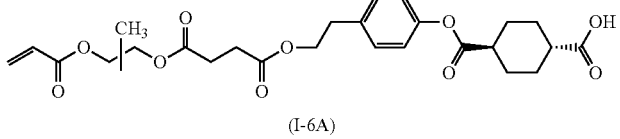

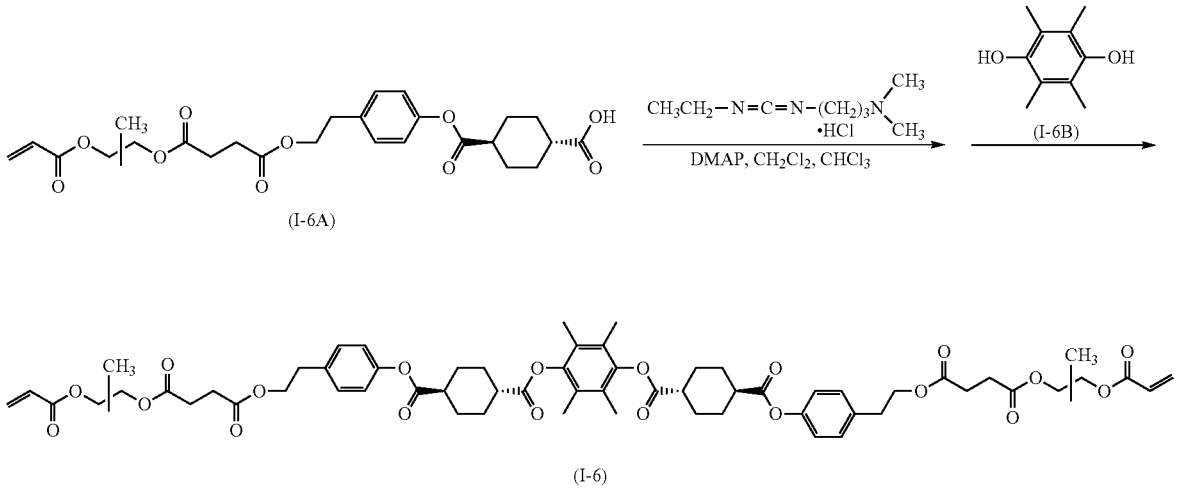

(I-6)

added dropwise to the mixture at an internal temperature of 0° C. to 5° C. The mixture was stirred for 60 minutes at 5° C., and then a solution containing 0.44 g (3.2 mmol) of dimethyl hydroquinone as the compound (I-5B), 5.6 ml of tetrahydrofuran, and 1.45 g (18.3 mmol) of pyridine was added dropwise thereto at an internal temperature of 0° C. to 8° C. The mixture was stirred for 60 minutes at 5° C., and then 39.2 mg of N,N-dimethylaminopyridine and 2.07 g (16.0 mmol) of N,N-diisopropylethylamine were added dropwise thereto at an internal temperature of 0° C. to 10° C. The mixture was stirred for 1.5 hours at an internal temperature of 15° C. to 20° C., and then 5 ml of ethyl acetate, 19 ml of water, and 1.6 ml of concentrated hydrochloric acid were added thereto for washing. The organic layer was washed with 15 ml of 15 wt % saline, and liquid separation was performed. Subsequently, the organic layer was washed with 15 ml of 15 wt % saline, and liquid separation was performed. Then, 1.56 g of anhydrous magnesium sulfate was added to the organic layer, and then the mixture was stirred for 30 minutes. Thereafter, 1.56 g of silica gel (WAKOGEL C-200) was added thereto, and the mixture was stirred for 30 minutes. Then, 0.5 g of activated carbon was added thereto, and the mixture was stirred for 30 minutes. The magnesium sulfate, the silica gel, and the activated carbon were separated by filtration, the solvent was distilled away under reduced pressure, and then recrystallization was performed using 30 nil of methanol, thereby obtaining 1.2 g of a compound (I-5) (yield: 34.2%).

$^1$H-NMR of the obtained compound (I-5) is shown below.

$^1$H-NMR (solvent: CDCl$_3$) δ (ppm): 1.26 (m, 6H), 1.64-1.70 (m, 8H), 2.09 (s, 6H), 2.27-2.30 (m, 8H), 2.57-2.63 (m, 12H), 2.94 (t, j=6.0 Hz, 4H), 4.12-4.26 (m, 4H), 4.29 (t, j=6.0 Hz, 4H), 5.17-5.30 (m, 2H), 5.82-5.88 (m, 2H), 6.07-6.18 (m, 2H), 6.38-6.46 (m, 2H), 6.86 (s, 2H), 7.01 (d, j=9.01 Hz, 4H), 7.22 (d, j=9.0 Hz, 4H)

‹Synthesis of Compound (I-6)›

9.78 g (14.4 mmol) of the compound (I-6A) (74.54%), 15 ml of dichloromethane, 4 ml of chloroform, 44 mg (0.36 mmol) of N,N-dimethylaminopyridine, and 4.16 g (21.7 mmol) of 1-(3-dimethylaminopropyl)-3-ethylcarbodiimide hydrochloride were mixed together and stirred for 10 minutes at room temperature. Then, 0.6 g (3.61 mmol) of tetramethylhydroquinone as the compound (I-6B) was added thereto, and the mixture was further stirred for 5 hours. 50 mL of hexane and 150 mL of 1 N hydrochloric acid were added to the obtained solution, the organic layer was washed, and then liquid separation was performed. The organic layer was washed with 100 ml of 15% saline, and liquid separation was performed. Thereafter, the organic layer was washed with 100 ml of 15% saline, and liquid separation was performed. The solvent was distilled away under reduced pressure, 40 ml of ethyl acetate and 1.56 g of anhydrous magnesium sulfate were added thereto, and the mixture was stirred for 30 minutes. Thereafter, 1.56 g of silica gel (WAKOGEL C-200) was then added thereto, and the mixture was stirred for 30 minutes. Then, the magnesium sulfate and the silica gel were separated by filtration, the solvent was distilled away under reduced pressure, and then recrystallization was performed using 50 ml of methanol. Subsequently, by performing silica gel column chromatography (hexane/ethyl acetate=½), 1.3 g of a compound (I-6) was obtained (yield: 31.6%).

$^1$H-NMR of the obtained compound (I-6) is shown below.

$^1$H-NMR (solvent: CDCl$_3$) δ (ppm): 1.26 (m, 6H), 1.64-1.70 (m, 8H), 2.09 (s, 12H), 2.27-2.30 (m, 8H), 2.57-2.63 (m, 12H), 2.94 (t, j=6.0 Hz, 4H), 4.12-4.26 (m, 4H), 4.29 (t, j=6.0 Hz, 4H), 5.17-5.30 (m, 2H), 5.82-5.88 (m, 2H), 6.07-6.18 (m, 2H), 6.38-6.46 (m, 2H), 7.01 (d, j=9.0 Hz, 4H), 7.22 (d, j=9.0 Hz, 4H)

[Synthesis of Polymerizable Compound (I-7)]

According to the following scheme, a compound (I-7) was synthesized. The compound (I-7) is the same compound as the compound represented by Formula (I-66) described above.

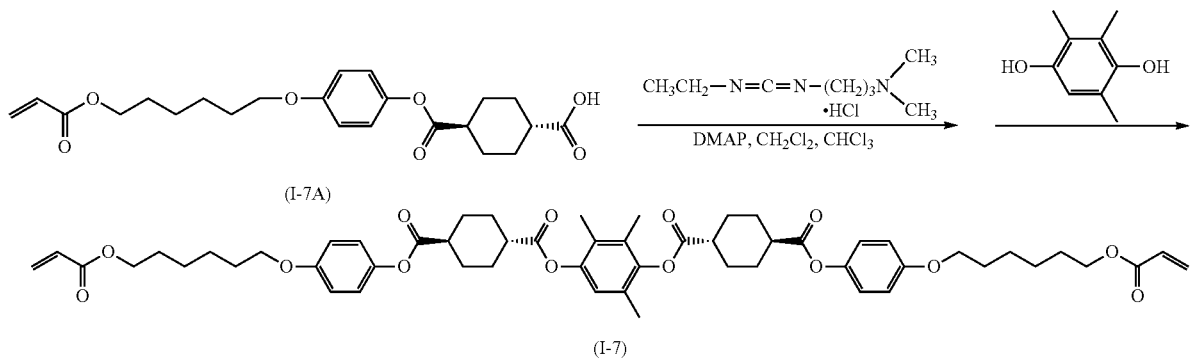

<Synthesis of Compound (I-7A)>

A compound (I-7A) was synthesized by the method described in paragraphs "0244" to "0246" in JP2010-031223A.

<Synthesis of Compound (I-7)>

5.82 g (14.4 mmol) of the compound (I-7A), 15 ml of dichloromethane, 4 ml of chloroform, 44 mg (0.36 mmol) of N,N-dimethylaminopyridine, and 4.16 g (21.7 mmol) of 1-(3-dimethylaminopropyl)-3-ethylcarbodiimide hydrochloride were mixed together and stirred for 10 minutes at room temperature. Then, 0.6 g (3.94 mmol) of trimethylhydroquinone was added thereto, and the mixture was further stirred for 5 hours. 50 mL of hexane and 150 ml of 1 N hydrochloric acid were added to the obtained solution, the organic layer was washed, and then liquid separation was performed. The organic layer was washed with 100 ml of 15% saline, and liquid separation was performed. Thereafter, the organic layer was washed with 100 ml of 15% saline, and liquid separation was performed. The solvent was distilled away under reduced pressure, and 40 ml of ethyl acetate and 1.56 g of anhydrous magnesium sulfate were added thereto, and the mixture was stirred for 30 minutes. Subsequently, 1.56 g of silica gel (WAKOGEL C-200) was then added thereto, and the mixture was stirred for 30 minutes. Then, the magnesium sulfate and the silica gel were separated by filtration, the solvent was distilled away under reduced pressure, and then recrystallization was performed using 50 ml of methanol. Subsequently, by performing silica gel column chromatography (hexane/ethyl acetate=1/2), 1.0 g of a compound (I-7) was obtained (yield: 26.6%).

$^1$H-NMR of the obtained compound (I-7) is shown below.

$^1$H-NMR (solvent: CDCl$_3$) σ (ppm): 1.43-1.54 (m, 8H), 1.62-1.76 (m, 16H), 2.06 (s, 3H), 2.08 (s, 3H), 2.15 (s, 3H), 2.27 (m, 4H), 3.97 (t, 4H), 4.06 (t, 4H), 5.59 (d, 2H), 6.05 (t, 2H), 6.27 (d, 2H), 6.97 (s, 1H), 6.88 (d, 4H), 6.96 (d, 4H)

[Synthesis of Polymerizable Compound (X-1)]

According to the following scheme, a compound (X-1) was synthesized.

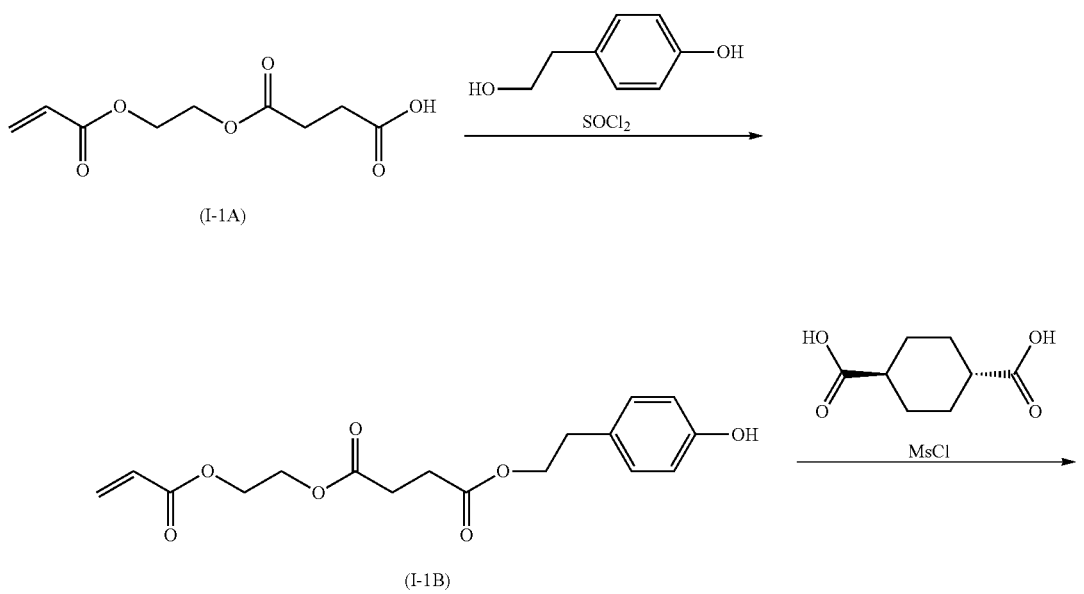

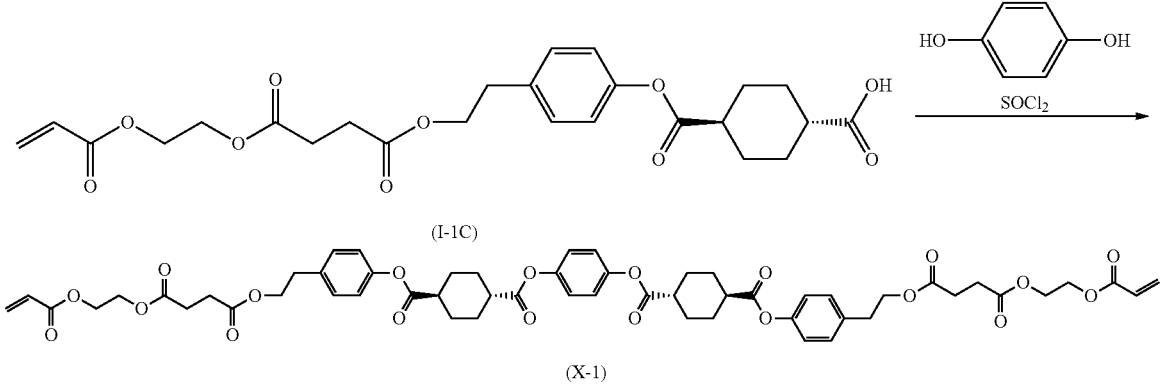

(I-1C)

(X-1)

<Synthesis of Compound (X-1)>

Until the compound (I-1C) was obtained, the same procedure as that performed for synthesizing the compound (I-1) was carried out.

14.51 g (0.021 mol) of the compound (I-1C) (purity: 74.54%), 62 ml of ethyl acetate, ml of N,N-dimethylacetamide, and 32.4 mg of 2,6-di-t-butyl-4-methylphenol were mixed together and cooled such that the internal temperature decreased to 0° C. 2.66 g (0.022 mol) of thionyl chloride was added dropwise to the mixture at an internal temperature of 0° C. to 5° C. The mixture was stirred for 60 minutes at 5° C., and then 1.0 g (0.009 mol) of hydroquinone and 10 ml of an ethyl acetate solution were added dropwise thereto at an internal temperature of 0° C. to 8° C. Thereafter, 5.77 g (0.045 mol) of N,N-diisopropylethylamine was added dropwise thereto at an internal temperature of 0° C. to 10° C. The mixture was stirred for 4.5 hours at an internal temperature of 15° C. to 20° C. and cooled such that the internal temperature decreased to 0° C. 3.04 g (0.020 mop of 1,8-diazabicyclo[5.4.0]-7-undecene was added dropwise thereto at an internal temperature of 0° C. to 5° C. The mixture was stirred for 1.3 hours at an internal temperature of 15° C. to 20° C., and then 150 ml of ethyl acetate, 100 ml of water, and 10 ml of concentrated hydrochloric acid were added thereto for washing. The organic layer was washed with 100 ml of aqueous saturated saline, and liquid separation was performed. Subsequently, the organic layer was washed with 100 ml of aqueous saturated saline and 50 ml of 7.5 wt % aqueous sodium bicarbonate, and liquid separation was performed. Furthermore, the organic layer was washed with 100 ml of saturated saline and then dried over anhydrous magnesium sulfate. 10 g of silica gel (WAKO-GEL C-200) was added thereto, and the mixture was stirred for 60 minutes. The magnesium sulfate and the silica gel were separated by filtration, the solvent was distilled away under reduced pressure, and recrystallization was performed using 100 ml of methanol, thereby obtaining 3.0 g of a compound (X-1) (yield: 30.4%).

$^1$H-NMR of the obtained compound (X-1) is shown below.

$^1$H-NMR (solvent: CDCl$_3$) σ (ppm): 1.25-1.32 (m, 8H), 1.62-1.76 (m, 8H), 2.21-2.37 (m, 8H), 2.54-2.68 (m, 12H), 2.94 (t, 4H), 4.10-4.24 (m, 4H), 4.29 (t, 4H), 5.15-5.25 (m, 2H), 5.82-5.88 (m, 2H), 6.07-6.18 (m, 2H), 6.38-6.46 (m, 2H), 7.00-7.03 (m, 4H), 7.10 (s, 4H), 7.21-7.24 (m, 4H)

[Synthesis of Polymerizable Compound (X-2)]

According to the following scheme a compound (X-2) was synthesized.

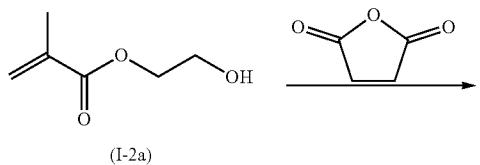

(I-2a)

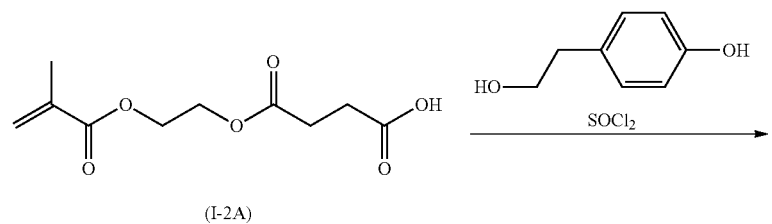

(I-2A)

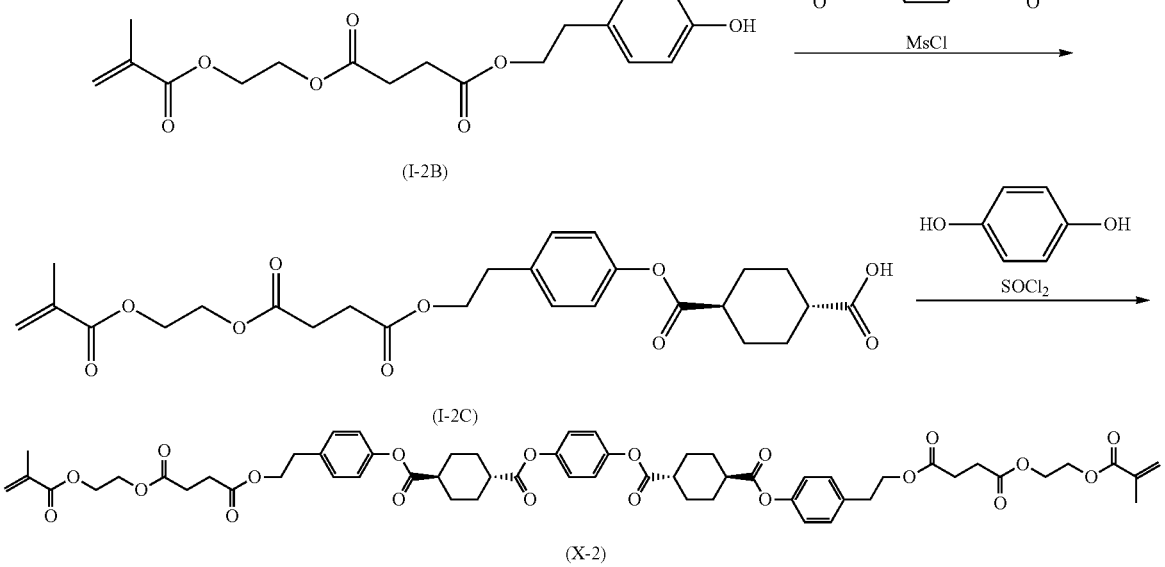

<Synthesis of Compound (X-2)>

Until the compound (I-2C) was obtained, the same procedure as that performed for synthesizing the compound (I-2) was carried out.

The compound (X-2) was synthesized (yield: 80%) by the same method as that used for synthesizing the compound (X-1), except that in the synthesis method of the compound (X-1), the compound (I-1C) was changed to the compound (I-2C).

$^1$H-NMR of the obtained compound (X-2) is shown below.

$^1$H-NMR (solvent: CDCl$_3$) σ (ppm): 1.25-1.32 (m, 8H), 1.62-1.76 (m, 8H), 1.95 (s, 6H), 2.21-2.37 (m, 8H), 2.54-2.68 (m, 12H), 2.94 (t, 4H), 4.10-4.24 (m, 4H), 4.29 (t, 4H), 5.15-5.25 (m, 2H), 5.59 (s, 2H), 6.12 (s, 2H), 7.00-7.03 (m, 4H), 7.10 (s, 4H), 7.21-7.24 (m, 4H)

[Synthesis of Polymerizable Compound (X-3)]

According to the following scheme, a compound (X-3) was synthesized,

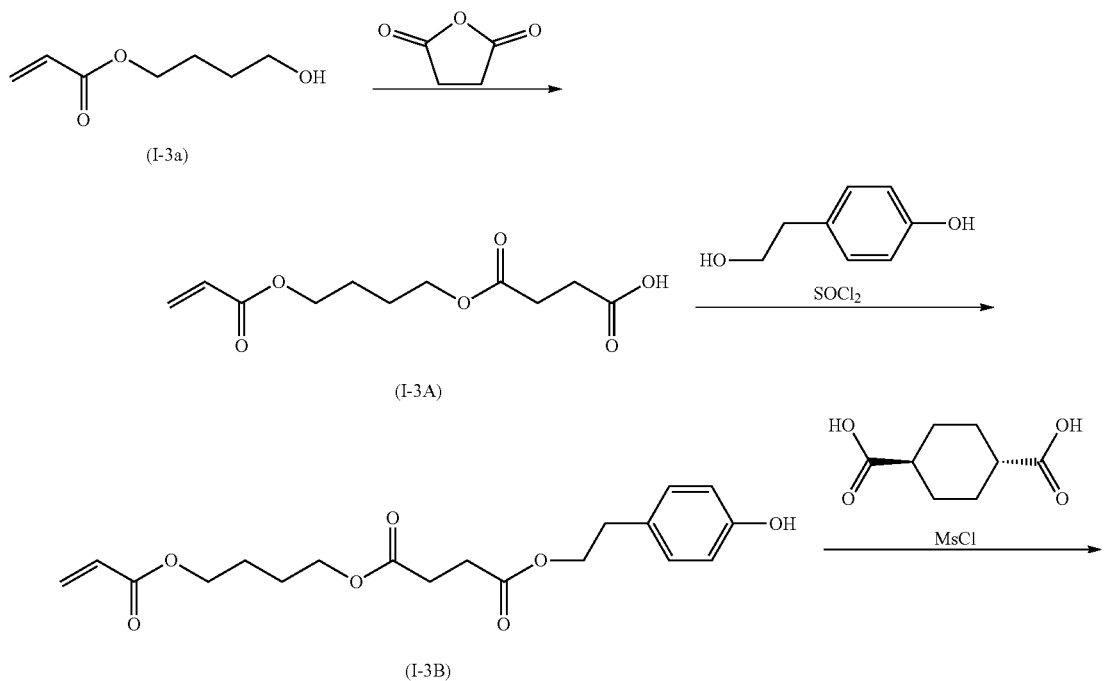

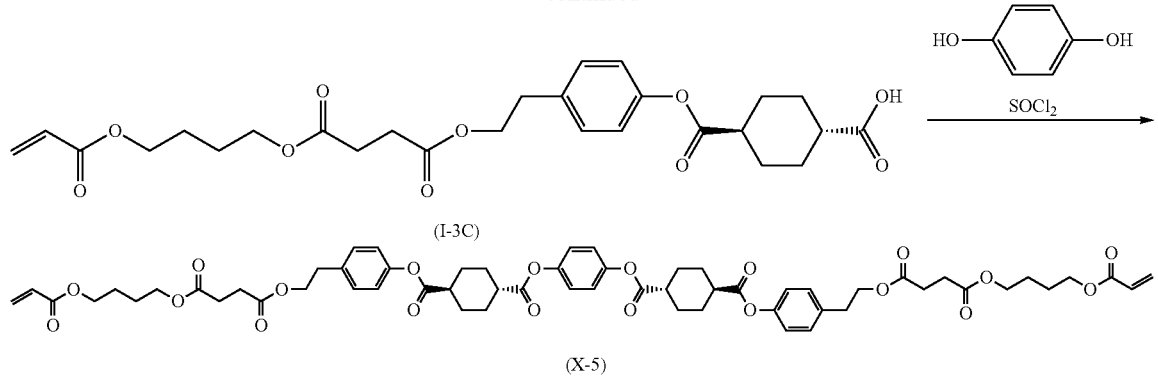

<Synthesis of Compound (X-3)>

Until the compound (I-3C) was obtained, the same procedure as that performed for synthesizing the compound (I-3) was carried out.

The compound (X-3) was synthesized (yield: 88%) by the same method as that used for synthesizing the compound (X-1), except that in the synthesis method of the compound (X-1), the compound (I-1C) was changed to the compound (I-3C).

$^1$H-NMR of the obtained compound (X-3) is shown below.

$^1$H-NMR (solvent: CDCl$_3$) δ (ppm): 1.45-1.72 (m, 8H), 1.72-1.80 (m, 8H), 2.10-2.30 (m, 8H), 2.33-2.45 (m, 2H), 2.47-2.65 (m, 2H), 2.62 (s, 8H), 2.93 (t, 4H), 4.10-4.22 (m, 8H), 4.30 (t, 4H), 5.83 (dd, 2H), 6.12 (dd, 2H), 6.41 (dd, 2H), 7.00-7.03 (m, 4H), 7.10 (s, 4H), 7.21-7.24 (m, 4H)

[Synthesis of Polymerizable Compound (X-4)]

According to the following scheme, a compound (X-4) was synthesized.

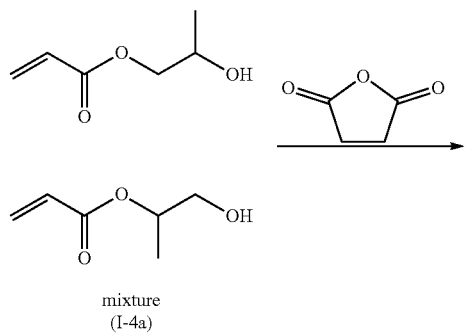

mixture
(I-4a)

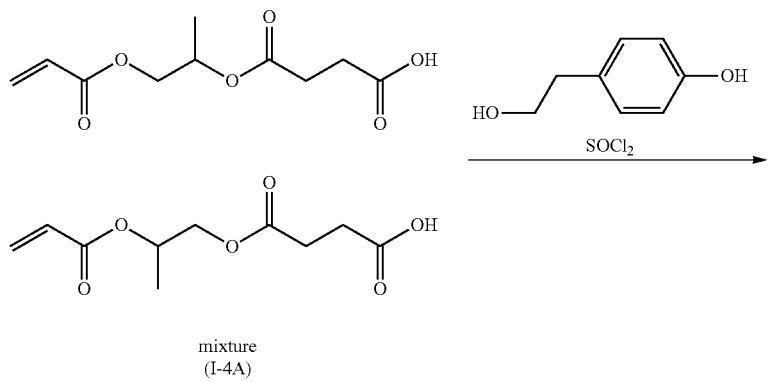

mixture
(I-4A)

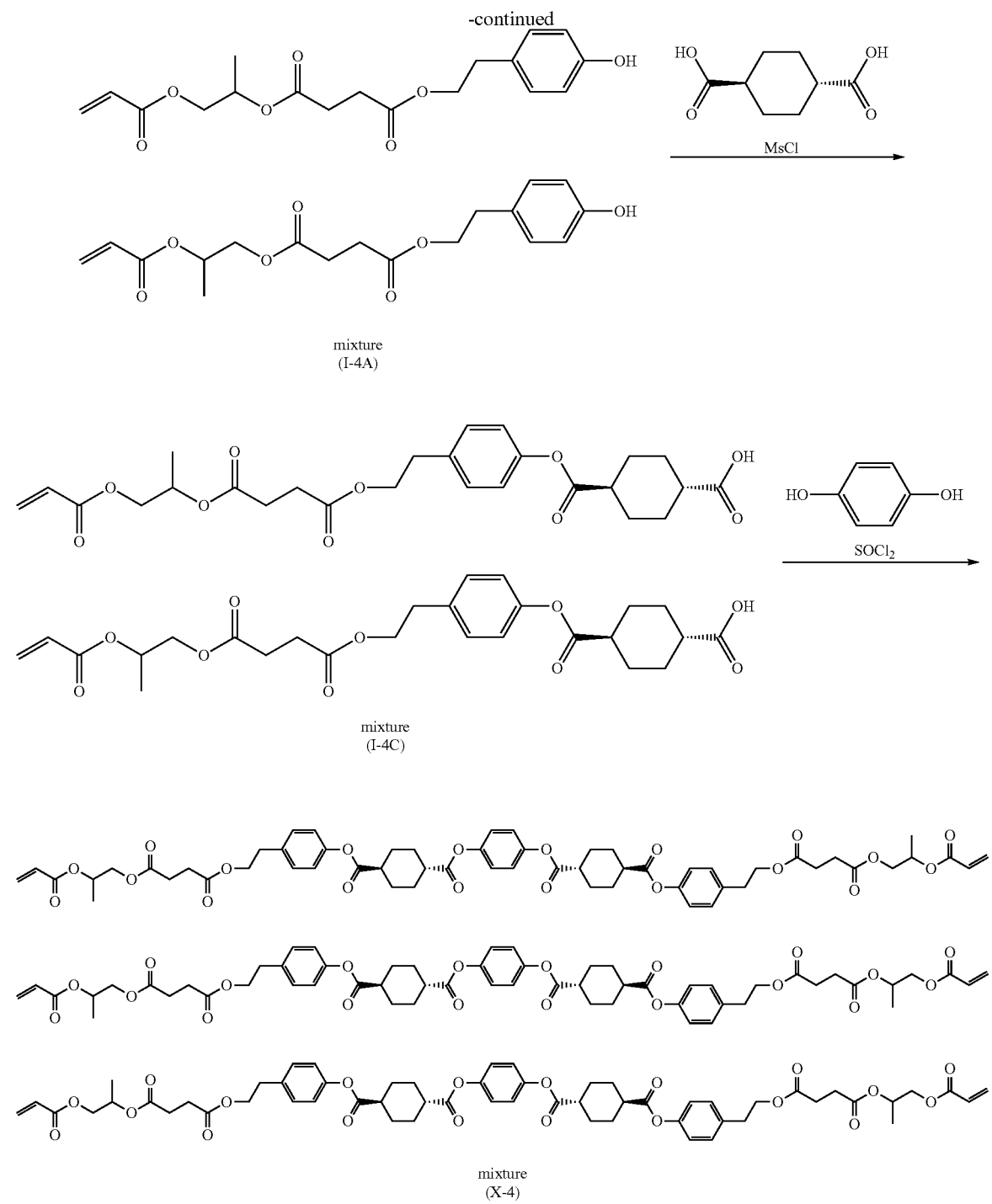

<Synthesis of Compound (X-4)>

Until the compound (I-4C) was obtained, the same procedure as that performed for synthesizing the compound (I-4) was carried out.

The compound (X-4) was synthesized (yield: 80%) by the same method as that used for synthesizing the compound (X-1), except that in the synthesis method of the compound (X-1), the compound (I-1C) was changed to the compound (I-4C).

$^1$H-NMR of the obtained compound (X-4) is shown below.

$^1$H-NMR (solvent: CDCl$_3$) σ (ppm): 1.26-1.30 (m, 6H), 1.64-1.70 (m, 8H), 2.27-2.30 (m, 8H), 2.57-2.63 (m, 12H), 2.94 (t, j=6.0 Hz, 4H), 4.12-4.26 (m, 4H), 4.29 (t, j=6.0 Hz, 4H), 5.17-5.40 (m, 2H), 5.82-5.88 (M, 2H), 6.07-6.18 (m, 2H), 6.38-6.46 (M, 2H), 7.00-7.03 (m, 4H), 7.10 (s, 4H), 7.21-7.24 (m, 4H)

[Synthesis of Polymerizable Compound (X-5)]

According to the following scheme, a compound (X-5) was synthesized.

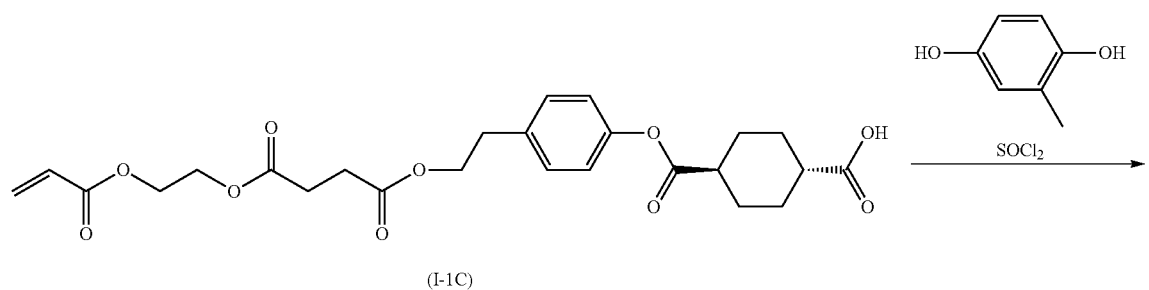

(I-1C)

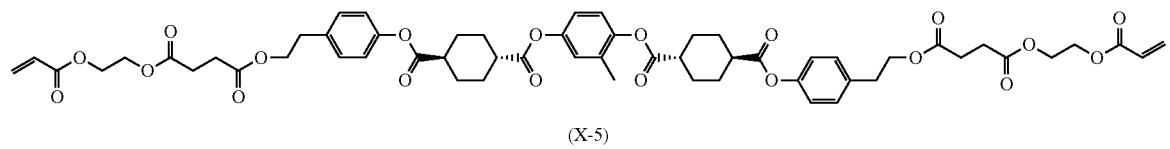

(X-5)

<Synthesis of Compound (X-5)>

The compound (X-5) was synthesized (yield: 68%) by the same method as that used for synthesizing the compound (X-1), except that in the synthesis method of the compound (X-1), hydroquinone was changed to methyl hydroquinone.

$^1$H-NMR of the obtained compound (X-5) is shown below.

$^1$H-NMR (solvent: CDCl$_3$) σ (ppm): 1.25-1.32 (m, 8H), 1.62-1.76 (m, 8H), 2.18 (s, 3H), 2.21-2.37 (m, 8H), 2.54-2.68 (m, 12H), 2.94 (t, 4H), 4.10-4.24 (m, 4H), 4.29 (t, 4H), 5.15-5.25 (m, 2H), 5.82-5.88 (m, 2H), 6.07-6.18 (m, 2H), 6.38-6.46 (m, 2H), 6.90-7.00 (m, 3H), 7.01 (d, 4H), 7.23 (d, 4H)

[Synthesis of Polymerizable Compound (X-6)]

According to the following scheme, a compound (X-6) was synthesized,

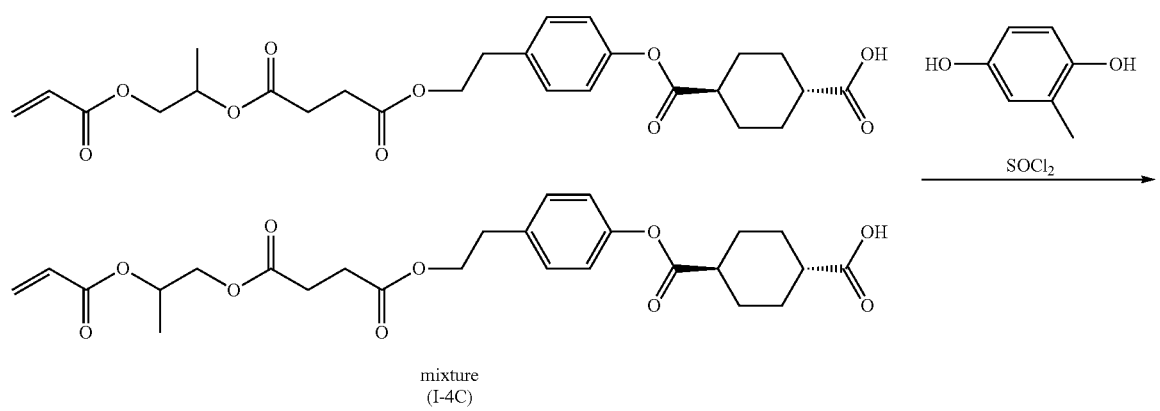

mixture
(I-4C)

-continued

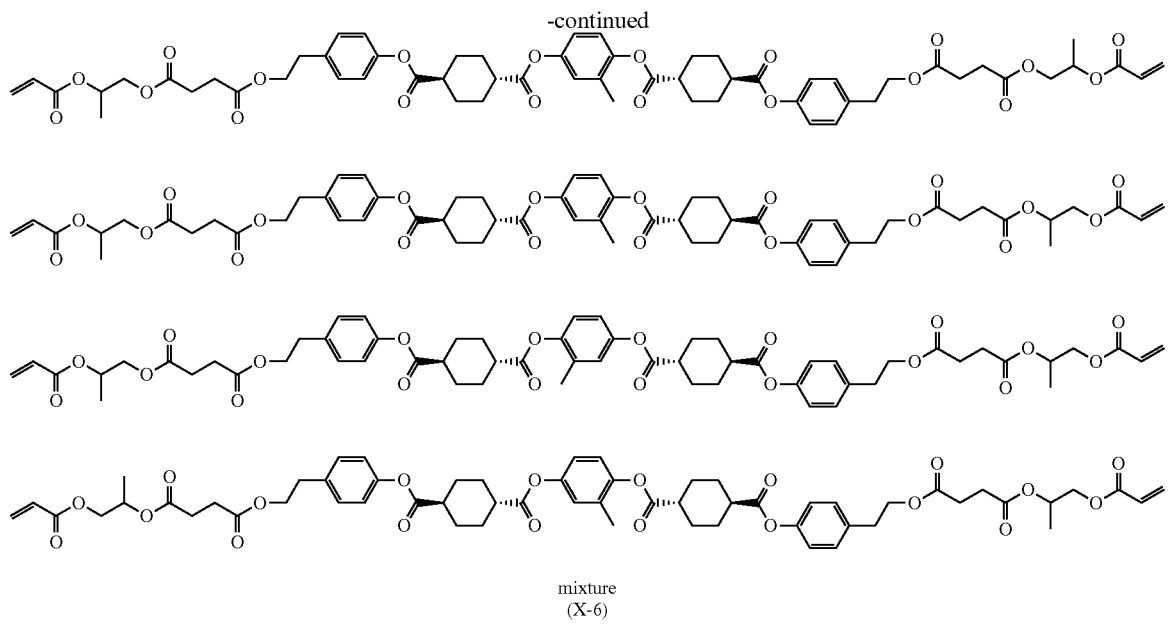

mixture
(X-6)

<Synthesis of Compound (X-6)>

Until the compound (I-4C) was obtained, the same procedure as that performed for synthesizing the compound (I-4) was carried out.

The compound (X-6) was synthesized (yield: 62%) by the same method as that used for synthesizing the compound (X-1), except that in the synthesis method of the compound (X-1), the compound (I-1C) was changed to the compound (I-4C), and hydroquinone was changed to methyl hydroquinone.

$^1$H-NMR of the obtained compound (X-6) is shown below.

$^1$H-NMR (solvent: CDCl$_3$) σ (ppm): 1.25-1.30 (m, 6H), 1.60-1.75 (m, 8H), 2.18 (s, 3H), 2.21-2.37 (m, 8H), 2.52-2.68 (m, 12H), 2.94 (t, 4H), 4.10-4.24 (m, 4H), 4.29 (t, 4H), 5.15-5.25 (m, 2H), 5.82-5.88 (m, 2H), 6.07-6.18 (m, 2H), 6.38-6.46 (m, 2H), 6.90-7.00 (m, 3H), 7.01 (d, 4H), 7.23 (d, 4H)

Example 1

<Formation of Photo-Alignment Film P-1>

According to Example 1 in JP2001-141926A, iodine was caused to be adsorbed onto a stretched polyvinyl alcohol film, thereby preparing a polarizer 1 having a film thickness of 20 μM. One surface of the polarizer 1 was coated with a coating solution 1 for photo-alignment, which was prepared with reference to the description of Example 3 in JP2012-155308A, by using a #2 bar.

After coating, the solvent was removed by drying, thereby forming a photoisomerization composition layer 1.

The obtained photoisomerization composition layer 1 was irradiated with polarized ultraviolet rays (500 mJ/cm$^2$, using a 750 \V ultrahigh-pressure mercury lamp), thereby forming a photo-alignment film P-1.

<Formation of Optically-Anisotropic Layer 1>

The photo-alignment film P-1 was coated with a coating solution 1 for an optically-anisotropic layer composed as below by a spin coating method, thereby forming a liquid crystal composition layer 1.

The formed liquid crystal composition layer 1 was heated on a hot plate such that a nematic phase (Ne phase) was created first, and then cooled to 60° C. such that the alignment was fixed to create a smectic A phase (SmA phase).

Thereafter, the alignment was fixed by irradiating the layer with ultraviolet rays at 60° C., and in this way, an optically-anisotropic layer was formed, and an optical film was prepared.

| Coating solution 1 for optically-anisotropic layer | |
|---|---|
| Liquid crystal compound L-1 shown below | 43.75 parts by mass |
| Liquid crystal compound L-2 shown below | 43.75 parts by mass |
| Polymerizable compound (I-1) shown above | 12.50 parts by mass |
| Polymerization initiator S-1 (oxime type) shown below | 3.00 parts by mass |
| Leveling agent (compound T-1 shown below) | 0.20 parts by mass |
| Methyl ethyl ketone | 219.30 parts by mass |

Coating solution 1 for optically-anisotropic layer

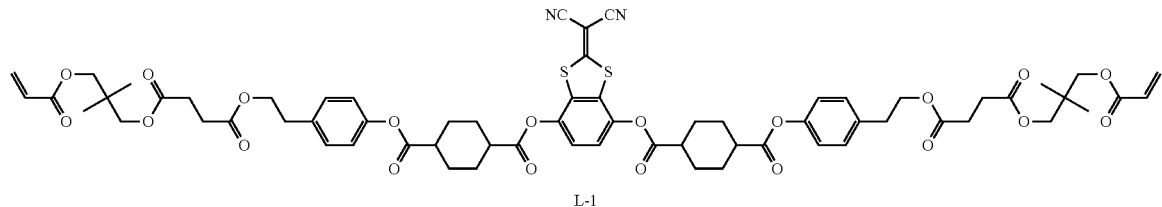 [SMILES: C=CC(=O)OCC(C)(C)COC(=O)CCC(=O)OCCc1ccc(OC(=O)C2CCC(C(=O)Oc3ccc(OC(=O)C4CCC(C(=O)Oc5ccc(CCOC(=O)CCC(=O)OCC(C)(C)COC(=O)C=C)cc5)CC4)c4c3SC(=C(C#N)C#N)S4)CC2)cc1]

L-1

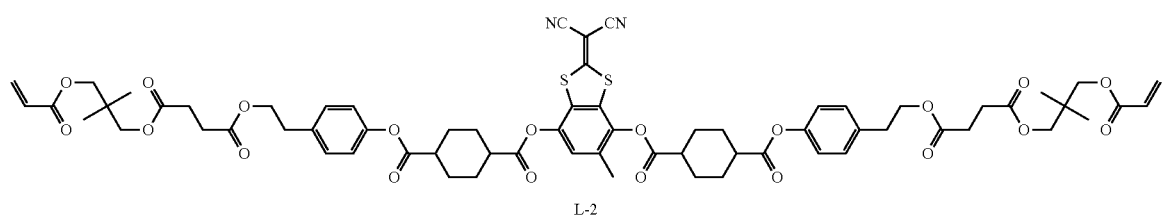 [SMILES: C=CC(=O)OCC(C)(C)COC(=O)CCC(=O)OCCc1ccc(OC(=O)C2CCC(C(=O)Oc3cc(C)c(OC(=O)C4CCC(C(=O)Oc5ccc(CCOC(=O)CCC(=O)OCC(C)(C)COC(=O)C=C)cc5)CC4)c4c3SC(=C(C#N)C#N)S4)CC2)cc1]

L-2

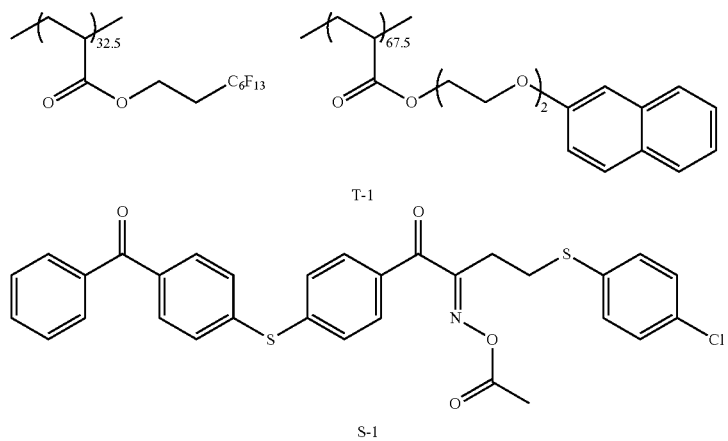

T-1

S-1

Example 2

An optical film was prepared by the same method as that in Example 1, except that the polymerizable compound (I-2) was used instead of the polymerizable compound (I-1) used in Example 1.

Example 3

An optical film was prepared by the same method as that in Example 1, except that the polymerizable compound (I-3) was used instead of the polymerizable compound (I-1) used in Example 1.

Example 4

An optical film was prepared by the same method as that in Example 1, except that the polymerizable compound (I-4) was used instead of the polymerizable compound (I-1) used in Example 1.

Example 5

An optical film was prepared by the same method as that in Example 1, except that the polymerizable compound (I-5) was used instead of the polymerizable compound (I-1) used in Example 1.

Example 6

An optical film was prepared by the same method as that in Example 1, except that the polymerizable compound (I-6) was used instead of the polymerizable compound (I-1) used in Example 1.

Example 7

An optical film was prepared by the same method as that in Example 1, except that a coating solution 2 for an optically-anisotropic layer composed as below was used instead of the coating solution 1 for an optically-anisotropic layer in Example 1.

| Coating solution 2 for optically-anisotropic layer | |
|---|---:|
| Liquid crystal compound L-6 shown below | 87.50 parts by mass |
| Polymerizable compound (I-7) shown above | 12.50 parts by mass |
| Polymerization initiator S-1 (oxime type) shown above | 3.00 parts by mass |
| Leveling agent (compound T-1 shown above) | 0.20 parts by mass |
| Methyl ethyl ketone | 219.30 parts by mass |

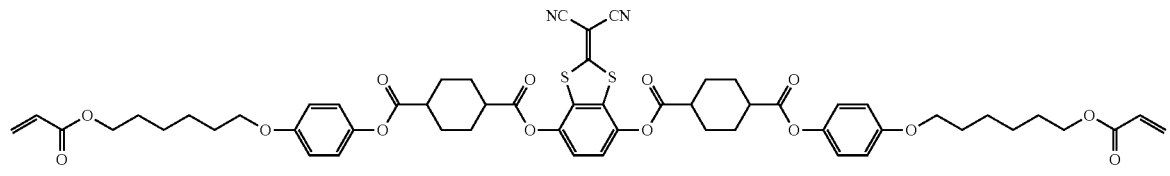

L-6

Example 8

An optical film was prepared by the same method as that in Example 1, except that a coating solution 3 for an optically-anisotropic layer composed as below was used instead of the coating solution 1 for an optically-anisotropic layer in Example 1.

| Coating solution 3 for optically-anisotropic layer | |
|---|---:|
| Liquid crystal compound L-7 shown below | 87.50 parts by mass |
| Polymerizable compound (I-7) shown above | 12.50 parts by mass |
| Polymerization initiator S-1 (oxime type) shown above | 3.00 parts by mass |
| Leveling agent (compound T-1 shown above) | 0.20 parts by mass |
| Methyl ethyl ketone | 219.30 parts by mass |

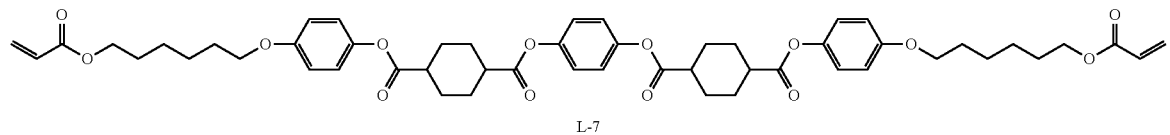 [SMILES: C=CC(=O)OCCCCCCOc1ccc(OC(=O)C2CCC(C(=O)Oc3ccc(OC(=O)C4CCC(C(=O)Oc5ccc(OCCCCCCOC(=O)C=C)cc5)CC4)cc3)CC2)cc1]

L-7

Comparative Example 1

An optical film was prepared by the same method as that in Example 1, except that the polymerizable compound (I-1) was not used, and the amount of each of the liquid crystal compound L-1 and the liquid crystal compound L-2 used was changed to 50.0 parts by mass.

Comparative Example 2

An optical film was prepared by the same method as that in Example 1, except that the polymerizable compound (X-1) was used instead of the polymerizable compound (I-1).

Comparative Example 3

An optical film was prepared by the same method as that in Example 1, except that the polymerizable compound (X-2) was used instead of the polymerizable compound (I-1).

Comparative Example 4

An optical film was prepared by the same method as that in Example 1, except that the polymerizable compound (X-3) was used instead of the polymerizable compound (I-1).

Comparative Example 5

An optical film was prepared by the same method as that in Example 1, except that the polymerizable compound (X-4) was used instead of the polymerizable compound (I-1).

Comparative Example 6

An optical film was prepared by the same method as that in Example 1, except that the polymerizable compound (X-5) was used instead of the polymerizable compound (I-1).

Comparative Example 7

An optical film was prepared by the same method as that in Example 1, except that the polymerizable compound (X-6) was used instead of the polymerizable compound (I-1).

Comparative Example 8

An optical film was prepared by the same method as that in Example 7, except that the polymerizable compound (I-7) was not used, and the amount of the liquid crystal compound L-6 used was changed to 100 parts by mass.

Comparative Example 9

An optical film was prepared by the same method as that in Example 8, except that the polymerizable compound (I-7) was not used, and the amount of the liquid crystal compound L-7 used was changed to 100 parts by mass.

Each of the optical films prepared in the examples and comparative examples described above was immersed in warm water with a temperature of 50° C. for 30 minutes or longer, and the softened polarizer 1 was removed so as to isolate the optically-anisotropic layer.

For each of the optically-anisotropic layers, in-plane retardation at wavelengths of 450 nm and 550 nm was measured using Axo Scan (OPMF-1, manufactured by Axometrics, Inc.), and Re (450)/Re (550) was calculated. The results are shown in Table 1 shown below.

<Durability>

Each of the optical films prepared in the examples and comparative examples described above was bonded to a glass plate through a pressure sensitive adhesive, in a state where the optically-anisotropic layer side faced the glass side.

By using Axo Scan (OPMF-1, manufactured by Axometrics, Inc.), the durability of the retardation value was evaluated based on the parameters described below. The results are shown in Table 1 shown below.

Regarding the test conditions, as shown in Table 1 shown below, a test was performed in which the optical film was left to stand for 1,000 hours in an environment of 60° C. and a relative humidity of 90%, and a test was performed in which the optical film was left to stand for 120 hours in an environment of 85° C. and a relative humidity of 85° C. In a case where an optical film is evaluated as "A" in the test in which the optical film is left to stand for 1,000 hours in an environment of 85° C. and a relative humidity of 85%, it is possible to make a determination that the durability thereof is excellent.

A: The amount of change in the retardation value after the test with respect to the initial retardation value is less than 5% of the initial value.

B: The amount of change in the retardation value after the test with respect to the initial retardation value is equal to or greater than 5% and less than 10% of the initial value.

C: The amount of change in the retardation value after the test with respect to the initial retardation value is equal to or greater than 10% of the initial value.

TABLE 1

|  | Liquid crystal compound | Polymerizable compound | Re (450)/ Re (550) | 60° C. Relative humidity 90% 1,000 hours | 85° C. Relative humidity 85% 120 hours |
|---|---|---|---|---|---|
| Example 1 | L-1/L-2 | (I-1) | 0.85 | A | A |
| Example 2 | L-1/L-2 | (I-2) | 0.84 | A | A |
| Example 3 | L-1/L-2 | (I-3) | 0.84 | A | A |
| Example 4 | L-1/L-2 | (I-4) | 0.85 | A | A |
| Example 5 | L-1/L-2 | (I-5) | 0.85 | A | A |
| Example 6 | L-1/L-2 | (I-6) | 0.85 | A | A |
| Example 7 | L-6 | (I-7) | 0.85 | A | A |
| Example 8 | L-7 | (I-7) | 0.85 | A | A |
| Comparative Example 1 | L-1/L-2 | Absent | 0.82 | B | C |
| Comparative Example 2 | L-1/L-2 | (X-1) | 0.85 | A | B |
| Comparative Example 3 | L-1/L-2 | (X-2) | 0.84 | A | B |
| Comparative Example 4 | L-1/L-2 | (X-3) | 0.84 | A | B |
| Comparative Example 5 | L-1/L-2 | (X-4) | 0.85 | A | B |
| Comparative Example 6 | L-1/L-2 | (X-5) | 0.85 | A | B |
| Comparative Example 7 | L-1/L-2 | (X-6) | 0.85 | A | B |
| Comparative Example 8 | L-6 | Absent | 0.82 | B | C |
| Comparative Example 9 | L-7 | Absent | 0.82 | B | C |

As is evident from the results shown in Table 1, in a case where the polymerizable compound represented by Formula (I) shown above is not used, even though the liquid crystal compound represented by Formula (II) shown above is used, the durability is poor (Comparative Examples 1, 8, and 9).

Furthermore, it was revealed that in a case where other polymerizable compounds represented by Formula (I) shown above, in which only the structure of $Ar^1$ is different, is used instead of the polymerizable compound represented by Formula (I) shown above, the durability is slightly improved compared to Comparative Example 1 but is insufficient (Comparative Examples 2 to 7).

In contrast, it was revealed that in a case where the polymerizable compound represented by Formula (I) shown above and the liquid crystal compound represented by Formula (II) shown above are used, the durability becomes excellent in all of the optical films (Examples 1 to 8).

EXPLANATION OF REFERENCES

10: optical film
12: optically-anisotropic layer
14: alignment film
16: support
18: hardcoat layer

What is claimed is:
1. An optical film comprising:
at least an optically-anisotropic layer,
wherein the optically-anisotropic layer is a layer obtained by polymerizing a polymerizable liquid crystal composition containing a polymerizable compound which is represented by Formula (I), a liquid crystal compound which is represented by Formula (II) and does not correspond to Formula (I), and a polymerization initiator,

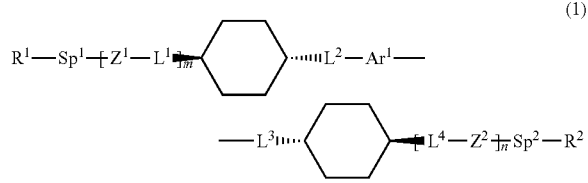
(1)

in Formula (I), m and n each independently represent an integer of 0 to 2, m+n equals an integer of 2 to 4, $Z^1$ and $Z^2$ each independently represent a trans-1,4-cyclohexylene group which may have a substituent, an arylene group which may have a substituent, or a heteroarylene group which may have a substituent, in a case where m is 2, a plurality of $Z^1$'s may be the same as or different from each other, in a case where n is 2, a plurality of $Z^2$'s may be the same as or different from each other, at least one of $Z^1$ or $Z^2$ represents an arylene group which may have a substituent or a heteroarylene group which may have a substituent, $L^1$, $L^2$, $L^3$, and $L^4$ each independently represent any linking group selected from the group consisting of a single bond, —O—, —CH$_2$O—, —OCH$_2$—, —(CH$_2$)$_2$OC(=O)—, —C(=O)O(CH$_2$)$_2$—, —NH—, —N(CH$_3$)—, —S—, —C(=O)O—, —OC(=O)—, —OC(=O)O—, —C(=O)N(R$^3$)—, —N(R$^3$)C(=O)—, —C(=O)S—, —SC(=O)—, —CH$_2$C(=O)O—, —OC(=O)CH$_2$—, —CH=CH—C(=O)O—, —OC(=O)—CH=CH—, —CH=N—, —N=CH—, and —N=N—, $R^3$ represents a hydrogen atom, an alkyl group having 1 to 20 carbon atoms, or an aryl group having 6 to 20 carbon atoms, in a case where m is 2, a plurality of $L^1$'s may be the same as or different from each other, in a case where n is 2, a plurality of $L^4$'s may be the same as or different from each other, $Sp^1$ and $Sp^2$ each independently represent any linking group selected from the group consisting of a single bond, a linear or branched alkylene group having 1 to 20 carbon atoms, and a group obtained in a case where one or more —CH$_2$— groups constituting a linear or branched alkylene group having 1 to 20 carbon atoms are substituted with —O—, —S—, —NH—, —N(CH$_3$)—, —C(=O)—, —OC(=O)—, or —C(=O)O—, $R^1$ and $R^2$ each independently represent any polymerizable group selected from the group consisting of groups represented by Formulae (R-1) to (R-5), and $Ar^1$ represents any aromatic ring selected from the group consisting of groups represented by Formulae (Ar-1) to (Ar-4),

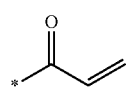
(R-1)

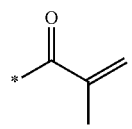
(R-2)

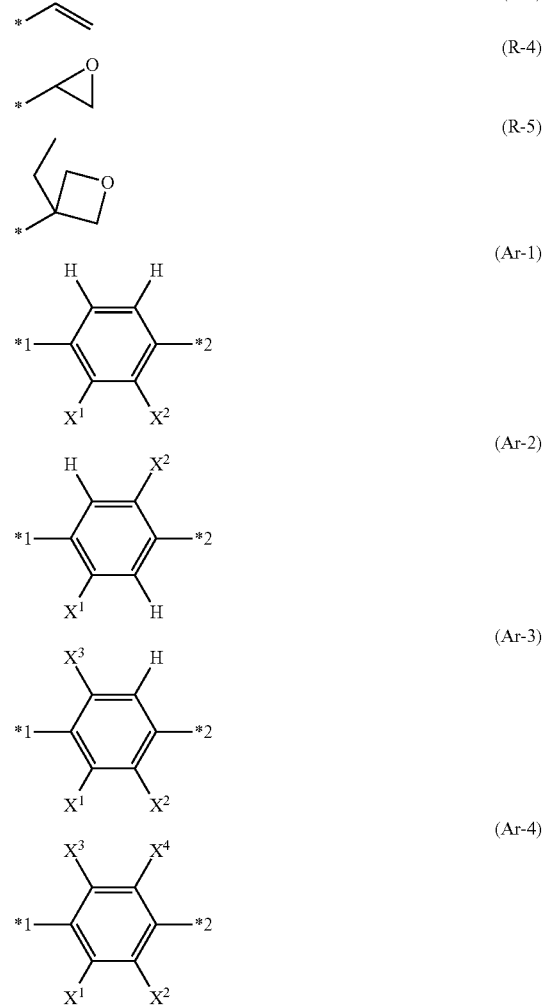

in Formulae (R-1) to (R-5), * represents a position bonded to $Sp^1$ or $Sp^2$, in Formulae (Ar-1) to (Ar-4), $X^1$, $X^2$, $X^3$, and $X^4$ each independently represent a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —CO$_2$R$^4$, —NR$^5$R$^6$, or SR$^5$, $R^4$, $R^5$, and $R^6$ each independently represent a hydrogen atom or an alkyl group having 1 to 6 carbon atoms, *1 represents a position bonded to $L^2$, and *2 represents a position bonded to $L^3$,

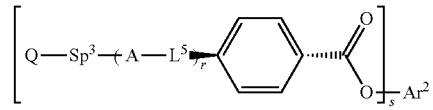
(II)

in Formula (II), $Ar^2$ represents an s-valent aromatic group, $L^5$ represents a single bond, —COO—, or —OCO—, A represents an aromatic ring having 6 or more carbon atoms or a cycloalkylene ring having 6 or more carbon atoms, Sp³ represents a single bond, a linear or branched alkylene group having 1 to 12 carbon atoms, or a divalent linking group obtained in a case where one or more —CH₂— groups constituting a linear or branched alkylene group having 1 to 12 carbon atoms are substituted with —O—, —S—, —NH—, —N(Q)-, or —CO—, Q represents a polymerizable group, r represents an integer of 0 to 2, s represents an integer of 1 or 2, and all of $L^5$, A, $Sp^3$, and Q, each of which becomes a plurality of groups depending on the number represented by r or s, may be the same as or different from each other.

2. The optical film according to claim 1,
wherein the optically-anisotropic layer satisfies Expression (1), $$0.75 < Re(450)/Re(550) < 1.00 \quad (1)$$

in Expression (1), Re (450) represents in-plane retardation of the optically-anisotropic layer at a wavelength of 450 nm, and Re (550) represents in-plane retardation of the optically-anisotropic layer at a wavelength of 550 nm.

3. The optical film according to claim 1,
wherein the liquid crystal compound is a liquid crystal compound exhibiting reciprocal wavelength dispersion properties.

4. The optical film according to claim 1,
wherein both of m and n in Formula (I) represent 1.

5. The optical film according to claim 1,
wherein both of $Z^1$ and $Z^2$ in Formula (I) represent an arylene group which may have a substituent.

6. The optical film according to claim 1,
wherein all of $L^1$, $L^2$, $L^3$, and $L^4$ in Formula (I) represent —C(=O)O— or —OC(=O)—.

7. The optical film according to claim 1,
wherein $Sp^1$ and $Sp^2$ in Formula (I) represent a linking group selected from the groups formed in a case where one or more —CH₂— groups constituting a linear or branched alkylene group having 5 to 15 carbon atoms are substituted with —O—, —OC(=O)—, or —C(=O)O—.

8. The optical film according to claim 1,
wherein $R^1$ and $R^2$ in Formula (I) represent an acryloyl group represented by Formula (R-1) or a methacryloyl group represented by Formula (R-1).

9. The optical film according to claim 1,
wherein $Ar^1$ in Formula (I) is an aromatic ring represented by Formula (Ar-3).

10. The optical film according to claim 1,
wherein the polymerization initiator is an oxime-type polymerization initiator.

11. A polarizing plate comprising:
the optical film according to claim 1; and
a polarizer.

12. An image display device comprising:
the optical film according to claim 1.

13. A polymerizable compound represented by Formula (I), in Formula (I), m and n each independently represent an integer of 0 to 2, m+n equals an integer of 2 to 4, $Z^1$ and $Z^2$ each independently represent a trans-1,4-cyclohexylene group which may have a substituent, an arylene group which may have a substituent, or a heteroarylene group which may have a substituent, in a case where m is 2, a plurality of $Z^1$'s may be the same as or different from each other, in a case where n is 2, a plurality of $Z^2$'s may be the same as or different from each other, at least one of $Z^1$ or $Z^2$ represents an arylene group which may have a substituent or a heteroarylene group which may have a substituent, $L^1$, $L^2$, $L^3$, and $L^4$ each independently represent any linking group selected from the group consisting of a single bond, —O—, —CH₂O—, —OCH₂—, —(CH₂)₂OC(=O)—, —C(=O)O(CH₂)₂—, —NH—, —N(CH₃)—, —S—, —C(=O)O—, —OC(=O)—, —OC(=O)O—, —C(=O)N(R³)—, —N(R³)C(=O)—, —C(=O)S—, —SC(=O)—, —CH₂C(=O)O—, —OC(=O)CH₂—, —CH=CH—C(=O)O—, —OC(=O)—CH=CH—, —CH=N—, —N=CH—, and —N=N—, $R^3$ represents a hydrogen atom, an alkyl group having 1 to 20 carbon atoms, or an aryl group having 6 to 20 carbon atoms, in a case where m is 2, a plurality of $L^1$'s may be the same as or different from each other, in a case where n is 2, a plurality of $L^4$'s may be the same as or different from each other, $Sp^1$ and $Sp^2$ each independently represent any linking group selected from the group consisting of a single bond, a linear or branched alkylene group having 1 to 20 carbon atoms, and a group obtained in a case where one or more —CH₂— groups constituting a linear or branched alkylene group having 1 to 20 carbon atoms are substituted with —O—, —S—, —NH—, —N(CH₃)—, —C(=O)—, —OC(=O)—, or —C(=O)O—, $R^1$ and $R^2$ each independently represent any polymerizable group selected from the group consisting of groups represented by Formulae (R-1) to (R-5), and $Ar^1$ represents any aromatic ring selected from the group consisting of groups represented by Formulae (Ar-1) to (Ar-4),

(R-1)

(R-2)

(R-3)

(R-4)

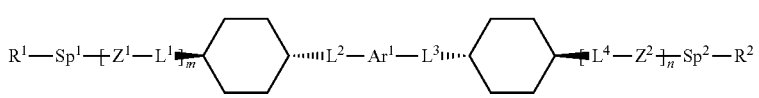
(I)

-continued (R-5)

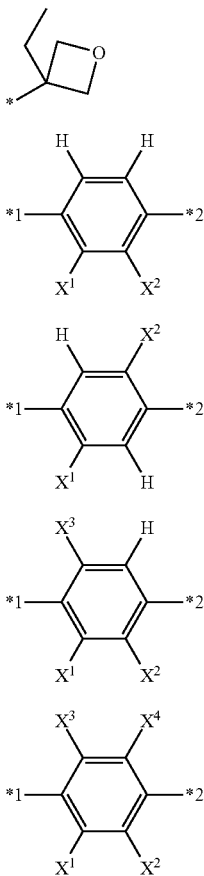

(Ar-1)

(Ar-2)

(Ar-3)

(Ar-4)

in Formulae (R-1) to (R-5), * represents a position bonded to $Sp^1$ or $Sp^2$, in Formulae (Ar-1) to (Ar-4), $X^1$, $X^2$, $X^3$, and $X^4$ each independently represent a monovalent aliphatic hydrocarbon group having 1 to 20 carbon atoms, a monovalent alicyclic hydrocarbon group having 3 to 20 carbon atoms, a monovalent aromatic hydrocarbon group having 6 to 20 carbon atoms, a halogen atom, a cyano group, a nitro group, —$CO_2R^4$, —$NR^5R^6$, or $SR^5$, $R^4$, $R^5$, and $R^6$ each independently represent a hydrogen atom or an alkyl group having 1 to 6 carbon atoms, *1 represents a position bonded to $L^2$, and *2 represents a position bonded to $L^3$.

14. The polymerizable compound according to claim 13, wherein both of m and n in Formula (I) represent 1.

15. The polymerizable compound according to claim 13, wherein both of $Z^1$ and $Z^2$ in Formula (I) represent an arylene group which may have a substituent.

16. The polymerizable compound according to claim 13, wherein all of $L^1$, $L^2$, $L^3$, and $L^4$ in Formula (I) represent —C(=O)O— or —OC(=O)—.

17. The polymerizable compound according to claim 13, wherein $Sp^1$ and $Sp^2$ in Formula (I) represent a linking group selected from the groups formed in a case where one or more —$CH_2$— groups constituting a linear or branched alkylene group having 5 to 15 carbon atoms are substituted with —O—, —OC(=O)—, or —C(=O)O—.

18. The polymerizable compound according to claim 13, wherein $R^1$ and $R^2$ in Formula (I) represent an acryloyl group represented by Formula (R-1) or a methacryloyl group represented by Formula (R-1).

19. The polymerizable compound according to claim 13, wherein $Ar^1$ in Formula (I) is an aromatic ring represented by Formula (Ar-3).

* * * * *